US012253499B2

(12) United States Patent
Ibsen et al.

(10) Patent No.: US 12,253,499 B2
(45) Date of Patent: Mar. 18, 2025

(54) THIN-LAYER CHROMATOGRAPHY SYSTEM AND METHOD FOR ASSESSING ANALYTE CONCENTRATIONS IN SAMPLES

(71) Applicant: UCL BUSINESS LTD, London (GB)

(72) Inventors: Stuart Ibsen, London (GB); Alaric Taylor, London (GB); Simon Dawes, London (GB); Luis Antonio Serrano Gonzalez, London (GB); Stefan Guldin, London (GB)

(73) Assignee: UCL BUSINESS LTD, London (GB)

( * ) Notice: Subject to any disclaimer, the term of this patent is extended or adjusted under 35 U.S.C. 154(b) by 441 days.

(21) Appl. No.: 16/768,136

(22) PCT Filed: Nov. 29, 2018

(86) PCT No.: PCT/EP2018/083050
§ 371 (c)(1),
(2) Date: May 29, 2020

(87) PCT Pub. No.: WO2019/106107
PCT Pub. Date: Jun. 6, 2019

(65) Prior Publication Data
US 2020/0319152 A1 Oct. 8, 2020

(30) Foreign Application Priority Data
Nov. 30, 2017 (GB) ...................... 1719905

(51) Int. Cl.
*G01N 30/90* (2006.01)
*G01N 1/40* (2006.01)
(Continued)

(52) U.S. Cl.
CPC ........... *G01N 30/90* (2013.01); *G01N 1/4077* (2013.01); *G01N 30/14* (2013.01); *G01N 30/26* (2013.01);
(Continued)

(58) Field of Classification Search
CPC ...... G01N 30/90; G01N 1/4077; G01N 30/14; G01N 30/26; G01N 30/74; G01N 33/94; G01N 2001/4083; G01N 30/88
See application file for complete search history.

(56) References Cited

U.S. PATENT DOCUMENTS 3,682,315 A * 8/1972 Haller .................... B01D 15/22
210/477
6,783,988 B1 * 8/2004 Dinh ...................... G01N 33/92
422/70

(Continued)

FOREIGN PATENT DOCUMENTS

CN 204044122 U 12/2014
DE 2823476 A1 9/1979
(Continued)

OTHER PUBLICATIONS

Nicola, A.J. et al. "Direct Quantitative Analysis from Thin-Layer Chromatography Plates Using Matrix-Assisted Laser Desorption/Ionization Mass Spectrometry," Sep. 13, 1996, Society for Applied Spectroscopy, vol. 50, No. 12, pp. 1479-1482. (Year: 1996).*

(Continued)

*Primary Examiner* — Jill A Warden
(74) *Attorney, Agent, or Firm* — Withrow + Terranova, PLLC; Vincent K. Gustafson

(57) ABSTRACT

The invention relates to cartridges for thin layer chromatography (TLC) which hermetically seal the TLC mobile phase during loading, performance of the TLC process, and analysis of the chromatogram. It further relates to associated methods of use—for example for detecting or quantifying an analyte in a sample. It further relates to processes for assembling the cartridge, to associated equipment adapted for use with them, and kits of parts.

19 Claims, 31 Drawing Sheets

Figure 1:
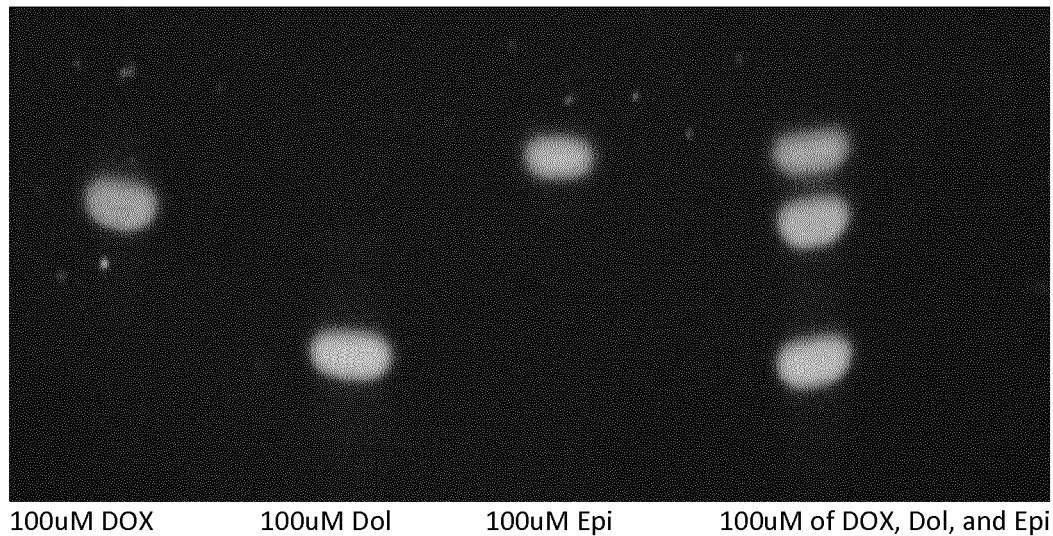

(51) Int. Cl.
G01N 30/14 (2006.01)
G01N 30/26 (2006.01)
G01N 30/74 (2006.01)
G01N 33/94 (2006.01)
(52) U.S. Cl.
CPC ............. *G01N 30/74* (2013.01); *G01N 33/94* (2013.01); *G01N 2001/4083* (2013.01)

(56) References Cited

U.S. PATENT DOCUMENTS

| | | | |
|---|---|---|---|
| 6,936,167 | B2 | 8/2005 | Hobbs et al. |
| 7,247,273 | B2 | 7/2007 | Nunes et al. |
| 7,745,227 | B2 | 6/2010 | Haas |
| 9,671,377 | B2 | 6/2017 | Minoda et al. |
| 9,709,582 | B1 * | 7/2017 | Gordon ................ G01N 33/582 |
| 2004/0042934 | A1 | 3/2004 | Nunes et al. |
| 2005/0064601 | A1 * | 3/2005 | Haas ...................... G01N 30/90 436/109 |
| 2009/0181388 | A1 * | 7/2009 | You ...................... C12Q 1/6848 435/287.2 |
| 2011/0239745 | A1 | 10/2011 | Satcher, Jr. et al. |
| 2014/0096596 | A1 | 4/2014 | Brousmiche et al. |
| 2018/0292369 | A1 * | 10/2018 | Stitzlein et al. |

FOREIGN PATENT DOCUMENTS

| | | |
|---|---|---|
| EP | 2579034 A1 | 4/2013 |
| EP | 2765418 A1 | 8/2014 |
| GB | 1211468 A | 11/1970 |
| JP | 2007292540 A | 11/2007 |
| JP | 2010190573 A | 9/2010 |
| JP | 2014215266 A | 11/2014 |
| WO | 2012070431 A1 | 5/2012 |
| WO | 2016153980 A1 | 9/2016 |

OTHER PUBLICATIONS

Nash, John J., Jeanne A. Meyer, and Barbara Everson. "What factors affect the separation of substances using thin-layer chromatography? An undergraduate experiment." Journal of Chemical Education 78.3 (2001): 364. (Year: 2001).*

Therasse, P. et al., "New Guidelines to Evaluate the Response to Treatment in Solid Tumors," Journal of the National Cancer Institute, vol. 92, No. 3, Feb. 2, 2000, Oxford University Press, pp. 205-216.

Torre, L. et al., "Global Cancer Statistics, 2012," CA: A Cancer Journal for Clinicians, vol. 65, No. 2, Mar./Apr. 2015, American Cancer Society, pp. 87-108.

Touw, D.J. et al., "Cost-Effectiveness of Therapeutic Drug Monitoring: A Systematic Review," Therapeutic Drug Monitoring, vol. 27, No. 1, Feb. 2005, Lippincott Williams & Wilkins, pp. 10-17.

Wadagni, A. et al., "Simple, Rapid Mycobacterium ulcerans Disease Diagnosis from Clinical Samples by Fluorescence of Mycolactone on Thin Layer Chromatography," PLoS Neglected Tropical Diseases, vol. 9, No. 11, Nov. 19, 2015, 9 pages.

Widmer, N. et al., "Review of therapeutic drug monitoring of anticancer drugs part two—Targeted therapies," European Journal of Cancer, vol. 50, Jun. 2014, Elsevier Ltd., pp. 2020-2036.

Wilkinson, G.R., "Drug Metabolism and Variability among Patients in Drug Response," The New England Journal of Medicine, vol. 352, No. 21, May 26, 2005, Massachusetts Medical Society, pp. 2211-2221.

Wilson, I., "Thin-Layer Chromatography: A Neglected Technique," Therapeutic Drug Monitoring, vol. 18, No. 4, Aug. 1996, Wolters Kluwer, pp. 484-492.

Yesair, D.W. et al., "Comparative Pharmacokinetics of Daunomycin and Adriamycin in Several Animal Species," Cancer Research, vol. 32, Jun. 1972, American Association for Cancer Research, pp. 1177-1183.

Ashbee, H.R. et al., "Therapeutic drug monitoring (TDM) of antifungal agents: guidelines from the British Society for Medical Mycology," Journal of Antimicrobial Chemotherapy, vol. 69, May 2014, Advance Access publication Dec. 29, 2013, Oxford University Press, pp. 1162-1176.

Author Unknown, "Bioanalytical Method Validation: Guidance for Industry," U.S. Department of Health and Human Services, Food and Drug Administration, May 24, 2018, 44 pages.

Author Unknown, "How Can We Tell if Chemotherapy is Working?" Chemocare.com, 2016, accessed Oct. 2020 from https://chemocare.com/chemotherapy/what-is-chemotherapy/how-to-tell-if-chemotherapy-is-working.aspx, 3 pages.

Author Unknown, "Preoperative tests: Routine preoperative tests for elective surgery," Draft for consultation, Clinical guideline <. . . >, Appendix G: Literature search strategies, Oct. 2015, National Clinical Guideline Centre, 30 pages.

Author Unknown, "QBC Dry Hematology Analyzers for Point of Care Testing," Drucker Diagnostics, 2019, accessed Oct. 2020 from https://druckerdiagnostics.com/point-of-care-hematology-testing/, 4 pages.

Author Unknown, "Therapeutic Drug MonitoringMarket Worth $3.37 Billion By 2024: Grand View Research, Inc.," GlobeNewswire, Aug. 19, 2016, https://www.globenewswire.com/news-release/2016/08/19/865455/0/en/Therapeutic-Drug-Monitoring-Market-Worth-3-37-Billion-By-2024-Grand-View-Research-Inc.html, 5 pages.

Azhar, M. et al., "Microfluidic platforms forpoint of care (POC) medical diagnostics," Chapter 11, Medical Biosensors for Point of Care (POC) Applications, 2017, Elsevier Ltd., pp. 255-273.

Bach, D. et al., "Therapeutic drug monitoring in cancer chemotherapy," Bioanalysis, vol. 2, No. 5, May 2010, Future Science Ltd., pp. 863-879.

Bammesberger, S.B. et al., "A Calibration-Free, Noncontact, Disposable Liquid Dispensing Cartridge Featuring an Online Process Control," Journal of Laboratory Automation, vol. 19, No. 4, Aug. 2013, Society for Laboratory Automation and Screening, pp. 394-402.

Bardin, C. et al., "Therapeutic drug monitoring in cancer—Are we missing a trick?" European Journal of Cancer, vol. 50, May 2014, Elsevier Ltd., pp. 2005-2009.

Besse, B. et al., "2nd ESMO Consensus Conference on Lung Cancer: non-small-cell lung cancer first line/second and further lines of treatment in advanced disease," Annals of Oncology, vol. 25, No. 8, Aug. 2014, published online Mar. 25, 2014, Oxford University Press, pp. 1475-1484.

Bouma, J. et al., "Anthracycline antitumour agents: A review of physicochemical, analytical and stability properties," Pharmaceutisch Weekblad Scientific Edition, vol. 8, Jun. 1986, pp. 109-133.

Brenner, D. et al., "Improved high-performance liquid chromatography assay of doxorubicin: Detection of circulating aglycones in human plasma and comparison with thin-layer chromatography," Cancer Chemotherapy and Pharmacology, vol. 14, 1985, Springer-Verlag, pp. 139-14.

Brun, J.F. et al., "The paradox of hematocrit in exercise physiology: which is the "normal" range from an hemorheologist's viewpoint?" Clinical Hemorheology and Microcirculation, vol. 22, No. 4, 2000, IOS Press, pp. 287-30.

Chin, C.D. et al., "Chapter 1: Low-Cost Microdevices for Point-of-Care Testing," in Point-of-Care Diagnostics on a Chip, Issadore, David and Westervelt, Robert M. (Eds.), 2013, Springer, 19 pages.

Davis, C.M. et al., "Quantitation of Thiothixene in Plasma by High-Performance Thin-Layer Chromatography and Fluorometric Detection," Therapeutic Drug Monitoring, vol. 10, No. 2, 1988, Raven Press, Ltd., pp. 215-222.

De Jonge, M. et al., "Individualised Cancer Chemotherapy: Strategies and Performance of Prospective Studies on Therapeutic Drug Monitoring with Dose Adaptation," Clinical Pharmacokinetics, vol. 44, No. 2, 2005, Adis Data Information BV, pp. 147-17.

Dodde, W. et al., "Determination of Epirubicin and Its Metabolite Epirubicinol in Saliva and Plasma by HPLC," Therapeutic Drug Monitoring, vol. 25, No. 4, Aug. 2003, Lippincott Williams & Wilkins, Inc., pp. 433-444.

(56) References Cited

OTHER PUBLICATIONS

Dodwell, D.J. et al., "Dose intensity in cancer chemotherapy," British Journal of Cancer, vol. 61, No. 6, Jun. 1990, Macmillan Press Ltd., pp. 789-794.

Fogli, S. et al., "An Improved HPLC Method for Therapeutic Drug Monitoring of Daunorubicin, Idarubicin, Doxorubicin, Epirubicin, and Their 13-Dihydro Metabolites in Human Plasma," Therapeutic Drug Monitoring, vol. 21, No. 3, Jun. 1999, Lippincott Williams & Wilkins, Inc., pp. 367-375.

Fredriksson, S. et al., "Fatty acid and carotenoid composition of egg yolk as an effect of microalgae addition to feed formula for laying hens," Food Chemistry, vol. 99, 2006, Elsevier Ltd., pp. 530-537.

Gurney, H., "Dose Calculation of Anticancer Drugs: A Review of the Current Practice and Introduction of an Alternative," Journal of Clinical Oncology, vol. 14, No. 9, Sep. 1996, American Society of Clinical Oncology, pp. 2590-2611.

Gurney, H. et al., "Escalating drug delivery in cancer chemotherapy: A review of concepts and practice—Part 1," Annals of Oncology, vol. 4, Issue 1, Jan. 1993, Kluwer Academic Publishers, pp. 23-34.

Gurney, H. et al., "Escalating drug delivery in cancer chemotherapy: A review of concepts and practice—Part 2," Annals of Oncology, vol. 4, Issue 2, Feb. 1993, Kluwer Academic Publishers, pp. 103-115.

Gurney, H. et al., "Factors Affecting Epirubicin Pharmacokinetics and Toxicity: Evidence Against Using Body-Surface Area for Dose Calculation," Journal of Clinical Oncology, vol. 16, No. 7, Jul. 1998, American Society of Clinical Oncology, pp. 2299-2304.

Gurney, H., "How to calculate the dose of chemotherapy," British Journal of Cancer, vol. 86, No. 8, Apr. 22, 2002, Cancer Research UK, pp. 1297-1302.

Haber, C. et al., "Precise Nanoliter Fluid Handling System with Integrated High-Speed Flow Sensor," ASSAY and Drug Development Technologies, vol. 3, No. 2, 2005, Mary Ann Liebert, Inc., 11 pages.

Haeberle, S. et al., "Centrifugal extraction of plasma from whole blood on a rotating disk," Lab on a Chip, vol. 6, 2006, The Royal Society of Chemisty, pp. 776-781.

Hortobagyi, G.N. et al., "Anthracyclines in the Treatment of Cancer," Drugs, vol. 54, Suppl. 4, 1997, Adis International Limited, pp. 1-7.

Ibsen, S. et al., "Extraction protocol and mass spectrometry method for quantification of doxorubicin released locally from prodrugs in tumor tissue," Journal of Mass Spectrometry, Jul. 2013, vol. 48, No. 7, John Wiley & Sons, pp. 768-773.

Johnston, A. et al., "Therapeutic drug monitoring of immunosuppressant drugs," British Journal of Clinical Pharmacology, vol. 47, No. 4, Apr. 1999, Blackwell Science Ltd., pp. 339-350.

Jurgens, G. et al., "Therapeutic Drug Monitoring of Antiarrhythmic Drugs," Clinical Pharmacokinetics, vol. 42, No. 7, 2003, Adis Data Information BV, pp. 647-664.

Klotz, U., "Pharmacokinetics and drug metabolism in the elderly," Drug Metabolism Reviews, vol. 41, No. 2, May 1, 2009, Informa UK Ltd., pp. 67-76.

Kontny, N. et al., "Minimization of the Preanalytical Error in Plasma Samples for Pharmacokinetic Analyses and Therapeutic Drug Monitoring—Using Doxorubicin as an Example," Therapeutic Drug Monitoring, vol. 33, No. 6, Dec. 2011, Lippincott Williams & Wilkins, pp. 766-771.

Krischke, M. et al., "Pharmacokinetic and pharmacodynamic study of doxorubicin in children with cancer: results of a "European Pediatric Oncology Off-patents Medicines Consortium" trial," Cancer Chemotherapy and Pharmacology, vol. 78, No. 6, Dec. 2016, pp. 1175-1184.

Lennard, L., "Therapeutic drug monitoring of cytotoxic drugs," British Journal of Clinical Pharmacology, vol. 52, Sep. 2001, Blackwell Science Ltd., pp. 75S-87S.

Licata, S. et al., "Doxorubicin Metabolism and Toxicity in Human Myocardium: Role of Cytoplasmic Deglycosidation and Carbonyl Reduction," Chemical Research in Toxicology, vol. 13, No. 5, May 2000, American Chemical Society, pp. 414-420.

Marangon, E. et al., "Development and Validation of a High-Performance Liquid Chromatography—Tandem Mass Spectrometry Method for the Simultaneous Determination of Irinotecan and Its Main Metabolites in Human Plasma and Its Application in a Clinical Pharmacokinetic Study," PLoS One, vol. 10, No. 2, Feb. 17, 2015, 18 pages.

Mcdade, T. et al., "What a drop can do: dried blood spots as a minimally invasive method for integrating biomarkers into population-based research," Demography, vol. 44, No. 4, Nov. 2007, pp. 899-925.

Paci, A. et al., "Review of therapeutic drug monitoring of anticancer drugs part 1—Cytotoxics," European Journal of Cancer, vol. 50, No. 12, Aug. 2014, Elsevier Ltd., pp. 2010-2019.

Papu, J. et al., "A Portable Centrifuge for Point-of-Care Measurement of Hematocrit in Low-Resource Settings," Point of Care, vol. 13, No. 2, Jun. 2014, Lippincott Williams & Wilkins, pp. 48-53.

Petros, W.P. et al., "Associations Between Drug Metabolism Genotype, Chemotherapy Pharmacokinetics, and Overall Survival in Patients With Breast Cancer," Journal of Clinical Oncology, vol. 23, No. 25, Sep. 1, 2005, American Society of Clinical Oncology, pp. 6117-6125.

Pihl, J. et al., "Microfluidic technologies in drug discovery," Drug Discovery Today, vol. 10, No. 20, Oct. 2005, Elsevier Ltd., pp. 1377-1383.

Robert, J. et al., "Pharmacokinetics of Adriamycin in Patients with Breast Cancer: Correlation between Pharmacokinetic Parameters and Clinical Short-term Response," European Journal of Cancer and Clinical Oncology, vol. 18, No. 8, Aug. 1982, Pergamon Press Ltd., pp. 739-745.

Roberts, J. et al., "Therapeutic drug monitoring of antimicrobials," British Journal of Clinical Pharmacology, vol. 73, No. 1, Jan. 2012, The British Pharmacological Society, pp. 27-36.

Robison, E. et al., "Whole genome transcript profiling from fingerstick blood samples: a comparison and feasibility study," BMC Genomics, vol. 10, No. 617, Dec. 17, 2009, 9 pages.

Sanavio, B. et al., "On the slow diffusion of point-of-care systems in therapeutic drug monitoring," Frontiers in Bioengineering and Biotechnology, vol. 3, Article 20, Feb. 2015, 15 pages.

Sawyer, M. et al., "Body surface area as a determinant of pharmacokinetics and drug dosing," Investigational New Drugs, vol. 19, 2001, Kluwer Academic Publishers, pp. 171-177.

Stahl, E. et al., "A Thermo Micro Procedure for Rapid Extraction and Direct Application in Thin-layer Chromatography," Analyst, vol. 94, Issue 1122, Sep. 1969, pp. 723-727.

Stone, K. et al., "Top 20 Blockbuster Cancer Drugs: 2018 Best Selling Oncology Drugs Include Revlimid and Avastin," The Balance, Nov. 20, 2019, https://www.thebalance.com/top-cancer-drugs-2663234, 10 pages.

Notification of Transmittal of the International Search Report and the Written Opinion (Form PCT/ISA/220), International Search Report (Form PCT/ISA/210), and Written Opinion (Form PCT/ISA/237) for International Application No. PCT/EP2018/083050 mailed Mar. 15, 2019, 20 pages.

Satcher, J.H., et al., "Portable Thin Layer Chromatography for Field Detection of Explosives and Propellants," Chemical, Biological, Radiological, Nuclear, and Explosives (CBRNE) Sensing XIII, Proc. of SPIE vol. 8358, No. 1, pp. 1-10, SPIE (Bellingham, WA, USA), May 11, 2020.

Chan, K.K., et al., "Quantitative thin-layer chromatography: thin-film fluorescence scanning analysis for adriamycin and metabolites in tissue," Journal of Chromatography A., vol. 172, No. 1, pp. 343-349, Elsevier (Amsterdam, NL), Apr. 21, 1979.

Lemmo, A.V., et al., "Micro Parallel Liquid Chromatography: Enabling Technology for Discovery Analytical Chemistry," Assay and Drug Development Technologies, vol. 2, No. 4, Mary Ann Liebert, Inc., 2004.

* cited by examiner

100uM DOX     100uM Dol     100uM Epi     100uM of DOX, Dol, and Epi

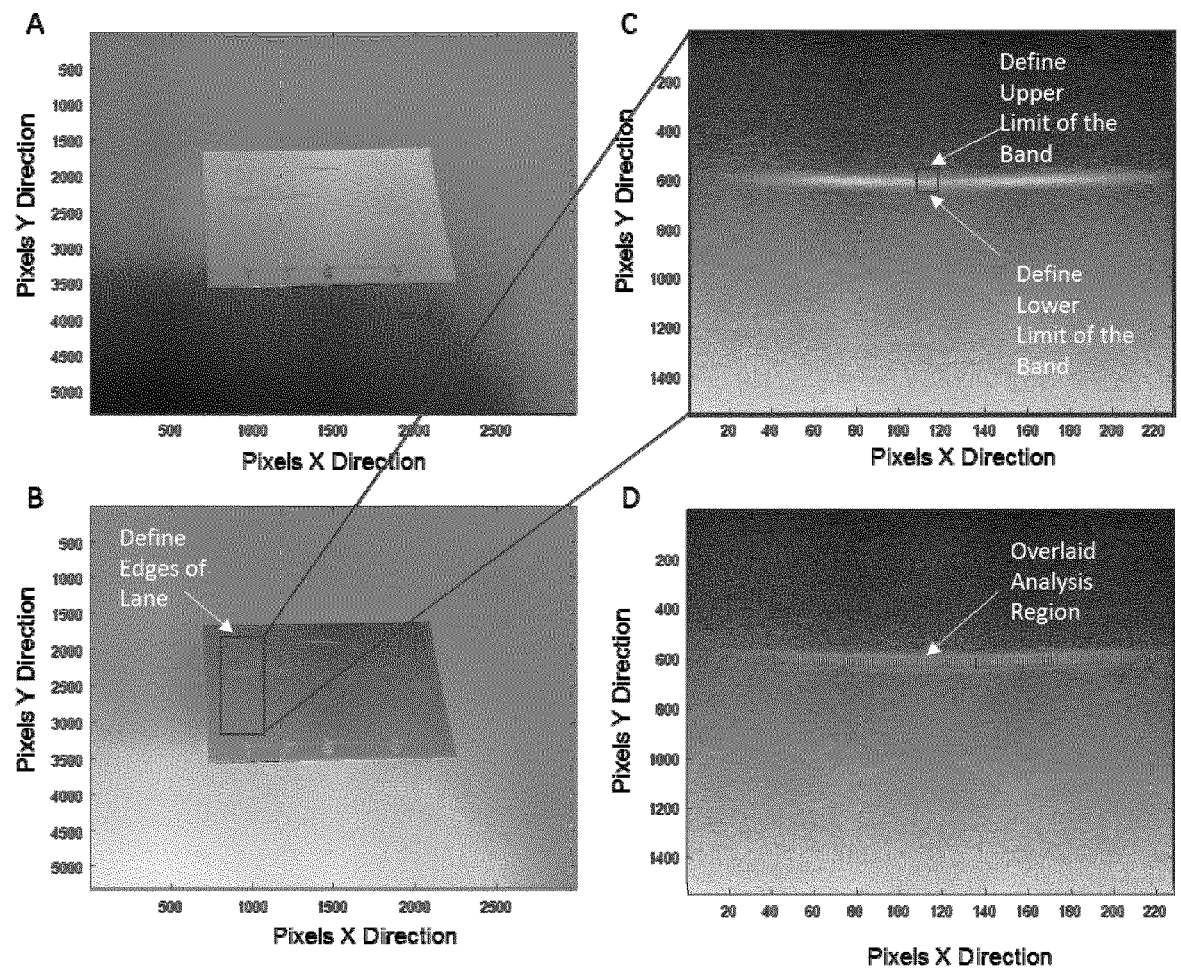
Figure 13A-D

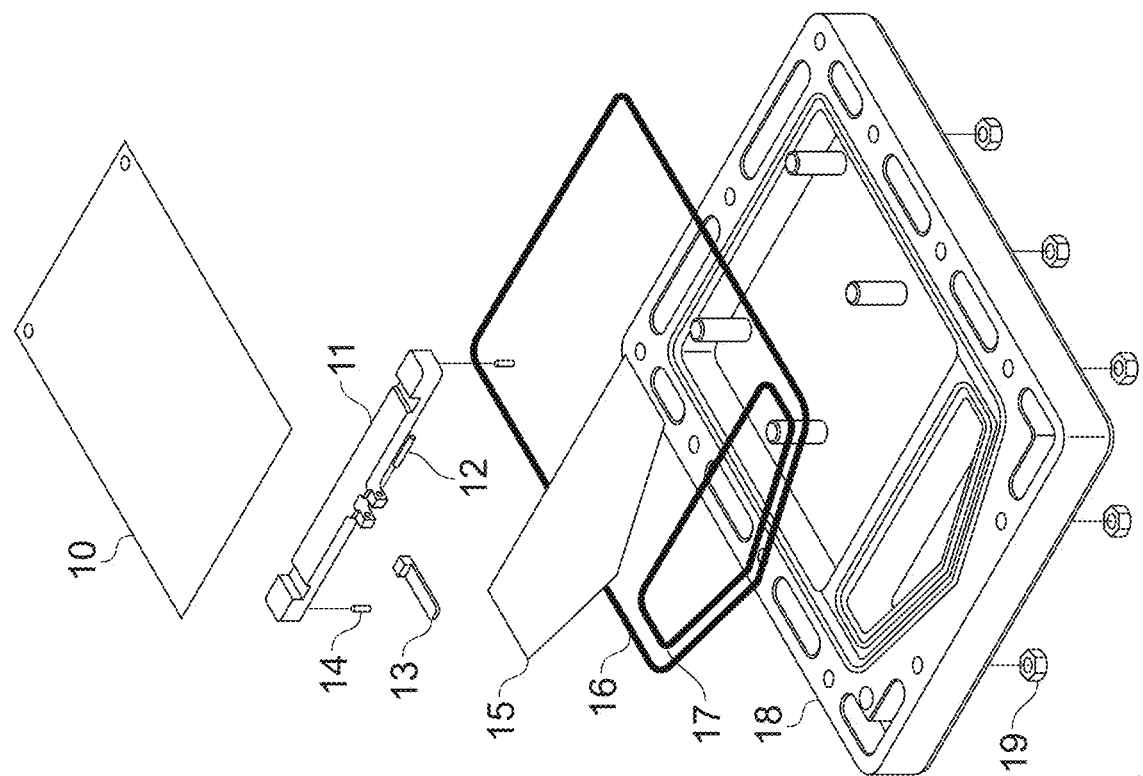
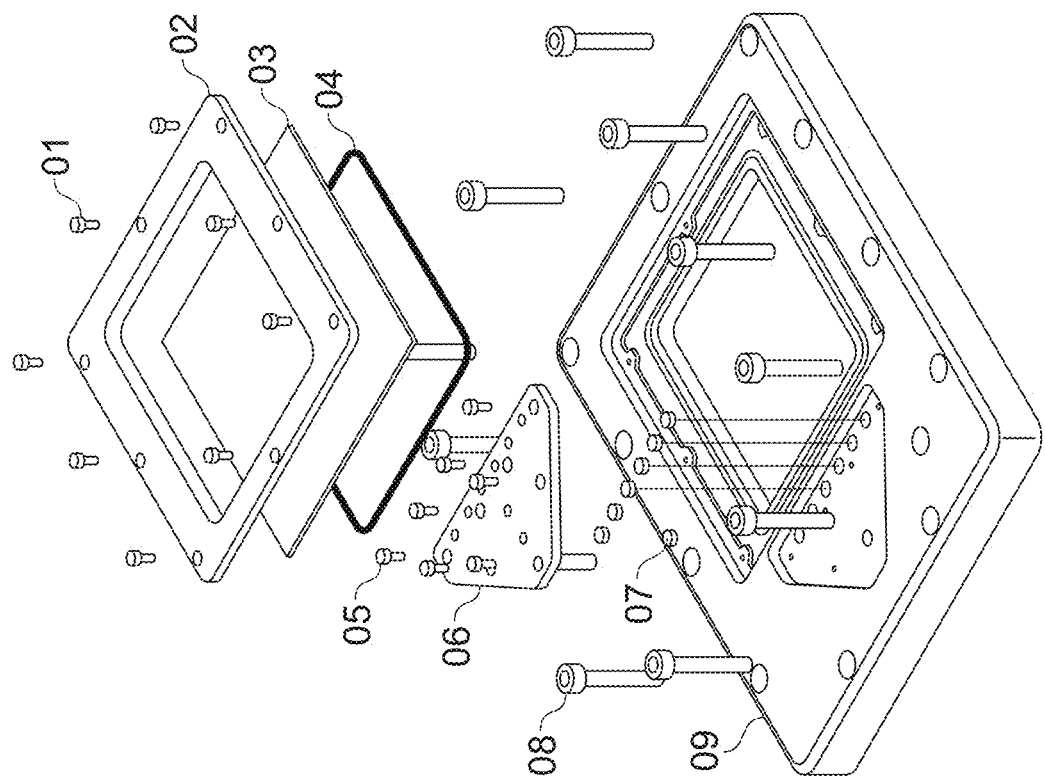
Figure 18

THIN-LAYER CHROMATOGRAPHY SYSTEM AND METHOD FOR ASSESSING ANALYTE CONCENTRATIONS IN SAMPLES

CROSS-REFERENCE TO RELATED APPLICATION(S)

This application is a 35 U.S.C. § 371 national phase filing of International Application No. PCT/EP2018/083050 filed on Nov. 29, 2018, and claims priority to United Kingdom Patent Application No. 1719905.0 filed on Nov. 30, 2017, wherein the disclosures of the foregoing applications are hereby incorporated by reference herein in their respective entireties.

TECHNICAL FIELD

The present invention relates generally to methods and materials for use in therapeutic drug monitoring (TDM).

BACKGROUND ART

One of the major clinical challenges in individualizing a chemotherapy dose regime is that the physician has no information about how the drug is eliminated and metabolized by the patient at the time of administration[1, 2]. The initial dose given to a patient is determined by the patient's body surface area which can then be adjusted due to certain factors [3, 4]. Despite its widespread use, body surface area has been shown to have no correlation with plasma concentration of the drug for most chemotherapies[4]. There can be as large as a 10 fold difference in the plasma concentrations of chemotherapeutics between patients that are given the same body surface area derived dose [5]. Clearance rates can also have a 2 to 10 fold difference between similar patients [6]. These differences in plasma concentration can have significant effects on patient outcomes [7] as well as short-term effects [8].

Therapeutic drug monitoring (TDM) looks to provide information about plasma concentration of the drug to be able to determine elimination and metabolization rates for a specific patient[6, 9]. This information can help the physician adjust the dose regime to achieve plasma concentration levels that are more likely to result in positive clinical outcome while reducing side effects[6, 9].

TDM is used significantly with drugs where there are established relationships between drug concentrations and biological/clinical effects, especially from the following drug categories: antiepileptics/anticonvulsants; antiarrhythmics; immunosuppressants; antibiotics.

One major challenge with TDM is that it is currently a time-consuming process that is both expensive and labour intensive which prevents it from being widely used in a clinical setting[4, 6, 10]. Right now TDM exits primarily in the academic laboratory setting.

Currently, the gold standard method to quantify blood drug concentration is to collect a blood sample from the patient and have a researcher immediately begin the sample preparation process. This involves spinning down the red blood cells followed by extraction of the drugs from the resulting plasma using an organic phase partitioning method and quantifying the drug content using high pressure liquid chromatography (HPLC) techniques[17, 18]. The HPLC equipment requires a high level of maintenance and specialized training to operate reliably. The mechanical complexity of the HPLC equipment comes from many sources including the variable gradients of solvents that are necessary to separate the drug from other metabolites and contaminates in the HPLC column[19]. This requires a complicated system of valves and tubes which require constant maintenance. Although a time-tested method in the laboratory setting, these technical factors prevent the HPLC technique from being widely used in the bedside clinical setting.

TDM holds promise to help physicians individualize chemotherapy drug dosing for patients based on the patient's own unique rate of drug clearance and metabolic degradation.

Without an available TDM method, physicians are currently forced to use entirely observational methods to make dose corrections. Downward adjustments to a first-line chemotherapy treatment are based entirely on observations of the severity of the patient's side effects[4]. However, these cytotoxic drugs have a very narrow therapeutic window[20] where the maximum tolerable dose for that patient and the dose that has therapeutic effect on the tumor are very close. Reducing the dose in an effort to observationally reduce side effects to a tolerable level can actually end up under-dosing the patient which has negative effects on tumor reduction [21].

The tumor size is often evaluated between 6 and 8 weeks after treatment begins [17] to check if the first line chemotherapy is working. If there are signs of tumor progression while on this first-line treatment then the physician will consider switching to a new drug for second and even third or fourth-line treatment[22]. All of these decisions are made without knowledge of how quickly the patient is clearing the drug from their system. It is not known if the drug failed because the patient eliminated it too quickly or if because the tumor is resistant to it. These observational methods have an inherent time delay that can cost precious time allowing the tumor to progress while trying to reach the therapeutic window for an individual patient that does not cause debilitating side effects but can still have therapeutic effects on the tumor.

Thus it can be seen that novel systems of for detecting or quantifying an analyte such as a drug or drug metabolite in a sample of a body fluid from a subject to whom said drug has been administered would provide a contribution to the art not just in the field of chemotherapy, but also in the field of other analyte analysis. In particular, a convenient-to-use TLC system which could be used safely and quickly with samples at the point at which they are obtained or gathered without extensive preparation and training for the user would be of benefit in the art.

DISCLOSURE OF THE INVENTION

The present invention seeks to avoid one or more disadvantages associated with HPLC or other more labour intensive analytical methods while still providing users with a rapid and effective analytical system, for example providing physicians with access to the valuable data on clearance rate and metabolic degradation.

The method is based on thin layer chromatography (TLC) which simplifies the process into a single purpose cartridge.

The basic process of TLC is well known in the art. Typically, a TLC plate is a sheet of glass, metal, or plastic which is coated with a thin layer of a solid adsorbent (usually silica or alumina). A small amount of the mixture to be analysed is spotted near the bottom of this plate. The TLC plate is then placed in a shallow pool of a solvent in a developing chamber so that only the very bottom of the plate is contacted. This eluting liquid (solvent) is the mobile phase, and it slowly rises up the TLC plate by capillary action. As the solvent moves past the spot that was applied, equilibrium is established for each component of the mixture proportioned between the solid adsorbent and the solution. In principle, the components will differ in solubility and in the strength of their adsorption so some components will elute farther up the plate than others. When the solvent is near the top of the plate, the plate is removed from the developing chamber, dried, and the separated components of the mixture are visualized. The ratio of the final position of the spot to the final height of the solvent front is the Rf value. This is a signature of a specific compound and is used to identify the compound.

Using the cartridge of the invention avoids the need for cleaning the system and reduces maintenance. In preferred embodiments the process can be performed at the point of care without extensive training, and can provide 'close to live' data without having in vivo monitoring.

The Examples herein demonstrate the new TLC system can successfully separate chemotherapy agents from their metabolites and other blood components. The Examples herein demonstrate, inter alia, that the technique can resolve between doxorubicin (DOX, a prominent chemotherapeutic), doxorubicinol (DOL, its metabolite) and epirubicin (EPI, an internal standard) from human blood plasma. With the addition of a standard curve, it has been shown that it's possible to quantify the concentrations of each of these chemicals in the sample using CCD camera images and appropriate analysis to quantify the fluorescence intensity of each band.

The present inventors have demonstrated this process using real clinical samples where over 80% of the samples we quantify the plasma drug concentration are within the FDA guidelines of 15% of their HPLC derived values.

However the TLC system has utility beyond quantification of particular drug analytes, as explained below.

Thus in one aspect, there is provided a method for detecting or quantifying an analyte in a sample, the method comprising:
(i) providing said sample;
(ii) preparing an analysis sample from said sample;
(iii) providing a TLC cartridge comprising the TLC plate and a sealed reservoir for the TLC mobile phase;
(iv) loading the analysis sample and one or more reference standards onto the TLC plate of the cartridge;
(v) exposing the TLC plate to the TLC mobile phase to perform TLC on said analysis sample in the TLC cartridge to produce a chromatogram;
(vi) optically analysing analyte and reference standards bands on the chromatogram, with an imaging device to generate optical signals corresponding to the analyte and reference standards;
(vii) detecting or quantifying the analyte in the sample according to said optical signals.
characterised in that the TLC cartridge hermetically seals the TLC mobile phase during loading, performance of the TLC process, and analysis of the chromatogram.

As explained in more detail herein, preferably the reference standards and other functionalities are also incorporated into said TLC cartridge, for example in sealed reservoirs.

The present invention is thus particularly adapted for convenient TLC analysis, for example (but not exclusively) for the purpose of therapeutic drug monitoring, whereby the key elements of the TLC system (including the mobile phase) are integrated into a single cartridge, and wherein vapour release from the mobile phase is avoided during the process. The mobile phase (or solvent system) is the phase that moves along the stationary phase (TLC layer) and separates the sample.

In particular, the loading of the analysis sample onto the TLC plate, development of the plate, and subsequent analysis or quantification of analytes and standards can occur in a sealed environment.

In preferred embodiments the TLC plate uses very small amounts of analyte and is imaged while still 'wet' in situ in the cartridge.

"Hermetically sealed" as used herein means structured to minimise or prevent release of mobile phase vapour from the cartridge prior to, and during, TLC. This is achieved by the use of sealed reservoirs and appropriate septa made of self-sealing materials.

Thus, step (iv) may comprise loading the analysis sample and one or more reference standards onto the TLC plate by penetration through a septum of self-sealing material.

Where the reference standards are also incorporated into said TLC cartridge in sealed reservoirs these may likewise be accessed by penetration through a septum of self-sealing material.

In preferred embodiments once the sample and standards have been loaded, step (v) comprises (in any appropriate order):
(v-1) breaking a barrier between the mobile phase reservoir and the TLC plate to allow fluid access between them;
(v-2) orientating the cartridge to a first orientation, which first orientation permits the base of the plate to be exposed to the released mobile phase solvent and start the TLC process;
(v-3) during or after production of the chromatogram, orientating the cartridge to a second orientation, which second orientation ceases exposure of the base of the plate to the released mobile phase, to stop or slow the TLC process.

Typically, the first orientation is substantially vertical, which is the most common TLC development method. Development can then be stopped when the mobile phase reaches a pre-determined height by step v-3. Typically, the second orientation is therefore substantially flat (horizontal), whereby the mobile phase can flow away, back to the reservoir. This can be used after the process is complete, or simply to slow the TLC process. Steps v-2 and v-3 can be repeated according to the desired development process.

The orientation of the cartridge to permit the base of the plate to be exposed to the released mobile phase solvent can also have an added benefit of ensuring the mobile phase is suitably mixed, which is particular beneficial where is comprises multiple solvent components.

Optionally step (v) further comprises:
(v-4) orientating the cartridge to a third orientation, which third orientation permits the mobile phase solvent to run into an absorbent material present in the cartridge. Typically the third orientation is substantially vertically opposed to the first orientation ("upside down"). Absorption of the mobile phase after use may be beneficial in relation to disposal etc.

Suitable absorbent materials are known in the art—for example universal 'pillow' or 'pad' materials used in commercially available spill kits for organic solvents.

In preferred embodiments the method is used for quantification of the analyte, and includes the steps of:
(vi) optically analysing analyte and reference standards bands on the chromatogram to generate optical signals proportionate to the concentrations of analyte and reference standards;
(vii) converting the optical signals into an analyte concentrations in the sample.

US2011/0239745 relates to the rapid identification of explosives using TLC and colorimetric Techniques. This publication provides some general background to the use of rapid TLC systems.

DE2823476 (A1) relates to a separation chamber for thin-layer chromatography is designed as a stackable cartridge which is preferably pocket-sized and made of plastic.

CN204044122 (U) relates to a multi-component and portable detection device based on thin-layer chromatography for use in the technical field of food safety.

GB1211468 (A) relates to a TLC apparatus purportedly suitable for portable use.

WO2016153980 relates to methods and systems for trace chemical detection 'in the field', especially trace chemical detection using thin layer chromatography. This publication describes a plate carrier-housing for a TLC plate which serves to protect the plate during storage and in the field. Although a mobile phase reservoir may be present, there is no teaching or suggestion of a hermetically sealed cartridge as described herein.

Thus none of these publications describe TLC methods or systems as described herein.

The abstract at http://cordis.europa.eu/project/rcn/193248_en.html proposes highly selective nanoparticle extraction and liquid crystal detection incorporated in microfluidic lab-on-chip device (optofluidics based) allowing the real-time drug monitoring. However, no details are provided in relation to the detection system.

Examples of Cartridge Systems Suitable for Practice of the Invention

One aspect of the present invention provides a TLC cartridge comprising the TLC plate and a sealed reservoir for the TLC mobile phase, characterised in that the TLC cartridge is adapted to hermetically seal the TLC mobile phase during loading, performance of the TLC process, and analysis of the resulting TLC chromatogram.

Figure 10A:
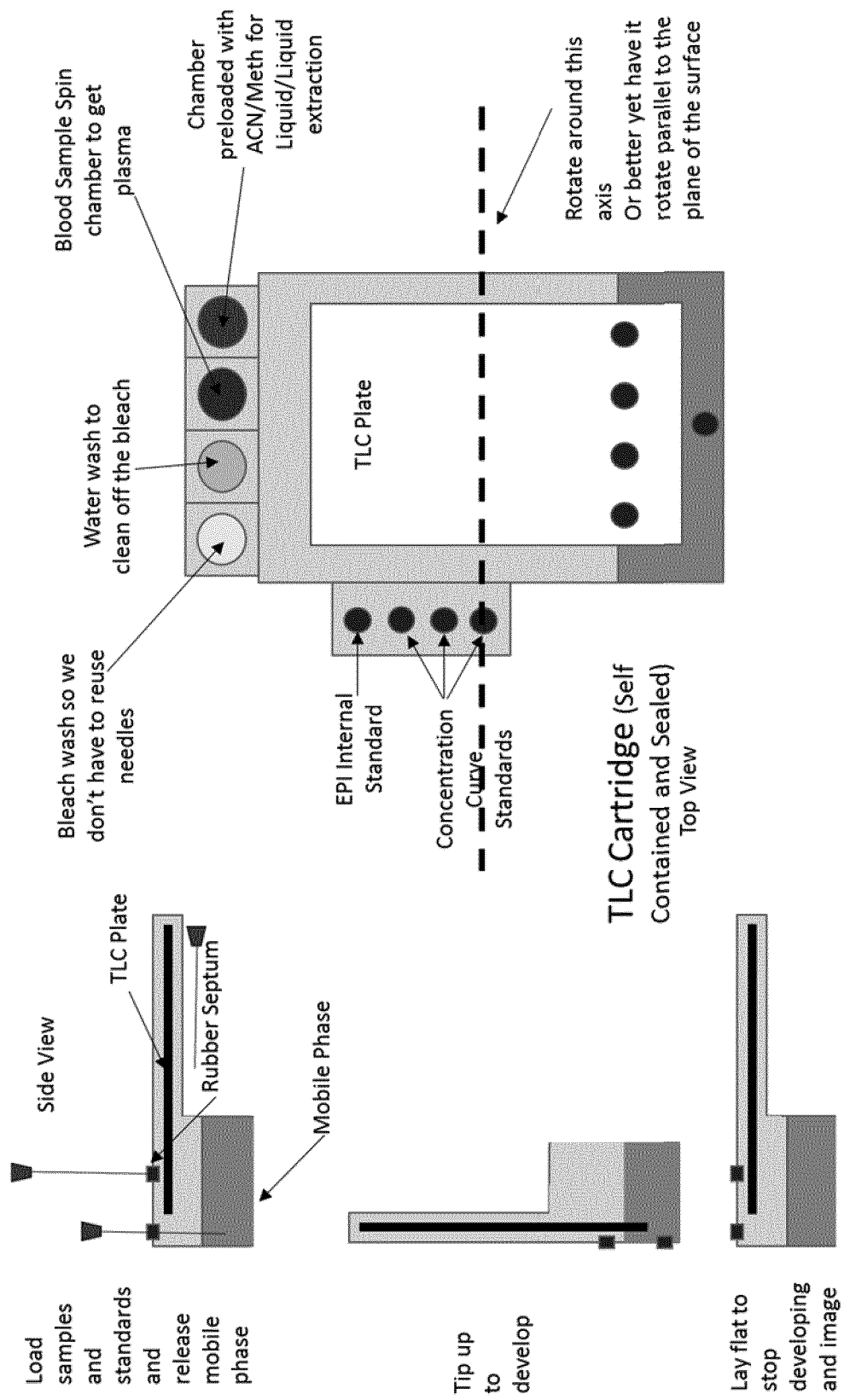
Figure 10B:
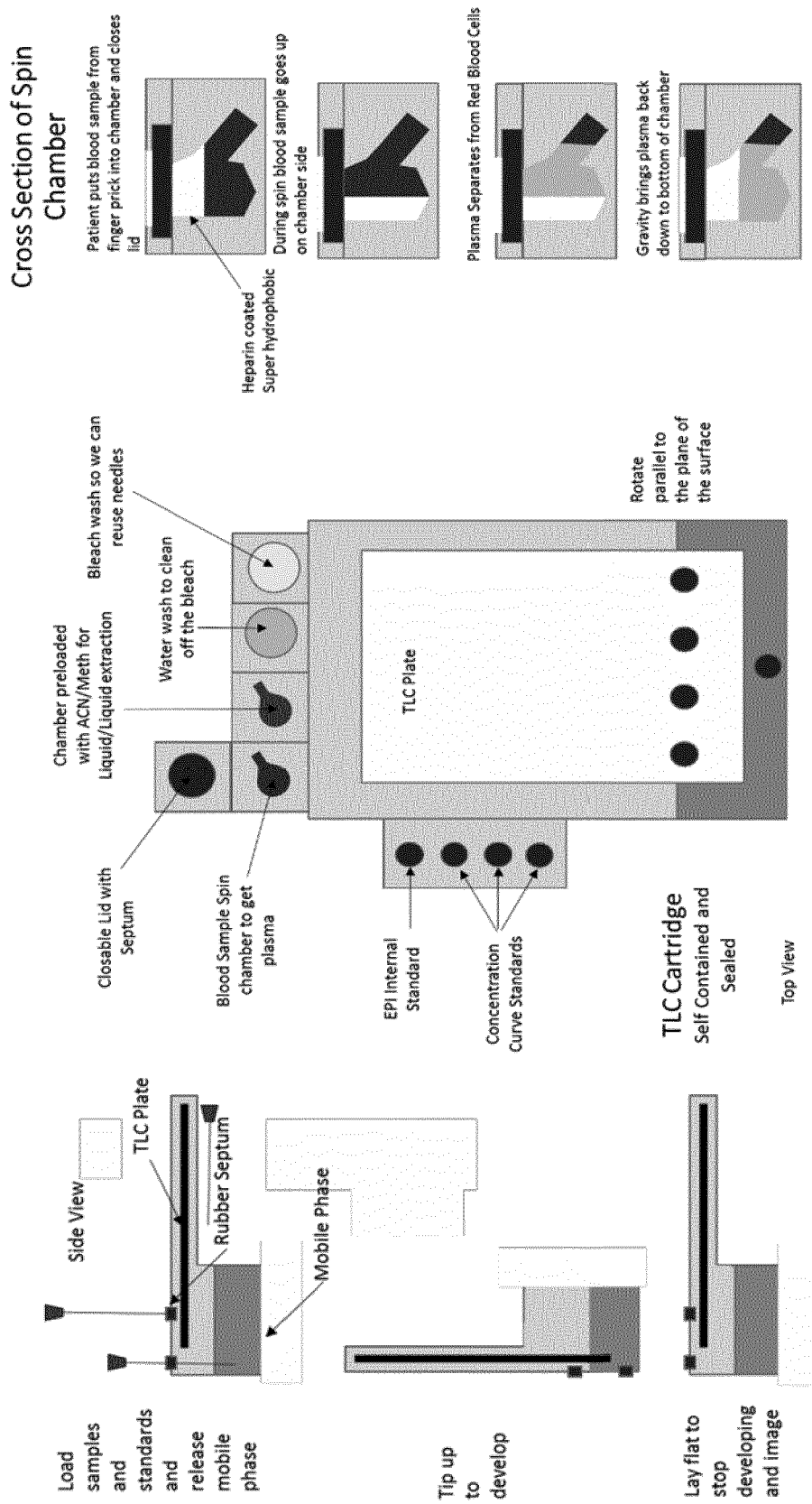
Figure 10C:
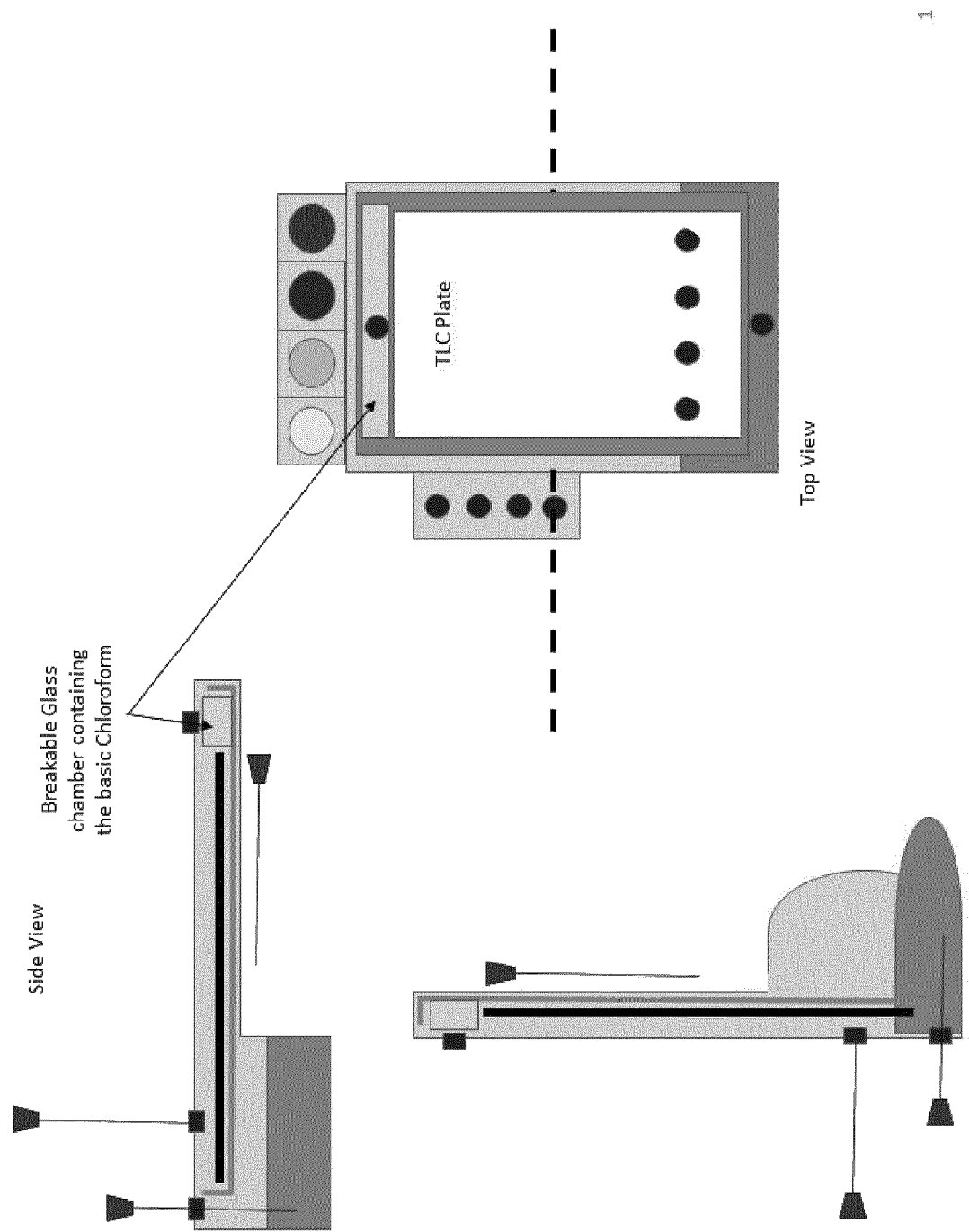
Figure 10D:
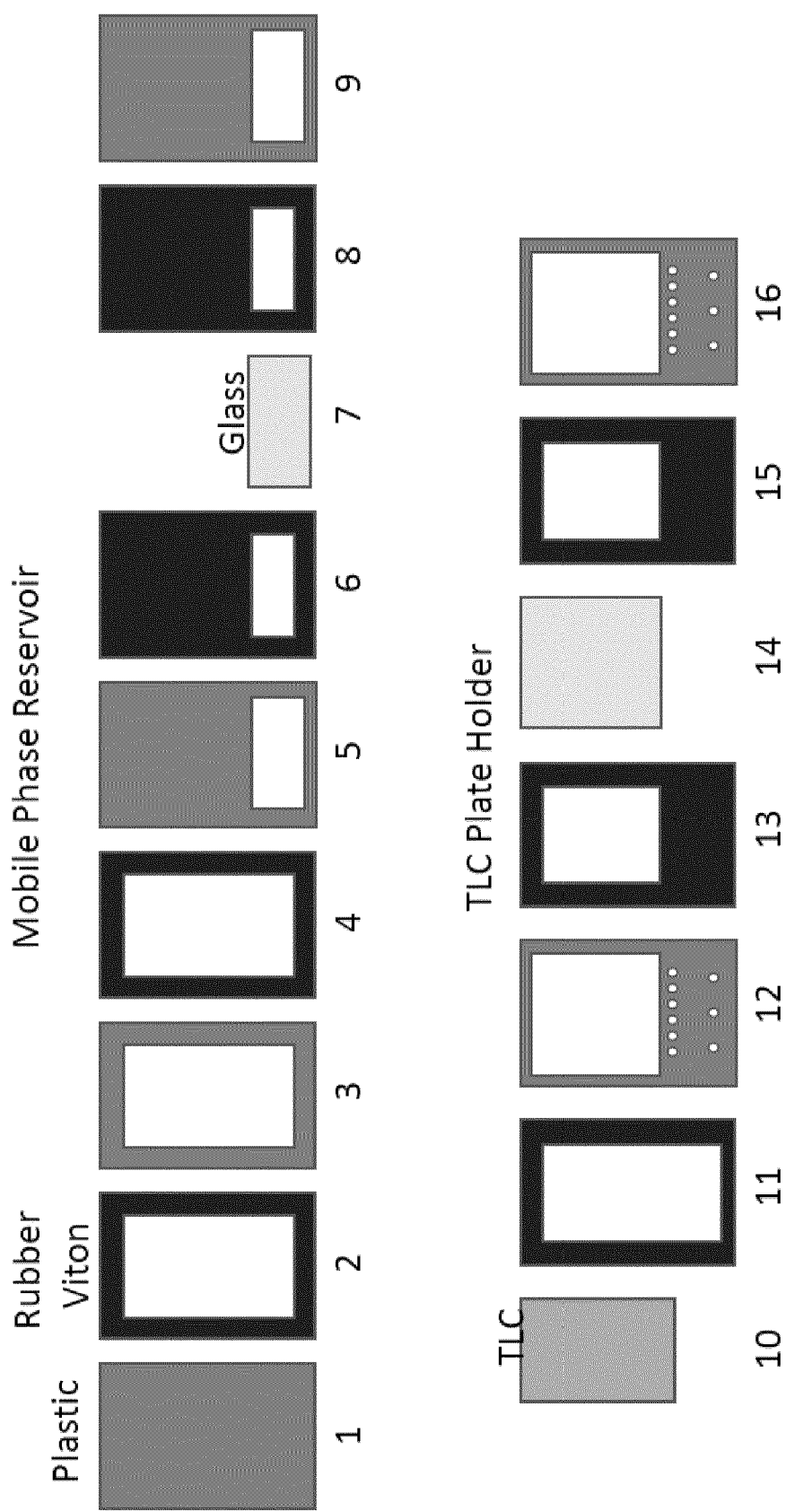

In one embodiment, illustrated (without limitation) in FIG. 10d, the cartridge is composed of a planar (16 layer) design formed from plastic and Viton sheeting with an integrated breakable glass liquid-shield that segregated the mobile phase from the TLC plate prior to elution.

In a further embodiment, illustrated (without limitation) in FIG. 18, there is provided a cartridge comprising:
(i) a face unit incorporating an aperture to view a TLC plate;
(ii) a window covering the aperture in the face unit;
(iii) a rear unit defining a mobile phase reservoir or chamber;
(iv) a TLC plate located between the face unit and the rear unit;
(iv) a breakable barrier between the mobile phase reservoir and the TLC plate to allow fluid access between them.
(v) a plurality of gaskets for collectively sealing at least (a) the mobile phase reservoir; and (b) a volume or chamber defined by the face unit and/or rear unit in which the TLC plate can be exposed to the mobile phase once the mobile phase is released from the reservoir, such as to prevent mobile phase entering the external environment;

wherein:
the face unit further incorporates a plurality a septa of self-sealing material for loading reference standards and/or sample onto respective lanes of the TLC plate; and
the face unit further incorporates a septum of self-sealing material for accessing and breaking the barrier to release the mobile phase from reservoir into the volume or chamber into which the TLC plate can be exposed to the mobile phase.

This primarily bipartite design (based around a moulded, shaped or profiled face unit and base unit) can, in preferred embodiments, be provided and assembled more simply than the multi-layered design. The units can be conveniently screwed together to assemble and position the components, compress the relevant gaskets or o-rings, and retain the septa.

The face and base units can be made of any suitable non-porous (liquid retaining) material—for example metal or plastic e.g. UHMWPE; Polypropylene; Aluminium; PEEK, PTFE etc.

The window can be made of any suitable transparent material—for example glass such as float glass; Quartz; PVC etc.

Likewise the breakable barrier can be made of any suitable non-porous (liquid retaining) material—for example glass, metal or plastic e.g. polypropylene; a foil, such as Aluminium foil; PTFE foil; PEEK etc.

The O-rings (or gaskets) and septa are used to hermetically seal different fluid or vapour holding volumes of the cartridge as shown. Suitable materials include elastomeric materials such as PTFE, FKM, FFKM, ETP etc.

In some embodiments this cartridge further comprises a window gasket which is compressed between the window and the face unit by an outer window sealing plate mountable on the face unit, optionally be means of a plurality of screws.

In some embodiments of this cartridge, the septa of self-sealing material to allow loading reference standards and/or sample onto respective lanes of the TLC plate are held between the face unit and an injection plate, wherein the face unit and injection plate incorporate corresponding apertures to permit said loading of the TLC plate.

In some embodiments of this cartridge, the cartridge comprises a rotatable paddle for breaking the barrier to release the mobile phase from reservoir into the volume in which the TLC plate can be exposed to the mobile phase, wherein in use the paddle is actuated by penetrating the septum of self-sealing material, which permits access to the barrier, for example with a needle, and then rotating the paddle through the barrier.

The dimensions of the cartridge can be adapted for the purpose for which it is intended, including the number of samples or standards which it is intended to run. However typically the cartridge will be relatively small and portable. For example the TLC plate may be around 50 to 100 mm wide, and 75 and 150 mm long. The cartridge will be dimensioned accordingly e.g. less than 300, preferably less than 250, 200, or 150 mm long, and less than 200 mm, preferably less than 150, 125 or 100 mm wide. The depth must be sufficient to accommodate the reservoir and plate, but will preferably less than 60, 50, or 40 mm deep. It will be appreciated that any combination of these dimensional limitations can be combined to define the overall dimensions of the plate or cartridge.

Preparing the Cartridge

In another aspect there is provided a process for preparing a cartridge of the invention, the process comprising providing:
  (i) a face unit incorporating an aperture to view a TLC plate;
  (ii) a window for covering the aperture in the face unit;
  (iii) a rear unit defining a mobile phase reservoir;
  (iv) a TLC plate;
  (v) a breakable barrier between the mobile phase reservoir and the TLC plate to allow fluid access between them.
  (vi) a plurality of gaskets for collectively sealing at least (a) the mobile phase reservoir; and (b) a volume defined by the face unit and/or rear unit in which the TLC plate can be exposed to the mobile phase once the mobile phase is released from the reservoir, such as to prevent mobile phase entering the external environment;
  (vii) a plurality of a septa of self-sealing material for incorporating into the face unit for loading reference standards and/or sample onto respective lanes of the TLC plate; and
  (viii) a further septum of self-sealing material for incorporating into the face unit for accessing and breaking the barrier to release the mobile phase from reservoir into the volume into which the TLC plate can be exposed to the mobile phase;
  (ix) a mobile phase
    assembling (i) to (viii) into a cartridge which hermetically seals the TLC mobile phase (iv) during loading, performance of the TLC process, and analysis of the resulting TLC chromatogram.

The cartridge may also comprise the window gasket and outer window sealing plate, the injection plate, and/or the rotatable paddle described above, which can be assembled with the other components.

Cartridges of the present invention may optionally be provided already comprising mobile phase in the reservoir.

Samples and Sample Preparation

The cartridge system of the invention has utility in many technical fields, and the sample may be any desired where the analyte can be separated from contaminants or background via TLC. For example, the sample can be an environmental sample, chemical synthesis samples, body fluid and so on.

Where required the sample preparation of step (ii) may comprise removal of particulate or higher density material from the original source sample. Such material may otherwise degrade the performance of the TLC. Preferably this is achieved by one or more precipitation, filtration or centrifugation steps such as are known in the art. As explained in more detail below, the cartridge may be adapted to include an asymmetric well for sample centrifugation, which sample preparation well includes a side region adapted to trap or retain particulate or higher density material directed into the side region by centrifugation. The prepared sample can then be removed from the main body of the well.

Preferably the analyte is a drug or drug metabolite, and the sample is a body fluid from a subject to whom said drug has been administered, the method comprising:
  (i) providing said sample of body fluid;
  (ii) preparing said sample of body fluid to form an analysis sample.

As used anywhere herein, unless context demands otherwise, the term 'body fluid' may be taken to mean any fluid found in the body of which a sample can be taken for analysis. Examples of body fluids suitable for use in the present invention include, but are not limited to blood, urine, sweat and saliva.

In a preferred embodiment of the present invention the body fluid is blood.

In order to utilise the system of the invention with a blood sample, the red blood cells must be removed, and the protein precipitated from the plasma to form the analysis sample.

In a preferred embodiment the red blood cells are removed by centrifugation, although in other embodiments clotting (e.g. with thrombin) or blood separation membranes (see e.g Liu, Changchun, et al. "Membrane-based, sedimentation-assisted plasma separator for point-of-care applications." *Analytical chemistry* 85.21 (2013): 10463.) may be used.

In a preferred embodiment the protein is precipitated, preferably in a single step, and removed by centrifugation. Precipitants are well known in the art e.g. acetonitrile:methanol (2:1) (v:v)—see e.g. Polson, Cara, et al. "Optimization of protein precipitation based upon effectiveness of protein removal and ionization effect in liquid chromatography—tandem mass spectrometry." Journal of Chromatography B 785.2 (2003): 263-275.

Proceeding in this way avoids the use of a drying step followed by resuspension in secondary solvents as used in many traditional TLC protocols.

Thus, the present invention has the advantage that the body fluid, particularly blood sample processing, and\or TLC can take place in a self-contained cartridge at point of care.

Furthermore, automation of the cartridge handling allows the process to be safely performed in a clinical setting with minimal interaction from clinical staff.

In an alternative embodiment, a body fluid sample may be directly 'spiked' with a drug, for example to study its ex vivo degradation in that fluid.

Use of Reference Standards

As explained above, the TLC is performed using one or more reference standards corresponding to the analyte or analytes (or internal standard, see below) at specified concentrations which are incorporated into the TLC cartridge, thereby in effect giving each TLC cartridge its own 'standard curve' to allow optical signals into an analyte concentrations in the sample.

Preferably the one or more reference standards or internal standards are held in the cartridge in sealed reservoirs. As explained above, these may likewise be accessed by penetration through a septum of self-sealing material.

Use of Internal Standard

In one embodiment an internal standard is introduced or "spiked" into the analysis sample. Preferably this internal standard is closely structurally related to the analyte (e.g. drug or drug metabolite).

The difference between the recovered or quantified amount and the known amount of internal standard can be used to scale the analyte concentration values to account for variability in the extraction efficiency as well as any artefacts in the optical imaging.

Use of pH Manipulation

In some contexts it may be desirable to quantify not only a drug analyte, but also (or alternatively) its metabolites in vivo, since this can help to probe pharmacokinetic differences between patients. However frequently a drug and its closely structurally related metabolites may be hard to distinguish by their fluorescent properties under the same conditions on the same TLC plate.

In one embodiment, following stages (v) and (vi), the pH of the plate environment may be adjusted, and the optical analysis of stage (vi) repeated at this new pH. This may be used to enhance differentiation between similar compounds via the pH-induced bathochromic shift in the emission spectra.

The present inventors have demonstrated such pH-mediated fluorescence spectroscopy for therapeutic drug monitoring in complex media for the simultaneous quantification of the chemotherapeutic prodrug Irinotecan and its active metabolite SN-38 from human plasma across the clinically relevant concentration range, i.e. from micromolar to nanomolar at molar ratios of up to 30:1.

In one embodiment the cartridge comprises a sealed reservoir for a pH modifying agent e.g. buffer or solvent. In use, at the appropriate time, a barrier between the pH modifying agent and TLC plate is broken to allow fluid access between them, such that the pH of the plate (or at least the developed portion of the plate) is adjusted.

Application of Sample to Plate

In the performance of the invention a spotting device such as a syringe or micropipette is generally used to deliver a fixed volume of sample or reference as a spot or streak at the starting point or line of the TLC layer.

Preferably the TLC plate will comprise at least 4 lanes i.e.
A lane for the sample;
3 lanes for concentrations of reference standards/internal standard.

More preferably the TLC plate will comprise at least 5 lanes i.e.
A lane for the sample;
4 lanes for concentrations of reference standards/internal standard.

More preferably the TLC plate will comprise at least 6 lanes i.e.
2 lanes for different sample concentrations;
4 lanes for concentrations of reference standards/internal standard.

As explained above, the each lane or potential lane may be aligned with a corresponding hermetically sealed access point for spotting or otherwise applying the prepared sample or standards, for example a pierceable septum.

Imaging and Analysis

The optical analysis in step (vi) generates optical signals proportionate to the concentrations of analyte and reference standards on the developed chromatogram.

Typically this is done with a TLC plate reader, although any imaging system which produces an image capable of manipulation in step vi) may be used e.g. a digital camera, a smartphone, a flatbed scanner, tablet computer and so on.

A TLC plate reader is a device which scans the chromatogram with a beam of light of a specified wavelength in order to measure the absorption or fluorescence of UV or visible light, thus allowing quantitative analysis of the separated compounds.

More specifically, the reader may comprise (or be used with) a light source such as an LED, light from which illuminates the plate. The reflected image of the plate may be detected and digitised, then analysed by a CPU and converted to a result which can be displayed on an LCD screen or other display technology (or output via a conventional interface to further storage or analytical means, for example a mobile device). A light-dependent resistor, phototransistor, photodiode, CCD or other photo sensor may be used to measure the amount of reflected light. The result may be displayed as positive or negative for a particular analyte of interest or, preferably, the concentration of the particular analyte may be displayed. More specifically the conventional reader comprises: illuminating means for illuminating the plate; photosensitive detector means for detecting the intensity of light from the illuminating means which is reflected from the plate; means, coupled to the output of the photosensitive detector means, for representing the intensity of the detected light by a data array; memory means for storing preset data; first data processing means, coupled to the memory means and to the output of the means for representing the intensity of the detected light by a data array, for segmenting the data array according to the preset data into control data, background data and test data; second data processing means, coupled to the first data processing means, for determining whether the test data exhibits a statistically significant result; and output means, coupled to the output of the second data processing means, for outputting the results from the second data processing means.

The reader will analyse a plurality of spatially distinct detection bands pertaining to the analyte and standards. The photosensitive detector means (e.g. light dependent resistor, phototransistor, photodiode, CCD or other light sensor) will therefore detect reflected light from all of these (optionally scanning them) and generate a discrete or segmented data stream for each zone.

The colour of the LED or other source may vary dependent on the label or method of detecting the analyte.

In preferred embodiments a CCD camera is used to image the plate.

In preferred embodiments, as appropriate to the analyte, the fluorescence of the zones on the plate is assessed using a suitable excitation source and imaging device—all of these embodiments constitute possible "optical analysis".

Software may be used to quantify the fluorescence intensity of each band (for fluorescent analytes).

That quantified image intensity is then compared to the standard curve to make an analyte concentration estimate, optionally scaled according to the internal standard.

In the Examples described herein, a custom software based quantification technique was used to determine the plasma concentration of the drug based on the bands, and this is described in more detail hereinafter. In those Examples, the intensity values determined for the DOX and DOL bands in the 3× sample lane were compared to the calibration curve generated using the 0.1 and 0.05 μM concentrations of DOX and DOL. These values were then scaled by the difference in the measured and expected results of the EPI internal standard concentration Additional Properties of the Cartridge As explained in the foregoing, one aspect of the present invention is a self-contained TLC cartridge that hermetically seals the TLC plate and TLC mobile phase.

The cartridge comprises a casing which seals and provides the various functionalities provided by the cartridge. The casing may also provide insulation.

Closures for use in the present invention will typically be pierceable septa which are self-sealing such as to avoid gas-exchange between the plate and the environment.

Preferably closures are utilised which preferably meet USP <381> Type I requirements for elastomeric closures, for example utilising synthetic polyisoprene compounds. Such materials are widely commercially available—see e.g. Parker Hannifin Corporation Medical Systems Division.

The cartridge prevents release of the mobile phase solvent or solvent fumes. It can further prevent release of silica dust or the like from the TLC stationary phase.

A typical mobile phase for use in the present invention may comprise one or more of the solvents chloroform, methanol, acetic acid, and water.

For example one such phase may be: chloroform:methanol:aceticacid:water (80:20:14:6) (v:v:v:v).

In the cartridge the mobile phase is kept separate from the TLC plate until use. In one embodiment a breakable barrier is used e.g. a thin glass barrier, or tearable foil. Breakable (barrier) in this context is used in its art-recognisable sense to mean breachable, preferably irreversibly.

Once the sample and standards have been loaded, the barrier is broken and the cartridge oriented appropriately to expose the plate to the solvent and start the TLC process.

The reference standards (including, optionally, the internal standard) may be incorporated into said TLC cartridge. These may be any of the drugs or other analytes described herein.

The reference standards may be incorporated into separate volumes or wells in the cartridge, which are then applied to the TLC plate prior to exposure to the mobile phase.

This application may be manual e.g. via rubber septa positioned over the plate, or may be automated or semi-automated e.g. via rotation of the wells or volumes to position them over the plate and release the standards.

If an absorbent material is used to absorb the mobile phase after use, this can be the same or similar to absorbent materials used in commercially available spill kits for organic solvents.

The cartridge of the present invention may optionally comprise further functionalities as follows:
(i) a well for blood cell centrifugation, or other removal of RBCs, to generate a plasma sample;
(ii) a well for protein precipitation and\or centrifugation;
(iii) one or more wells for syringe cleaning e.g. bleach and bleach wash.

Protocols for Use of the Cartridge

In use, the TLC cartridge may be employed, for example, using the following simple protocol:

1 Load the analysis sample and references onto the TLC plate using a hypodermic needle to penetrate through the rubber septa.

2 Use the hypodermic needle to break the breakable barrier (e.g. glass coverslip) separating the two chambers or volumes (mobile phase, plate).

3 Tip up the cartridge to let the mobile phase flow into the TLC chamber and come into contact with the bottom of the TLC plate allowing the plate to develop normally by capillary forces.

4 Tip the cartridge back down to a flat orientation to stop the TLC plate development by allowing the mobile phase to drain back into the second chamber.

In this flat orientation the TLC plate can be imaged using a plate reader or other desired imaging system.

Automation of Sample Preparation and/or Other Steps

One or more aspects of the analysis sample preparation may be automated and\or integrated into the cartridge as described herein.

Specifically, the invention also provides a companion fluid handling device which comprises:
(i) centrifuge (e.g. microcentrifuge) for centrifugation of the cartridge for separation of RBCs and\or protein precipitant in wells or volumes within said cartridge;
(ii) a cartridge holder designed to receive said cartridge and keep it firmly held during centrifugation;
(iii) optionally a tiltable stage for altering the orientation of the cartridge to perform the centrifugation, the TLC process, and optionally reading the plate.

These elements may be combined into a housing. The housing may be transparent for ease of use.

POC testing devices which contain (micro)centrifuge components are known, albeit in different contexts to the present invention—see e.g. references [30] (Papu et al) and [31] (Drucker) below.

Centrifuge well-mouldings to accommodate the cartridges may also be readily prepared by injection moulding or 3-D printing, according to methods well known in the art.

Figure 12:
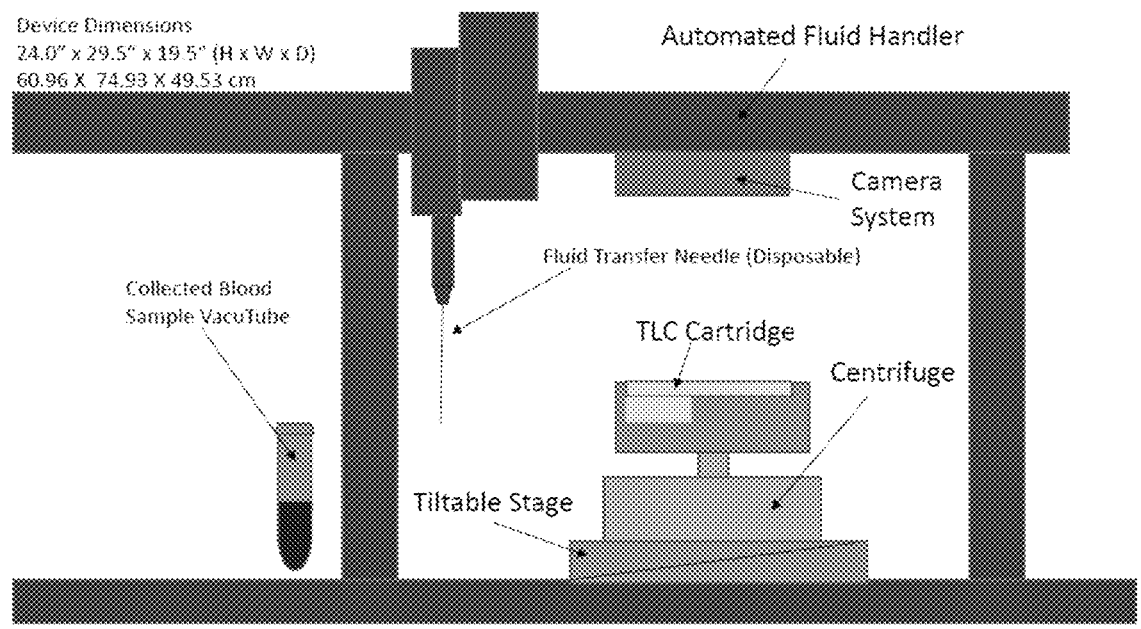

FIG. 12 illustrates an automated system which can perform the mechanical manipulation of the cartridge and the fluid handling required in the first step of the protocol as well as developing the TLC plate.

Use of this automated system comprises both manual and automated steps:

Manual Process:
  Manually load blood sample, TLC Cartridge
  Manually discard blood sample, TLC Cartridge
Automated Process:
  Transfer collected blood sample to centrifuge tube to spin plasma;
  Transfer Plasma to Liquid/Liquid extraction centrifuge tube preloaded with ACN/Methanol;
  Aspirate to mix well;
  Spin down protein precipitant;
  Transfer the liquid/liquid extraction fluid to the TLC Plate;
  Transfer standards to TLC Plate;
  Develop plate by tipping upright;
  Move TLC plate into TLC plate reader;
  Read Plate.

One or more aspects of the plate reading, image analysis, and concentration derivation may be automated, and optionally integrated into the fluid handling stage as described herein.

Specifically, the invention also provides a companion TLC reader and data processor which comprises:
(i) a light/excitation source, for example UV lamp, LED, or laser;
(ii) a CCD device or other suitable device for imaging;
(iii) a data processor for processing the image and converting the optical signals into an analyte concentrations in the sample, which typically will be computer implemented.

One or more of these elements may be combined into a housing with the fluid handling device, oriented appropriately for reading the plate on the cartridge present on the cartridge holder once the TLC chromatogram is developed. The housing may also include other functionalities e.g. for receiving hypodermic needles or collected body fluid samples.

Optionally the data processor for processing the image and converting the optical signals into an analyte concentrations in the sample may be a separate entity, and may be constituted by a mobile device with suitable application. US publication 2014/0080129, incorporated herein by reference, is reported to utilise conventional TLC systems but use of a smartphone for analyzing the results of the test.

Analysis of Bands & Quantitation

As explained herein, the system may incorporate specific image processing to facilitate analysis of the zones or bands (the terms are used interchangeably) on the TLC layer where one or more sample or reference components are located.

The invention comprises optically analysing analyte and reference standards bands on the chromatogram with a TLC plate reader to generate optical signals corresponding to the analyte and reference standards. These optical signals can be derived from the TLC plate image by defining the imaging area of the band representing the analyte or standard in terms of pixels of varying intensity differing from the 'background' pixel intensity of the plate where the analyte or standard is not present.

Band image processing may comprise (taking an analyte by way of example):
(i) recognising analyte signals from background;
(ii) identifying representative signal for each analyte;
(iii) identifying the full area and signal for each analyte;
(iv) measuring the intensity of each analyte area;

More specifically an algorithm may be used for quantitative comparison of sample with internal standard. This may be used to 'flatten' the background created by the lighting source, define the physical dimensions of band by edge detection, and calculate the area of the band. Finally the curve defined by each line of pixels in the band may be added together to produce a total intensity for the fluorescence band.

In one embodiment the algorithm is characterised by one of more of the following:
Requesting the user to identify the general area of the band, for example by use of a user interface which permits a rectangle or similar to be defined around the general area of the image.
The algorithm handles each vertical line of pixels defined by an X value separately from one another. This prevents unknown variations as we move across the image in the X direction from causing inaccuracies as we correct the Y direction.
The algorithm accounts for background differences across the line of pixels by flattening the signal to get rid of variations from the plate itself and from inhomogeneous lighting. This is individualized for each line of Y pixels.
The algorithm does not analyse the entire band. It only analyses a predetermined region of the band starting from the centre where it is brightest and moving up and down from there to a level that is predetermined. This prevents noise from interfering with the boundaries of the defined band. The entire area under that portion of the signal curve is calculated, all the way down to y=0. This approach automatically adjusts the boundaries of the band to best fit the concentration of drug in the band. Bands with a high concentration tend to spread out more than bands that have less drug but do so in a proportional way. By being consistent in defining the boundaries of the band in this way we account for this proportionality in the integration.
Only areas under the curve where the peak value is above a certain predetermined threshold are counted.
All the independently derived areas under the curve are added together to yield a total integrated intensity value.
Because the program, not the user, defines the boundaries or edges of the band that keep it above the noise floor, it can be applied objectively from band to band without influence from the user.

Thus, in embodiments of the invention steps (v) and vii) may comprise:
(a) optically analysing analyte and reference standards bands on the chromatogram to generate providing an image of the TLC plate including said band;
(b) determining an intensity of the portion of the image representing the band;
(c) determining the concentration of the compound represented the band using the determined intensity.

Steps (b) and (c) may be performed as described above, using boundary definition and then summation of pixel intensities within a defined area.

Thus, step (b) may include:
(b-1) receiving an input identifying an approximate region of the image, the approximate region including the band;
(b-2) identifying the boundaries of the band;
(b-3) determining the intensity of the band based on the intensities of a plurality of pixels located within the boundaries of the band.

The actual quantifying of the analyte may then be achieved by comparing the determined intensity with a calibration curve representing a relationship between the determined intensity and the concentration of the compound.

Step (a) may include receiving the image from a suitable imaging device such as a dedicated TLC plate reader, a digital camera, a smartphone, a flatbed scanner, tablet computer and so on.

The practice of the invention may include the step of converting the image into black and white, or grayscale. The system may further including the step of inverting the colours in the image, so that the portions of the image representing the band have a higher intensity than the portions of the image representing the background.

Drug Analytes

As explained above, the methods and systems of the invention have particular utility for quantifying an analyte which is a drug or drug metabolite in a sample of a body fluid such as blood. This may be used for the purpose of therapeutic drug monitoring (TDM) as described in more detail below. Such may involve quantifying both the drug and\or its metabolites.

As explained in the Examples herein, the present invention opens up new utilities for POC TDM analysis of new and existing classes of drugs beneficially subject to TDM.

Preferred drugs suitable for TDM are those which have large between-subject (metabolic) variability; small therapeutic index; an established concentration—effect (or toxicity) relationship (or both); and a therapeutic response which is either delayed or not readily monitored.

In one preferred embodiment the drug is a chemotherapeutic. Non-limiting examples of chemotherapeutics include mTOR inhibitors, 5-flourouracil, imatinib, EGF receptor inhibitors, platinum based agents, etopisode, doxorubicin and suramin.

In other embodiments the drug may be selected from the class consisting of: antiepileptics, antiarrhythmics, antibiotics, antifungals, immunosuppressants, dermal medicine and chemotherapy.

Other classes of drugs which may be advantageously monitored include: bronchodilators, and psychoactive drugs.

Preferred examples of drugs suitable for quantifying according to the present invention are set out in Table D in the Examples hereinafter. However, it will be appreciated that this Table is non-limiting. For example, Paclitaxel (brand name: Taxol) and Bleomycin are two strongly fluorescent chemotherapeutics to which the invention may be applied.

Preferred drugs for use in the present invention will be natively fluorescent drugs.

However, the TLC systems of the invention may also be applied to non-natively fluorescent drugs, for example non-fluorescent compounds may be quantified by absorbance or fluorescence quenching. TLC layers are commercially available that contain a fluorescence indicator, so that UV-active analytes or standards in the sample extinguish (quench) the fluorescence and appear as dark spots on a bright background. Examples include TLC silica gel 60G plates which can be obtained coated with fluorescent indicator F254.

An example of a drug that absorbs strongly in the visible region is nitrofurantoin, an antibiotic.

Alternatively, if desired, non-natively fluorescent drugs may be fluorescently labelled prior to detection using conventional fluorescent tags known in the art.

Utility of Drug Analysis

As explained above, the methods and systems of the invention have particular utility for quantifying an analyte which is a drug or drug metabolite in a sample of a body fluid such as blood. Typically the sample is taken at a set time ("T") after administration and its concentration is quantified.

A primary utility for this system is TDM of the drug and\or its metabolites.

However, the invention may be used more generally to measure and monitor the pharmacokinetics or pharmacodynamics ("PK/PD") of drugs, by making frequent assessments at the point of care.

This information may in turn provide information about drug clearance rate and metabolic degradation.

This data can be used therapeutically to help physicians make adjustments to dosage regimens e.g. in chemotherapy, before observational data of side effects or therapeutic benefit is available.

The data can also be used in designing or performing clinical trials e.g. in choosing which drugs to trial or when designing the format of the trial.

The invention has particular utility where it is believed or assessed that the subject, or subject group, is in need of TDM, for example due to suspected drug interactions; suspected drug adverse effects/toxicity; suspected drug abuse; unexplained failure of therapy; and suspected non-compliance.

For this latter utility (compliance) actual quantification may not be required, although that is still preferably to ensure appropriate dosages have been administered, or self-administered.

Systems and Kits

The systems or kits of the present invention may thus provide one or more of:
(i) a self-contained TLC cartridge that hermetically seals the TLC plate and TLC mobile phase;
(ii) a TLC plate reader adapted to read the bands on the plate in said cartridge;
(iii) a data processor for converting the optical signals from the reader into an analyte concentrations;
(iv) a microcentrifuge for blood sample preparation, optionally adapted to seat the cartridge, or alternatively to be used directly on a receptacle for said sample;
(v) a hypodermic needle for transferring solutions;
(vi) if required, a separate lancet or other convention means for obtaining a small volume blood sample;
(vii) instructions for use according to the methods of the present invention.

Also provided are kits of parts comprising the elements of the cartridge itself.

Other elements which may be optionally included are a fan, and a timer.

"And/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

FIGURES

FIG. 1—Separation of EPI, DOX, and DOL on the TLC plate.

Figure 2:
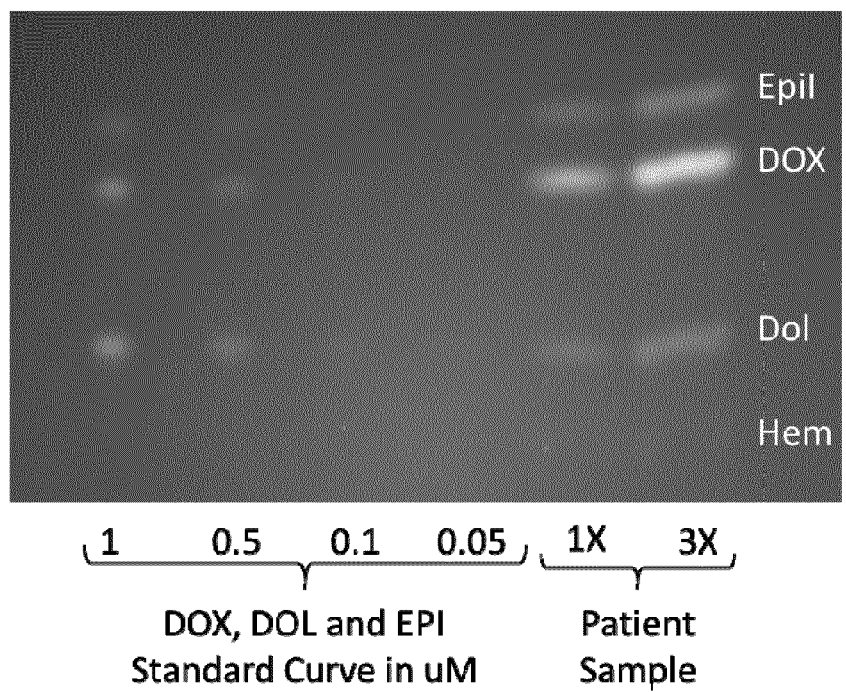

FIG. 2—Separation of EPI, DOX, and DOL from spiked samples of healthy human plasma.

Figure 3:
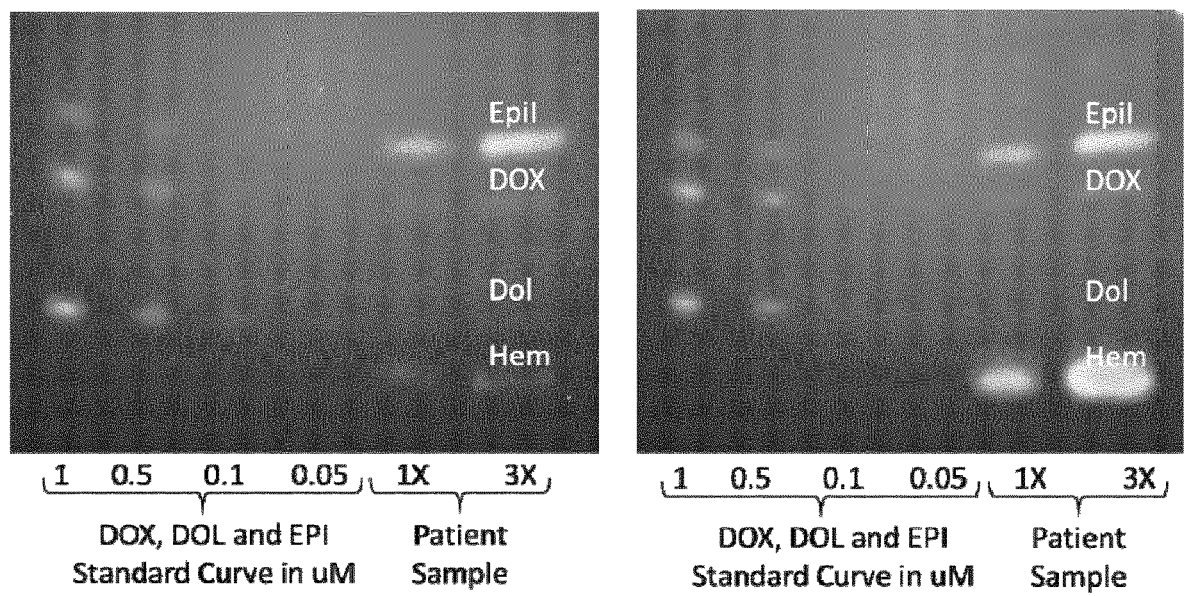

FIG. 3—Separation of EPI, DOX and DOL from clinical samples of two different cancer patients undergoing DOX treatment (Patient 1, left; Patient 2, right).

Figure 4:
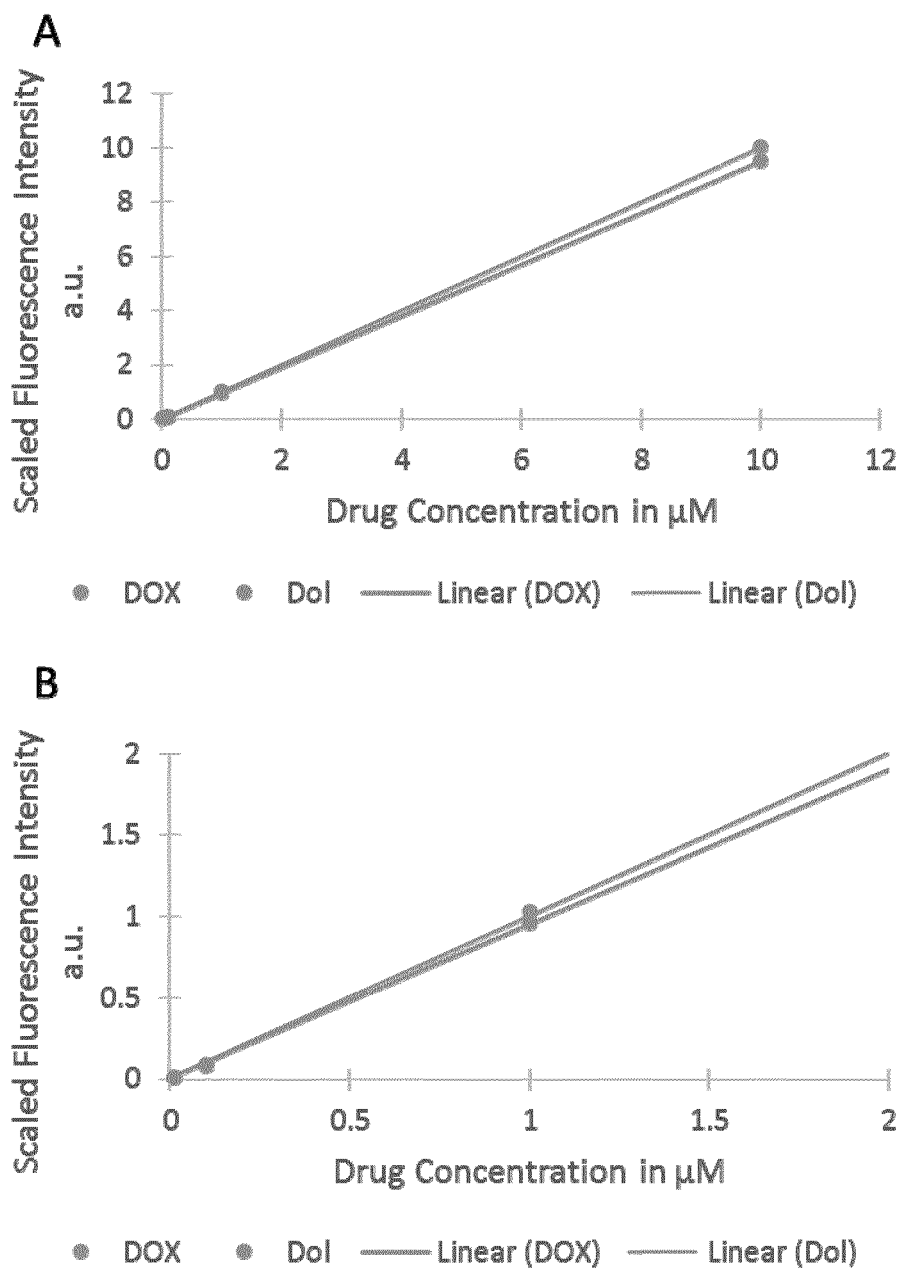

FIG. 4—Linearity of the optical quantification of DOX and DOL. B Graph showing the measured fluorescence intensity versus concentration for DOX and DOL concentrations ranging from 0.01 to 10 µM. B. Zoomed in view of panel A showing data points at the lower concentration range.

Figure 5:
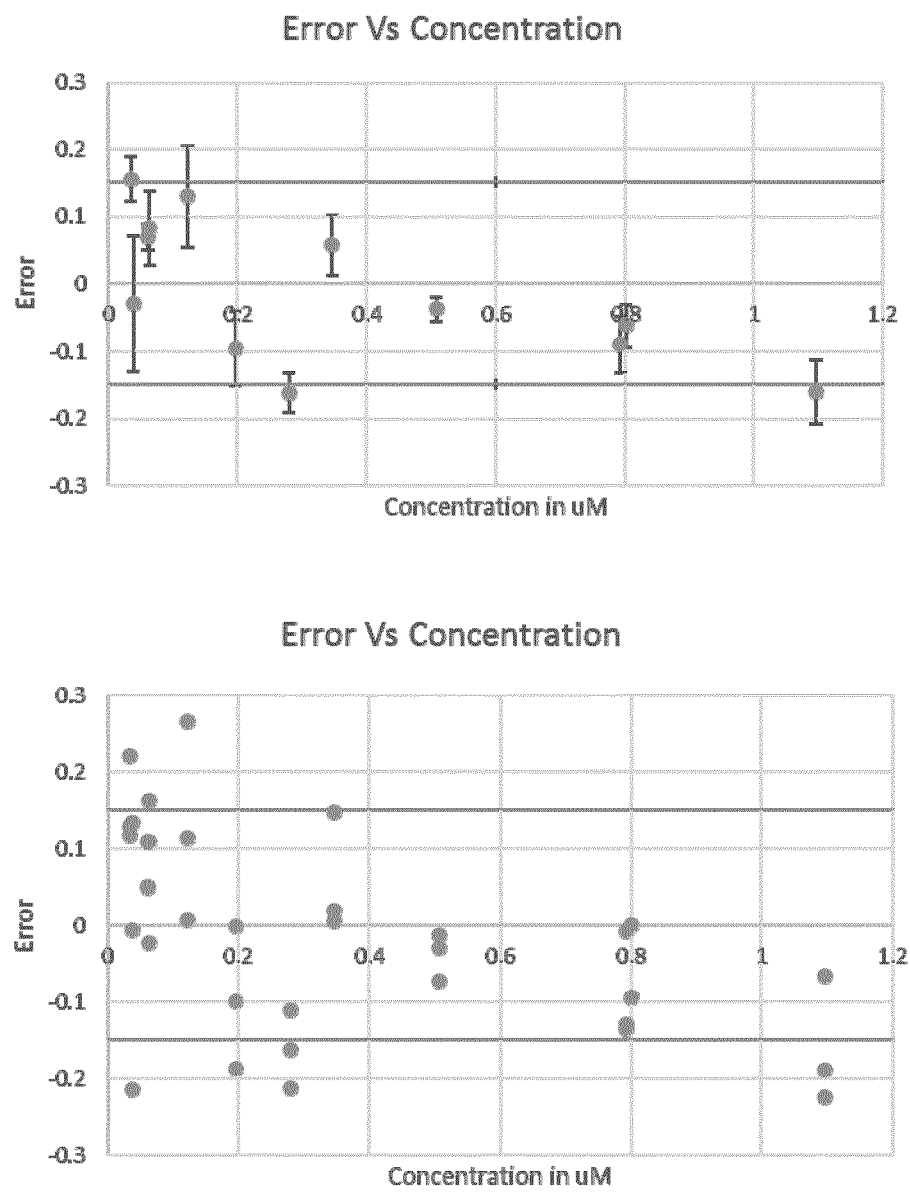

FIG. 5—Quantification of DOX and comparisons to HPLC derived values. A Average values with errors bars showing standard error of the mean (n=3). The ±15% error range allowed the by FDA for a bioanalytical method is shown by the blue lines. B All the data points are shown FIG. 6—Quantification of DOL and comparisons to HPLC derived values. A Average values with errors bars showing standard error of the mean (n=3). The ±15% error range allowed the by FDA for a bioanalytical method is shown by the blue lines. B All the data points are shown FIG. 7—Quantification of Irinotecan and comparisons to HPLC derived values. A Average values with errors bars showing standard error of the mean (n=2). The ±15% error range allowed the by FDA for a bioanalytical method is shown by the blue lines. B All the data points are shown.

Figure 8:
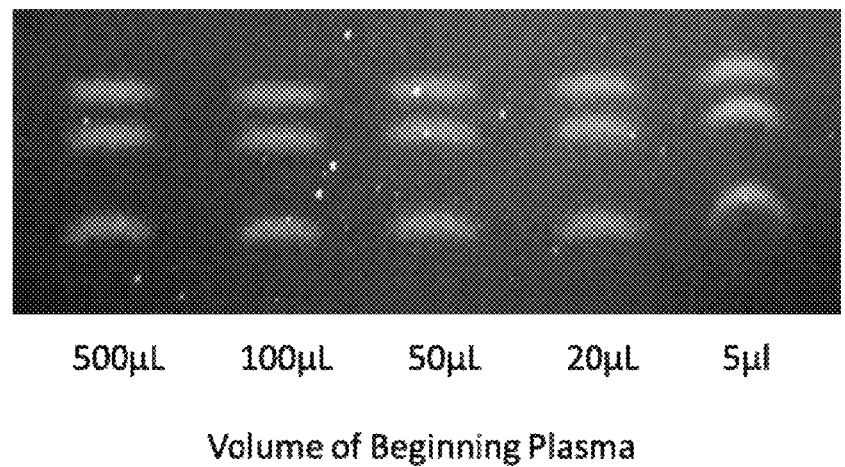

FIG. 8—TLC run from plasma extract of different plasma volumes showing the EPI, DOX and DOL can all be successfully separated from one another with starting plasma volumes as low as 5 µl.

Figure 9A:
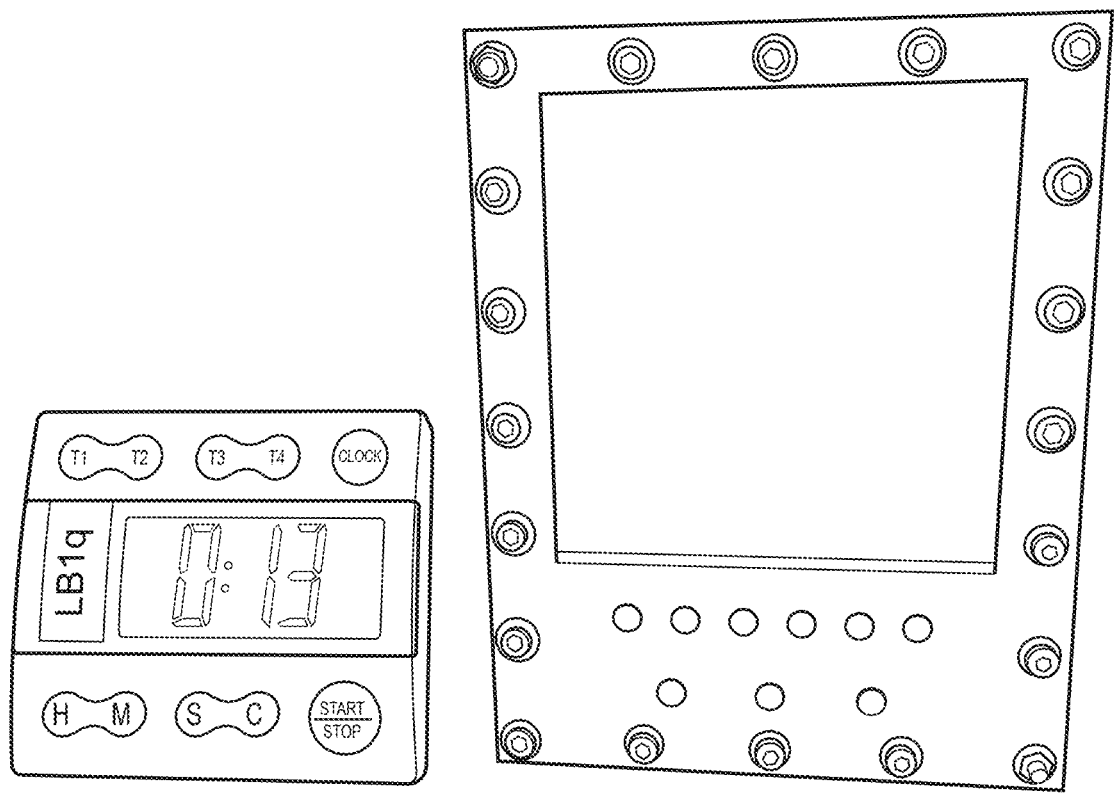

FIG. 9a—Layered prototype design of the TLC cartridge in practice. It is hermetically sealed so there is no leaking of the mobile phase even when tipped up. The sample has been loaded onto the TLC plate and the cartridge tipped up to let the mobile phase touch the bottom of the TLC plate. The mobile phase naturally wicks up the plate and as can be seen after 13 minutes it has made it over ¾ of the way up the plate. This demonstrates that there is nothing inherent about the hermetically sealed environment that prevents normal TLC development from occurring.

Figure 9B:
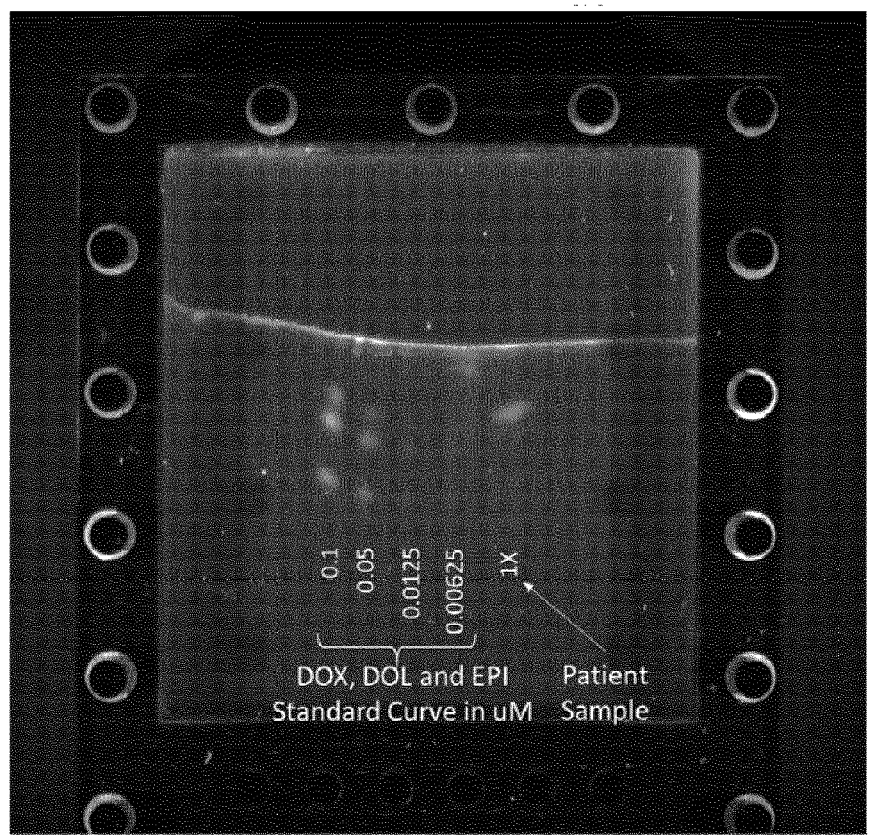

FIG. 9b—A fluorescent image of the developed TLC plate inside the cartridge. The plate is still wet with the mobile phase even though it has been laid down flat and the bulk mobile phase has drained away from the plate. This demonstrates normal development of the TLC plate with well separated lanes and bands. There is a full calibration curve and a patient plasma extract sample. The DOX, Dol, and EPI are clearly visible in all instances. Again, this demonstrates that the hermetically sealed environment does not interfere with the normal development of the TLC plate, nor does it interfere with the fluorescence imaging of the plate.

Figure 9C:
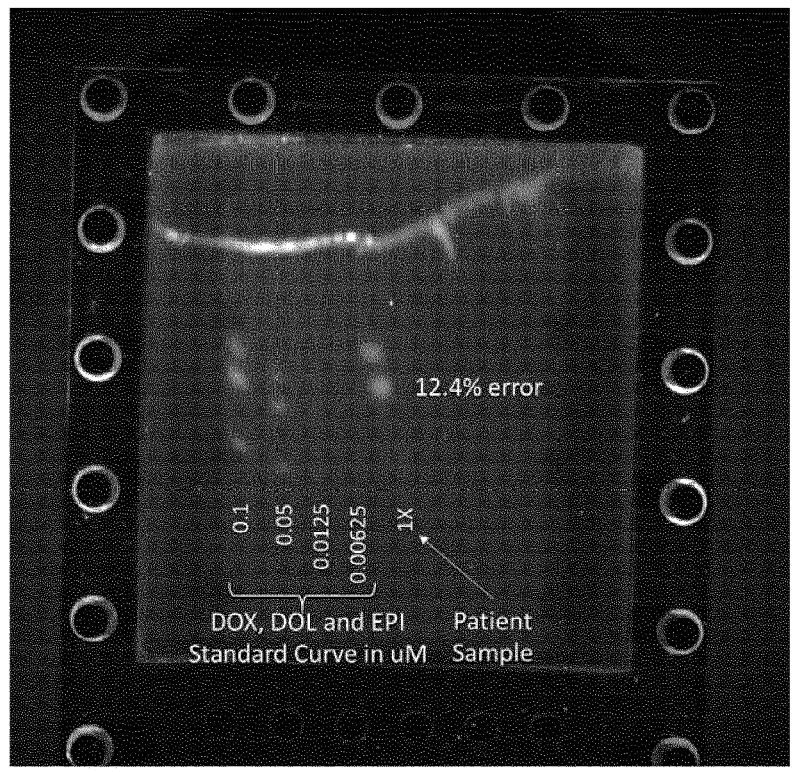

FIG. 9c—Another instance of a successfully developed TLC plate in the hermetically sealed cartridge. Here the DOX in the patient plasma extract was quantified using the analysis software and it was found to have 12.4% error with the gold standard HPLC derived concentration value.

Figure 9D:
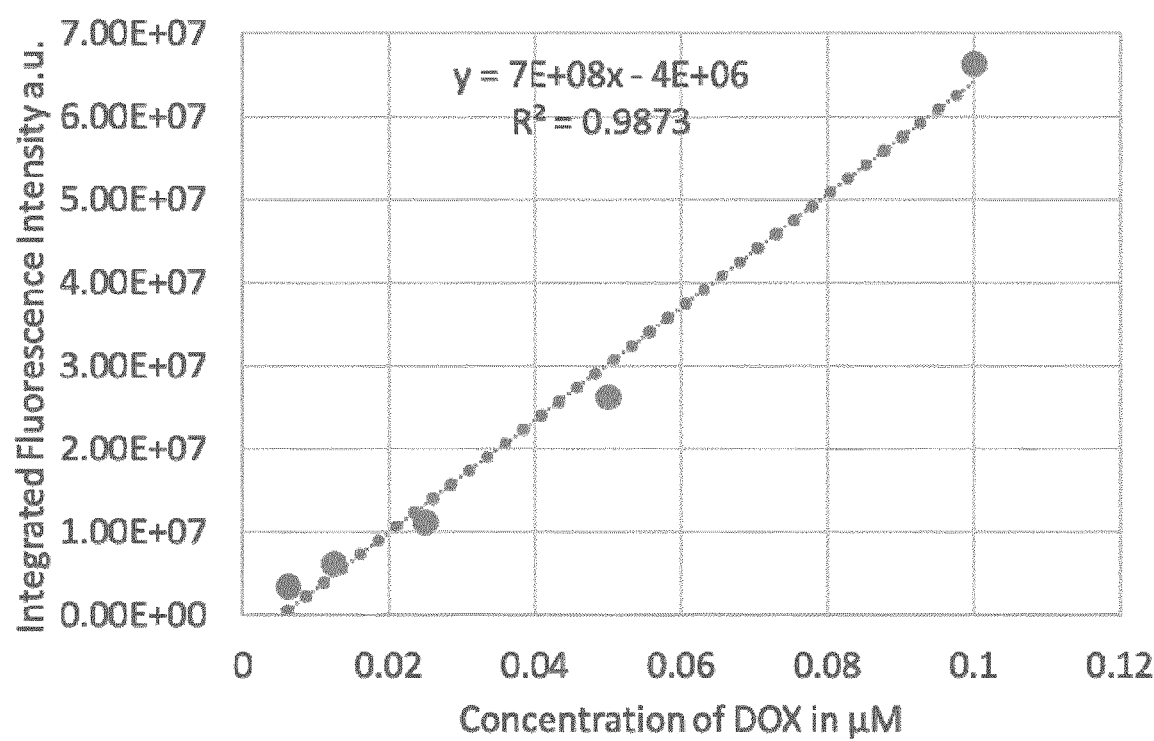

FIG. 9d—A calibration curve from the fluorescence intensities measured on a TLC plate developed inside the hermetically sealed cartridge. The $R^2$ value is 0.987 which shows that the curve is linear across the desired concentration range.

FIG. 10a—Schematic representation of the self-contained TLC cartridge. The cartridge is based on a two chamber concept where the mobile phase and the TLC plate are kept in spate chambers for transport and storage. A glass coverslip barrier between the two chambers is breached and the cartridge tipped up to stand straight up to allow the mobile phase to come into contact with the lower edge of the TLC plate allowing it to develop. The development process is stopped by tipping the cartridge back to lie flat allowing the mobile phase to drain back into the second chamber. The TLC plate can then be imaged from above by a CCD camera system.

FIG. 10b—Further embodiment of the invention, including asymmetric spin chambers for removal of red blood cells.

FIG. 10c—Further embodiment of the invention, permitting treatment with basic chloroform to manipulate pH of the plate. A 'pan structure' holds the basic chloroform when released allowing the whole TLC plate to be soaked with it. It prevents mixing with the acidic mobile phase until after treatment and imaging of the TLC plate. Preferably the mobile phase is not a strong acid allowing them to mix later when discarded without harmful reactions. The pan structure still allows the mobile phase to come into contact with the plate when tipped up to do the initial developing of the plate.

FIG. 10d—Illustration of layers used to prepare one embodiment cartridge of the invention.

Figure 11:
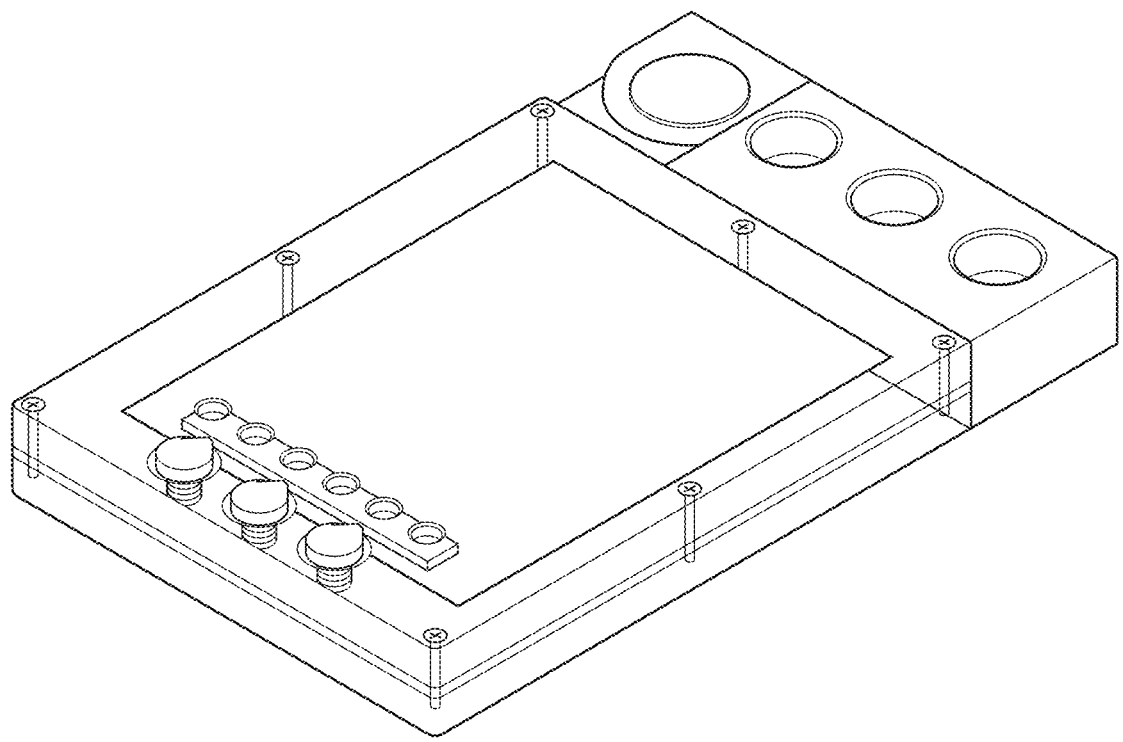

FIG. 11—Image of assembled embodiment of the invention illustration wells and access points.

FIG. 12—Design of the device that automates sample preparation, loading and chromatography.

FIG. 13a-d—MatLab Quantification Code Demonstration for image preparation and quantitative analysis. A optical image taken of Sudan IV dye that has been run on a silica gel TLC plate. B The picture has been inverted by the program to make the bands appear as light bands on a dark background.

TLC lane selection: the user defines the lane where the analyses will take place as the red square. It is important to define the entire length of the lane beyond just the bands of interest so the background subtraction algorithm has the most data to work with to make the background as flat as possible. C. The selected region now appears as a new figure that is stretched out in the X direction to allow better viewing of the band.

TLC band selection: the upper and lower bounds of the band are defined by the user by drawing the red rectangle. D. After the band has been quantified a visual conformation of the area that has been integrated for fluorescence intensity is shown by the red overlay. Additional bands can be sequentially defined and quantified.

Figure 14A:
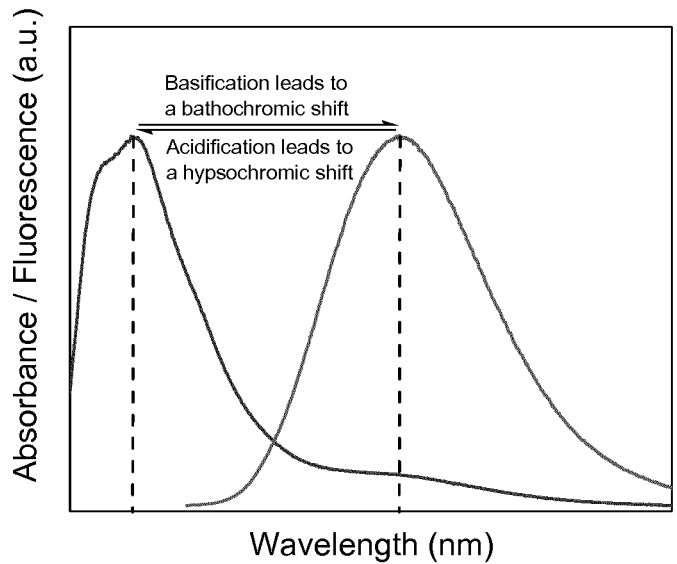
Figure 14B:
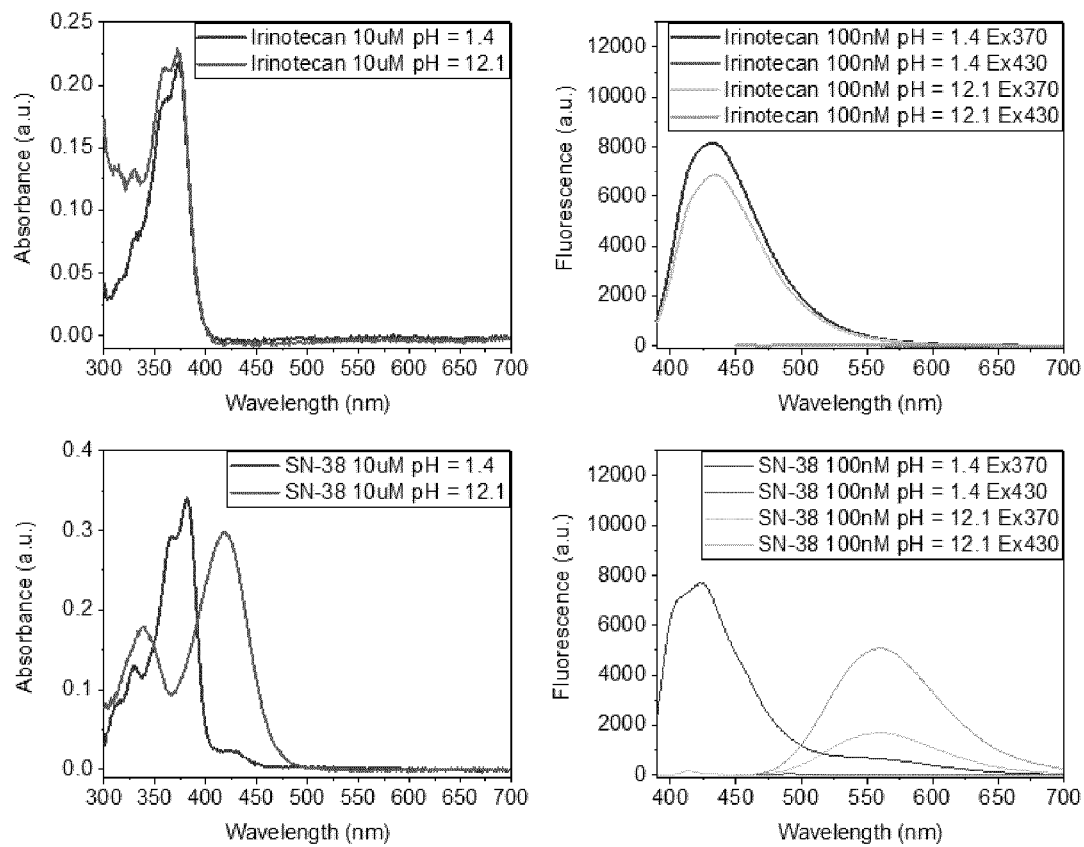

FIG. 14—Bathochromic and hypsochromic shift. FIG. 14A shows a general idealised case. FIG. 14B shows Absorbance spectra (left) and fluorescence spectra (right) of Irinotecan (top), and SN-38 (bottom) at the pH values specified.

Figure 15:
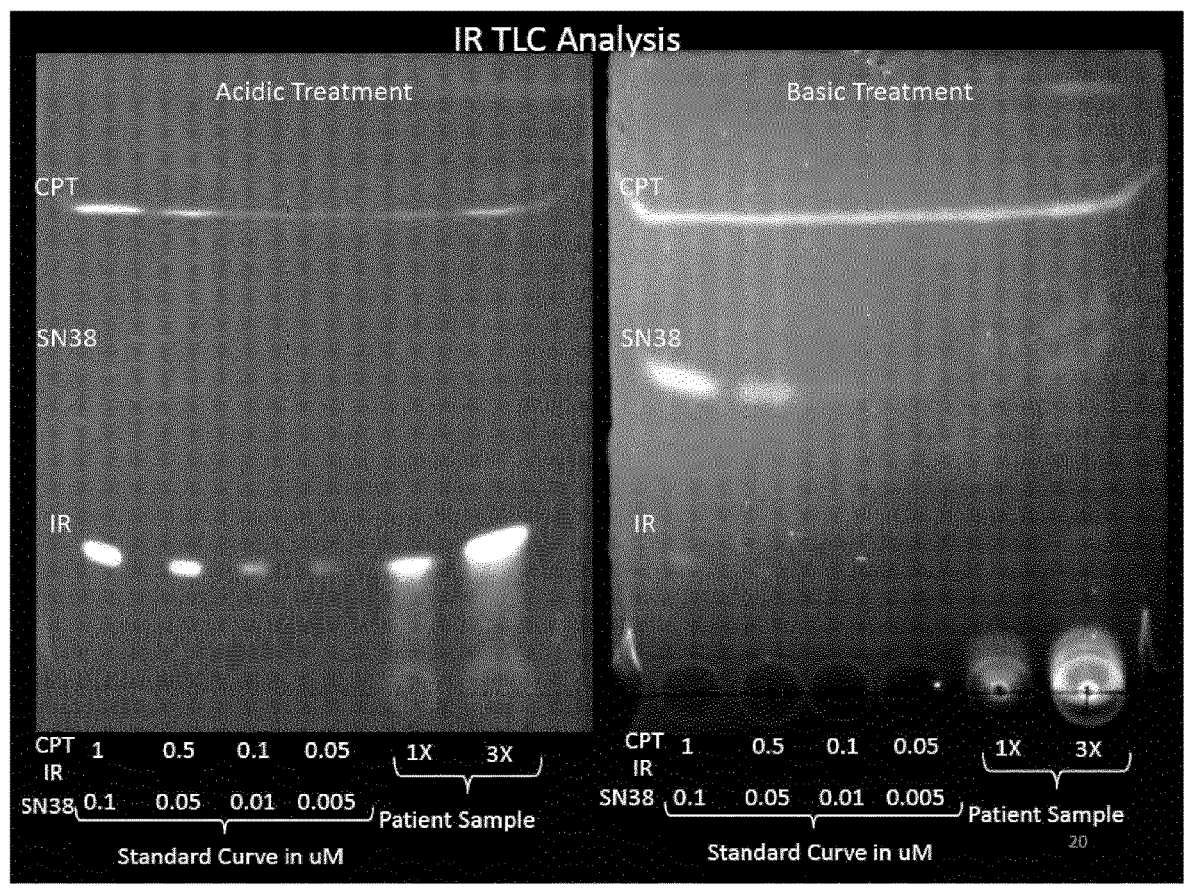

FIG. 15—IR TLC analysis. The Figure shows the different fluorescent properties of the same TLC chromatogram when imaged under acid and basic conditions. CPT=carbonyloxycamptothecin (Irinotecan). SN-38=an active metabolite of CPT.

Figure 16:
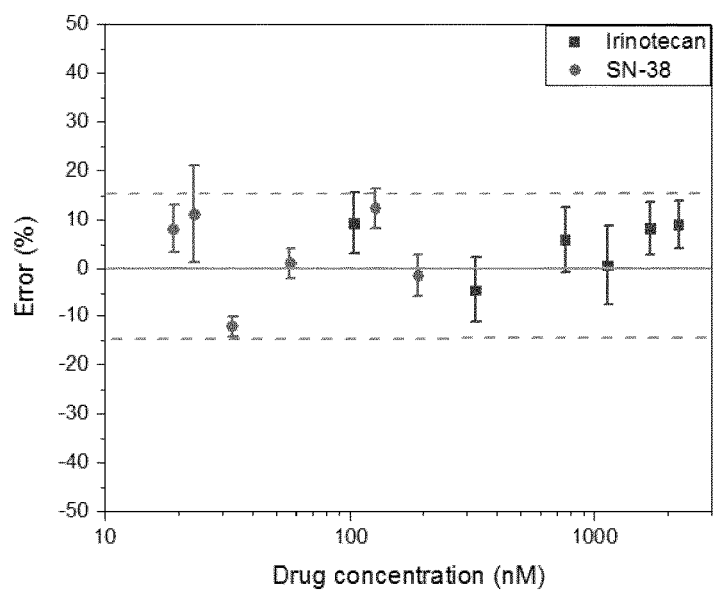

FIG. 16—Quantification of Irinotecan and SN-38 from spiked plasma (n=3). The graph shows the average value and the standard deviation of the measurements.

Figure 17:
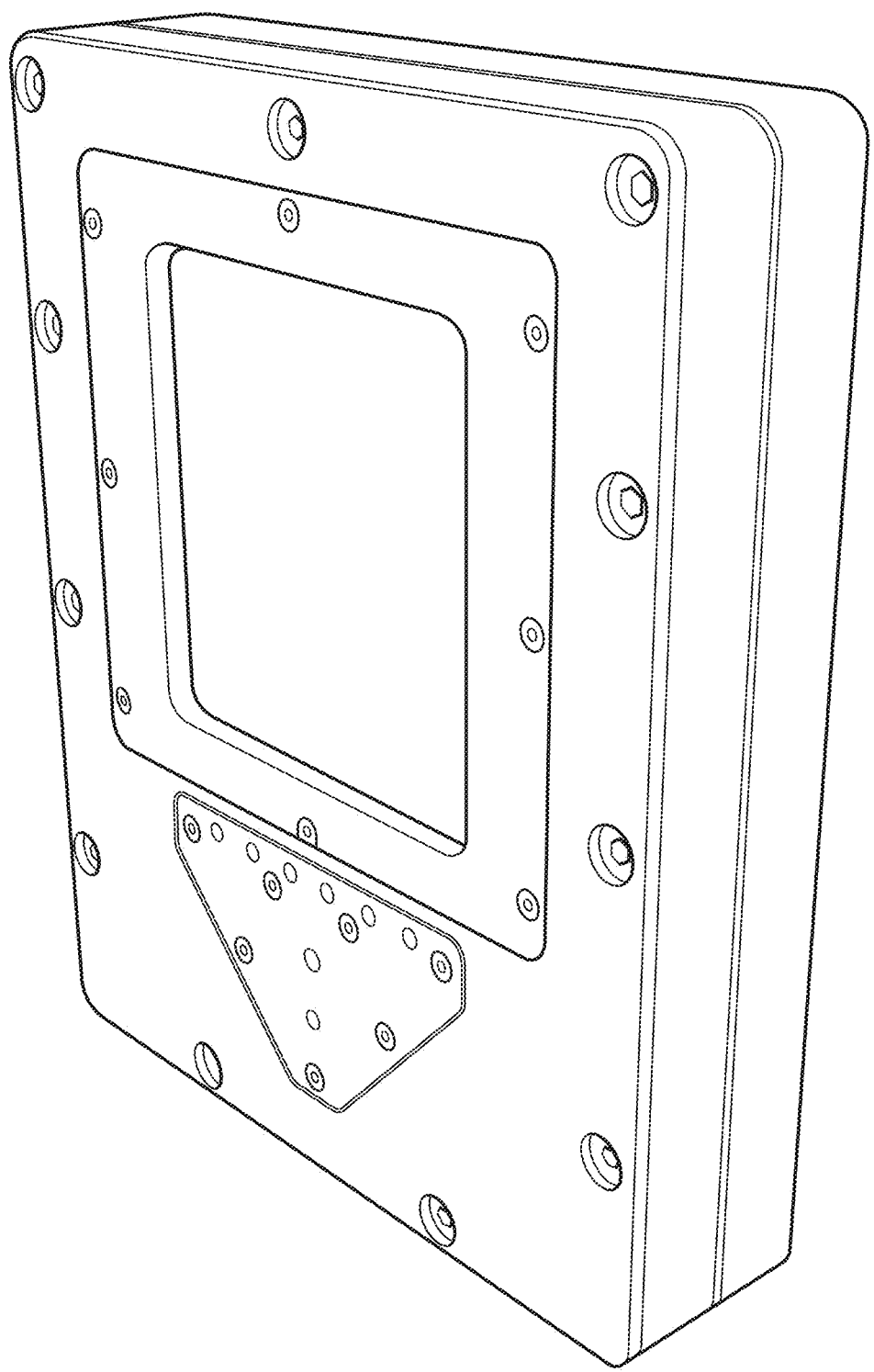

FIG. 17—Cartridge embodiment having a primarily bipartite design comprising upper (face) and lower (base) body units.

FIG. 18—Illustration of the components of the further cartridge embodiment of FIG. 17—(01) Window screw; (02) Window sealing plate; (03) Window; (04) Window o-ring; (05) Septum screw; (06) Injection plate; (07) Septum; (08) Body screw; (09) Upper (face) body; (10) TLC plate; (11) Bridge; (12) Pivot pin; (13) Paddle; (14) Bridge pin; (15) Segregator foil; (16) Body o-ring; (17) Reservoir o-ring; (18) Lower (base) body.

Figure 19:
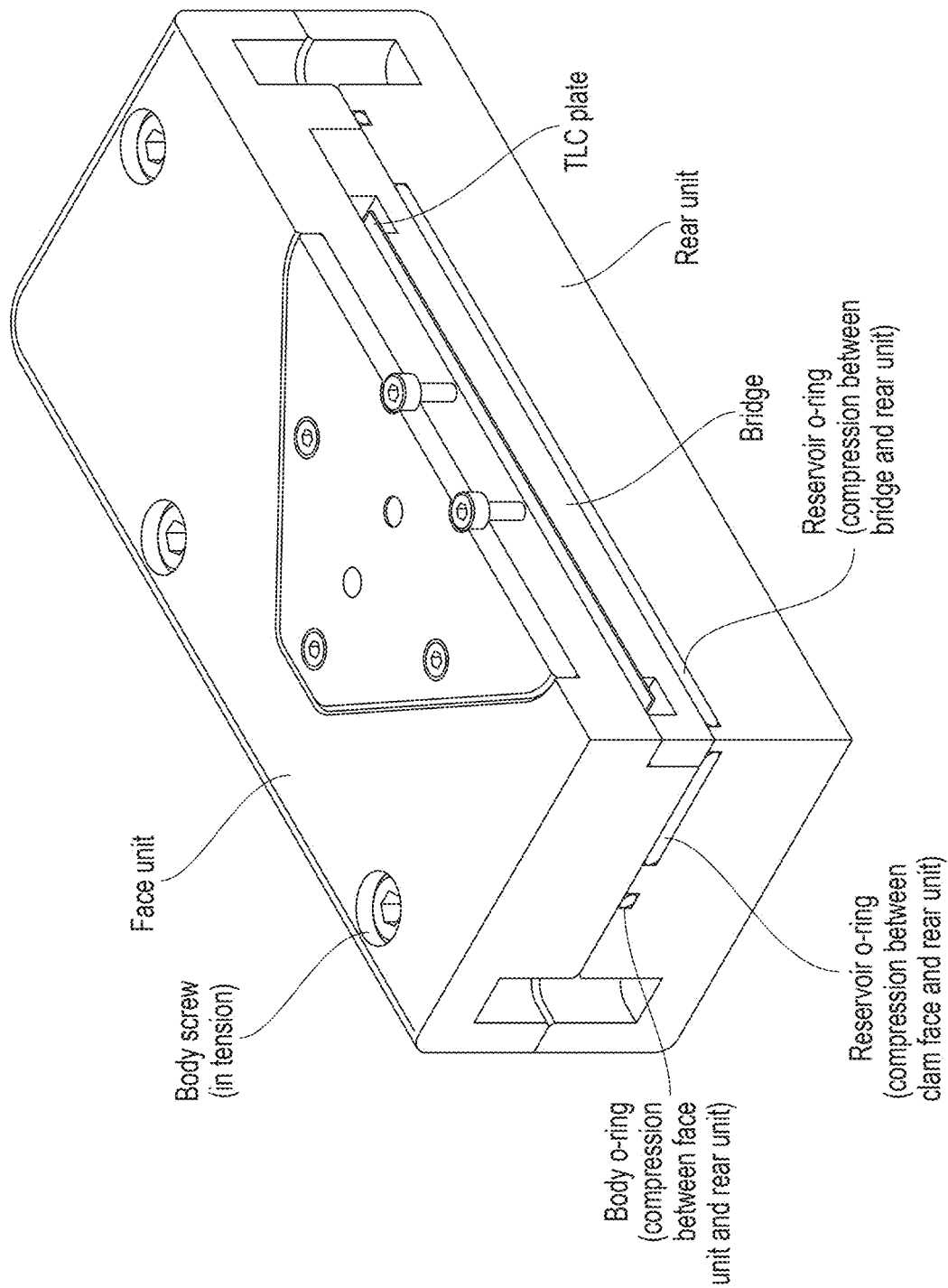

FIG. 19—Illustration showing transmission of force through the bridge.

Figure 20:
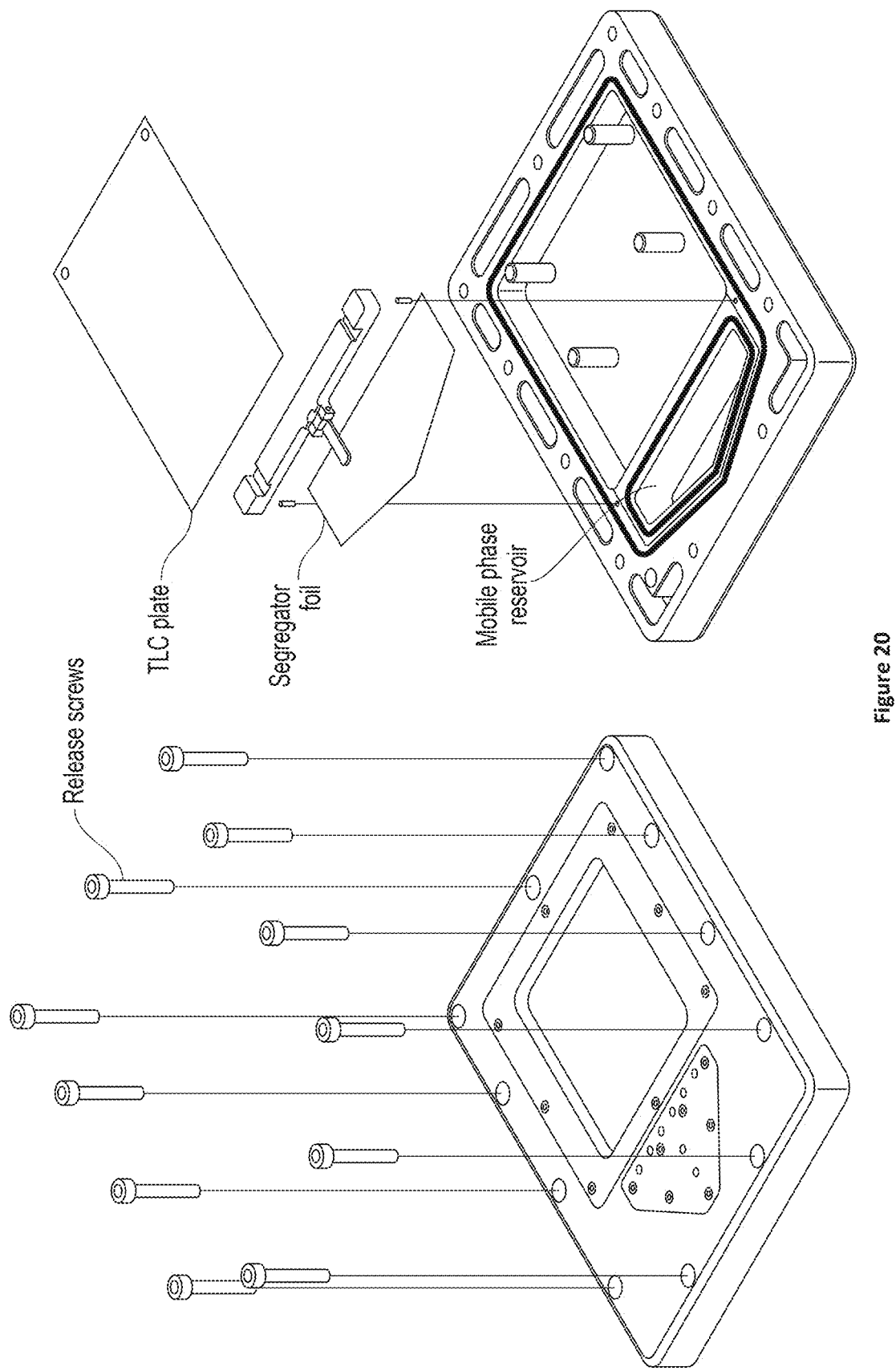

FIG. 20—Illustration showing removal of elements to allow filling or refilling of mobile phase reservoir.

Figure 21:
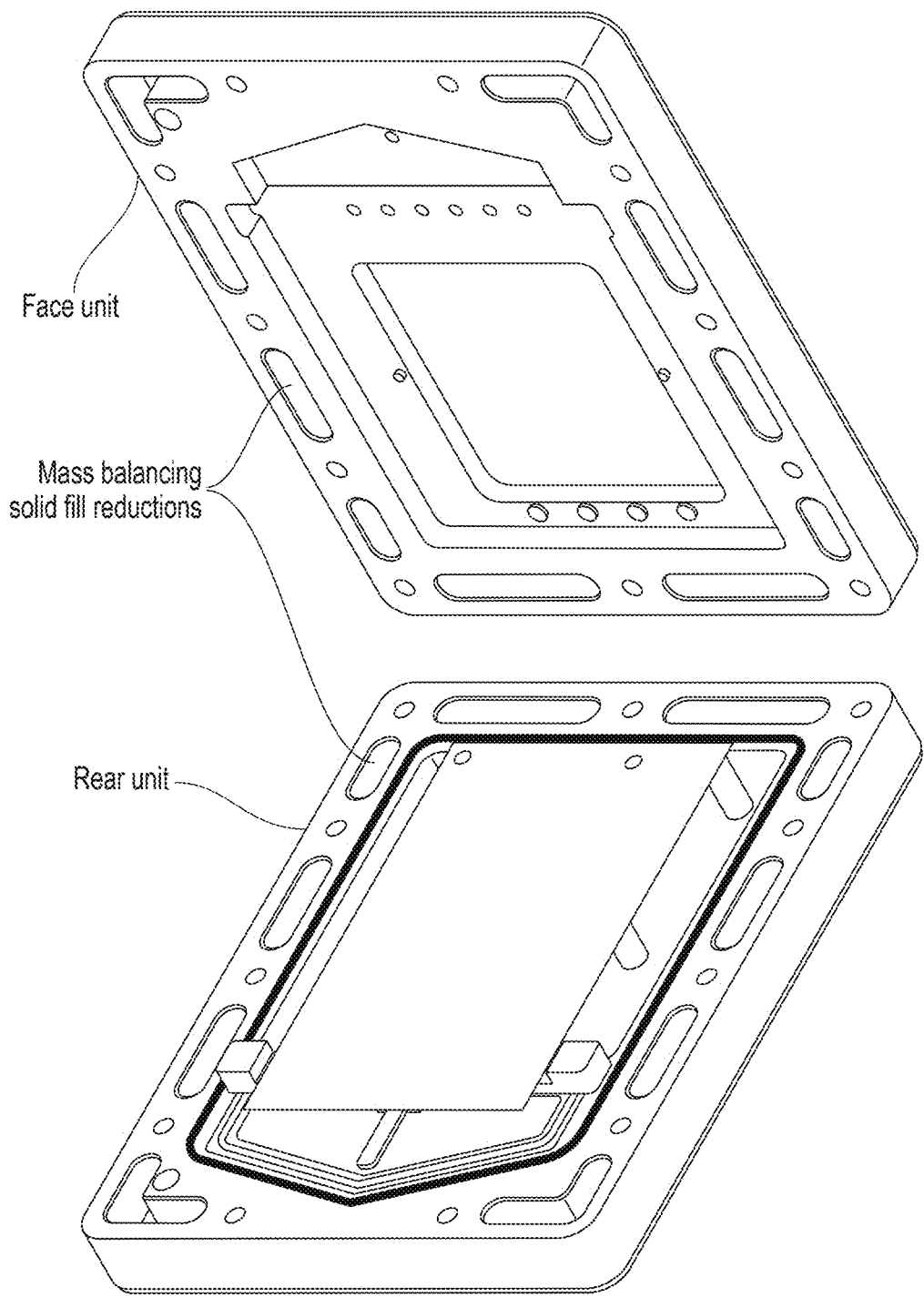

FIG. 21—Illustration showing location of "solid fill" modification regions which can be used to modify the mass of the cartridge.

Figure 22:
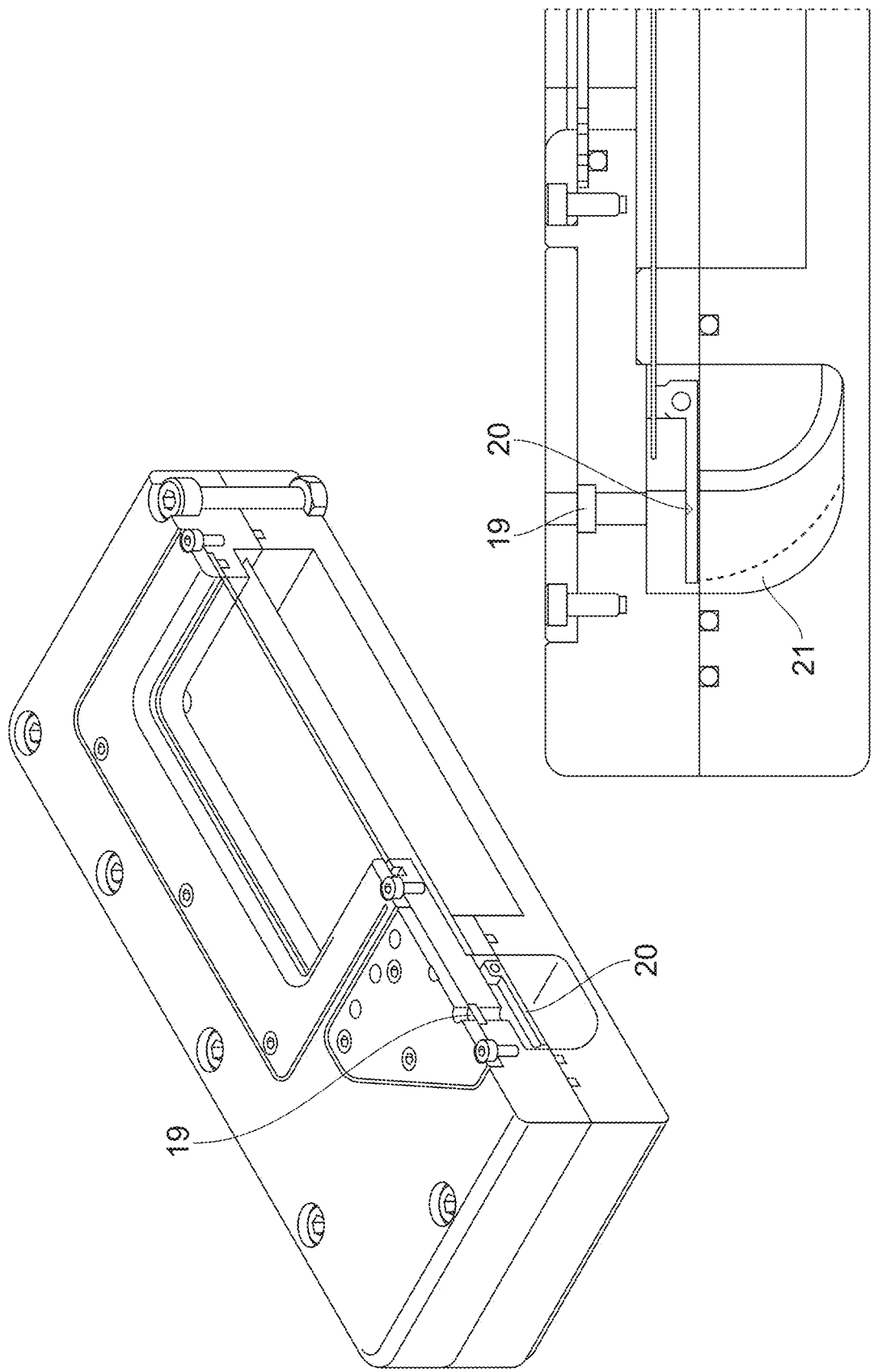
Figure 23:
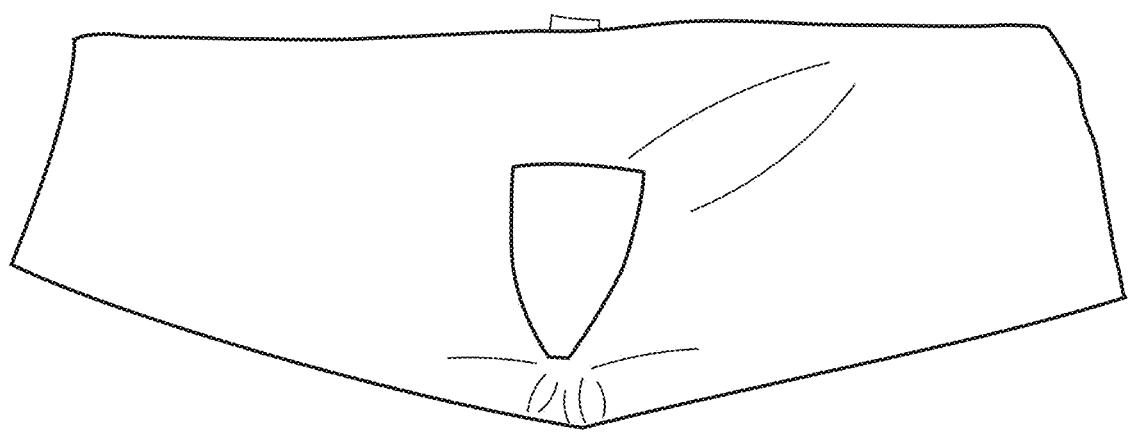

FIGS. 22 and 23—Illustration showing penetration of the segregator by a needle to release the mobile phase.

Figure 24:
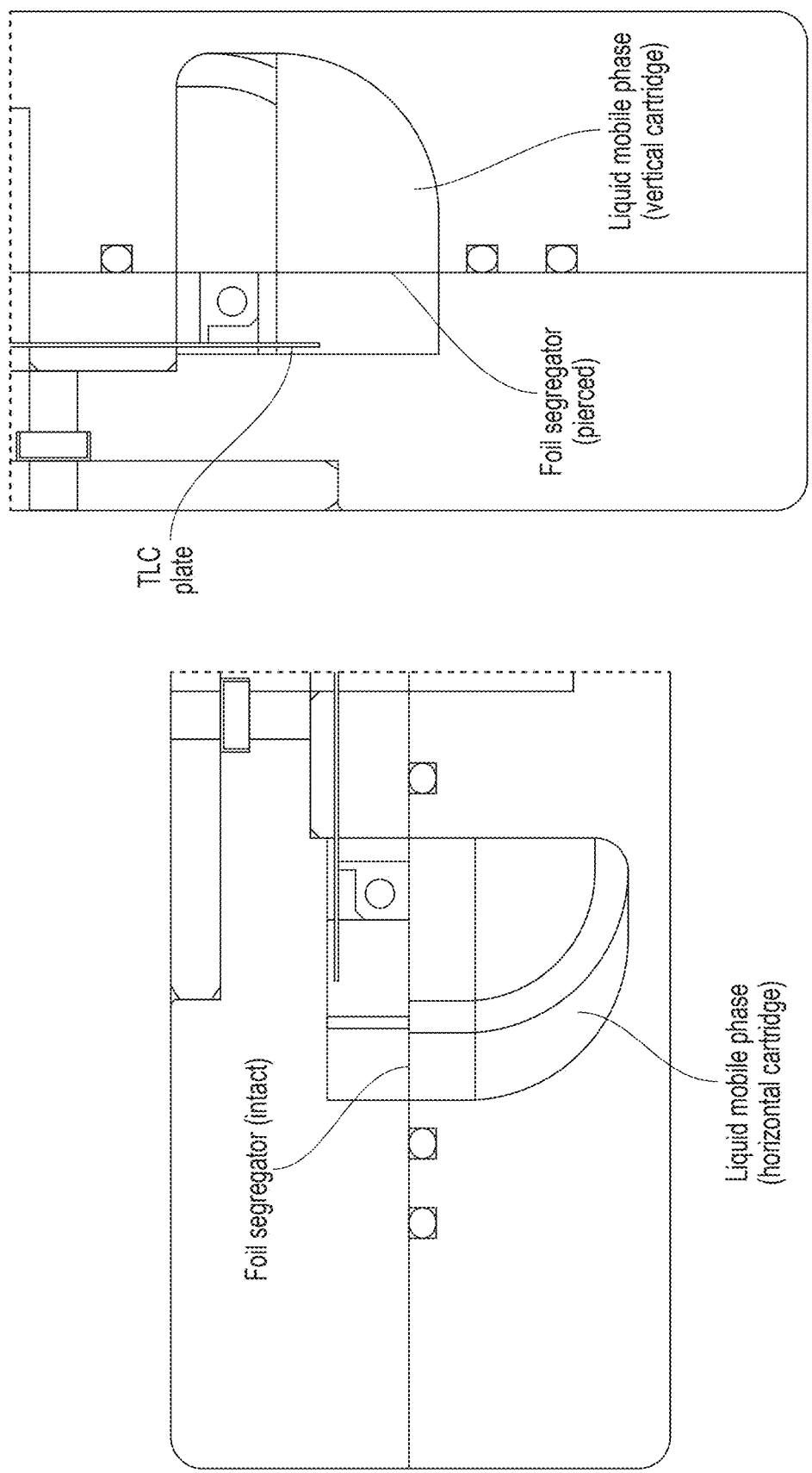

FIG. 24—Illustration showing how rotation of cartridge exposes the TLC place to mobile phase after the reservoir is pierced.

Figure 25:
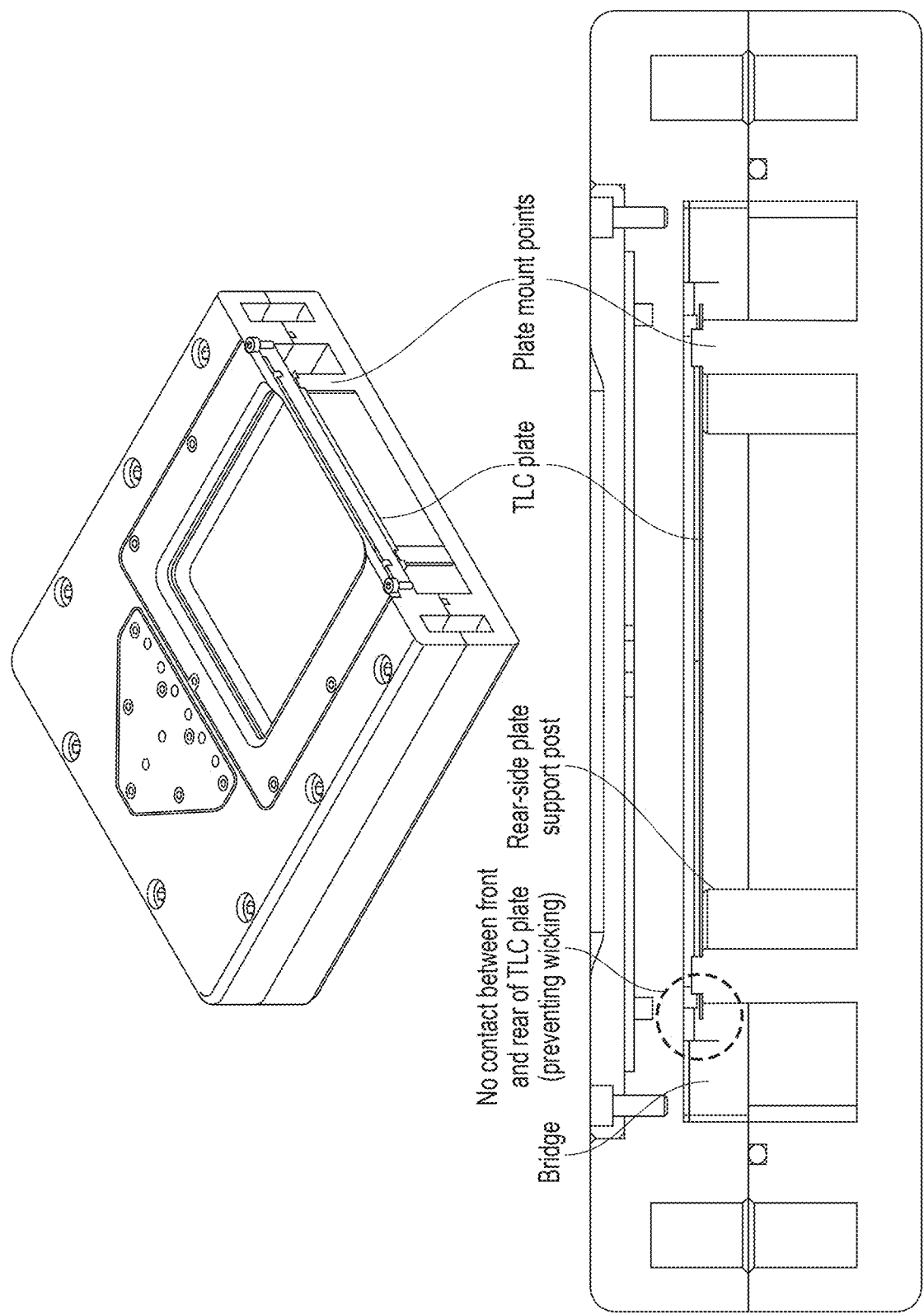

FIG. 25—Illustration showing detail of support posts in rear unit which support the TLC plate, and separation of front and rear of TLC plate to prevent wicking.

Figure 26:
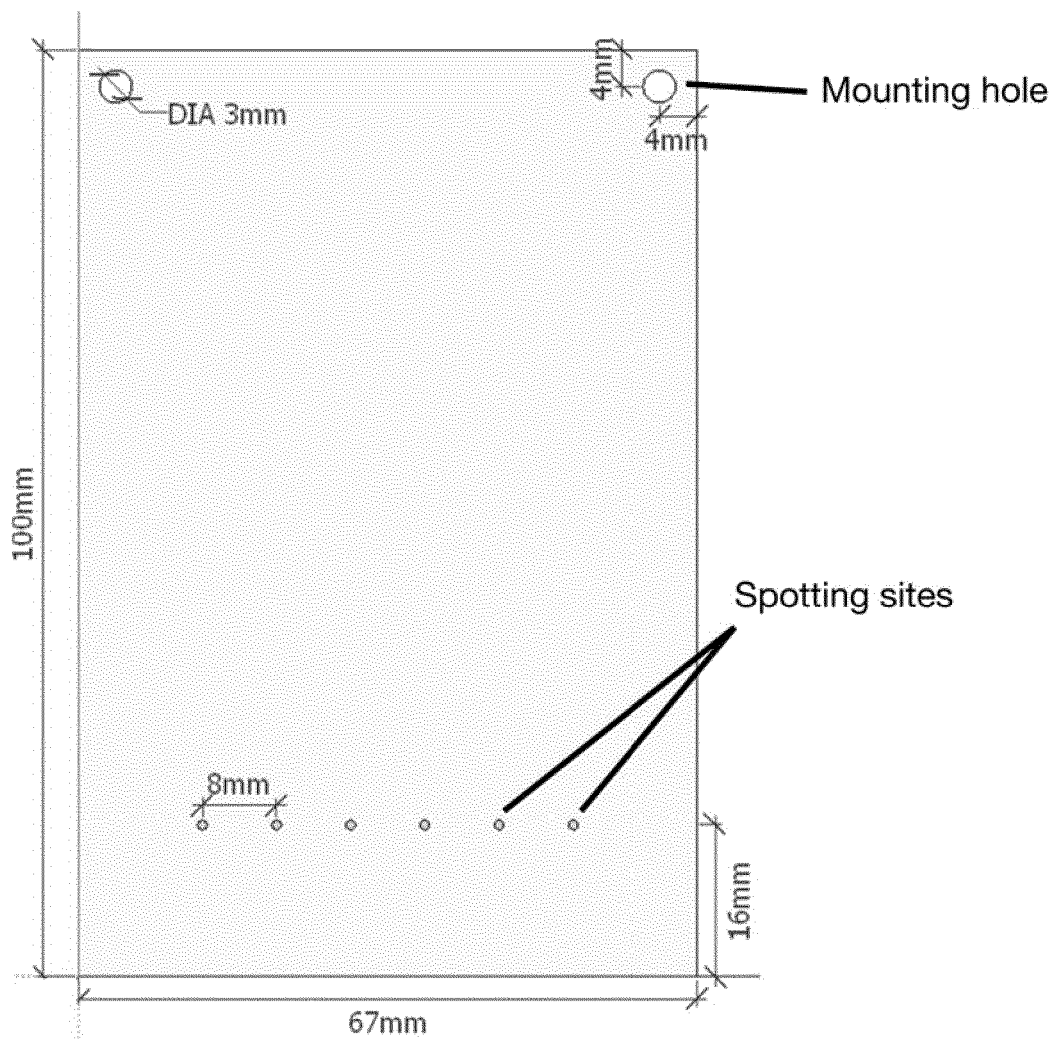
Figure 27:
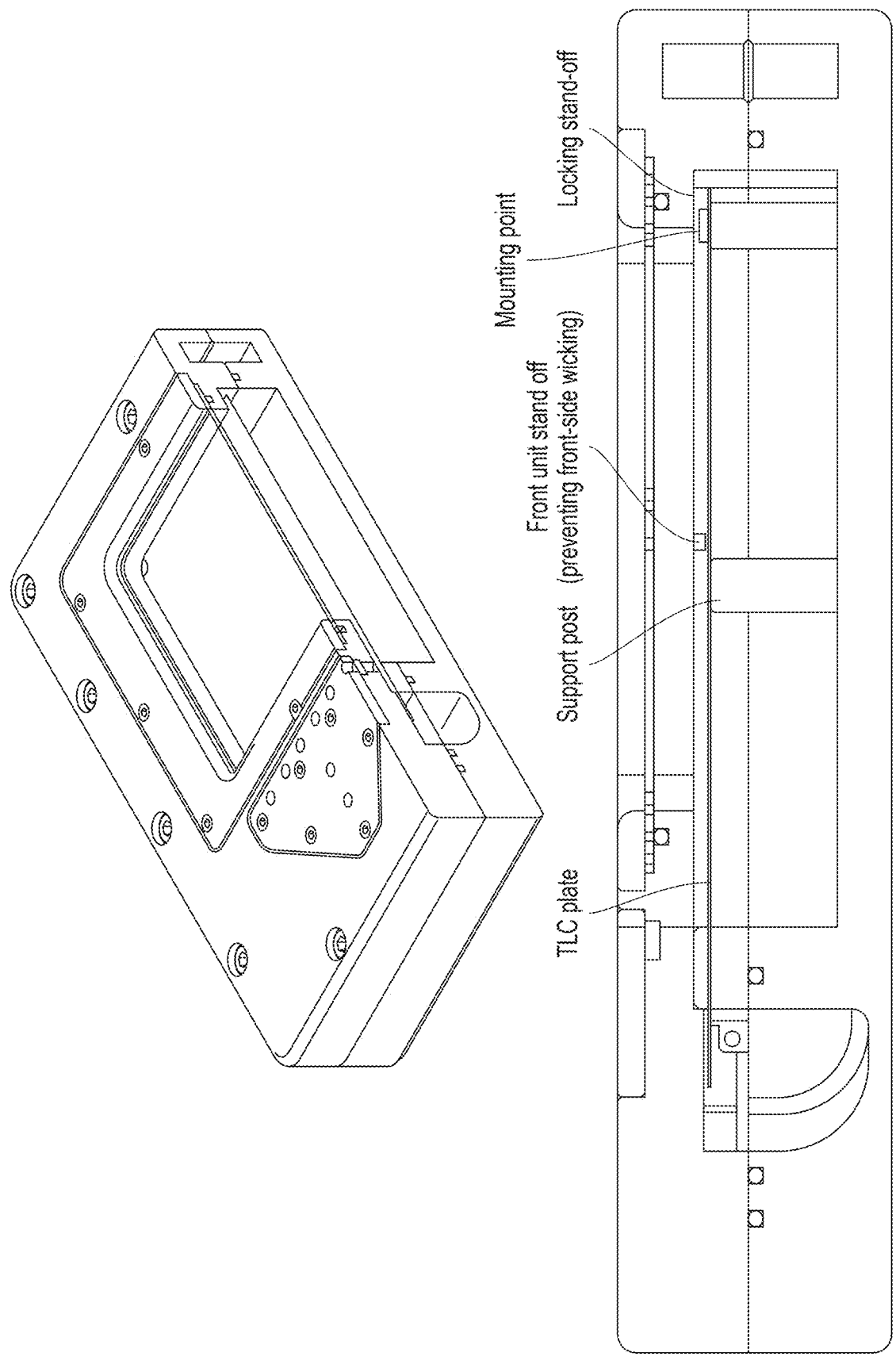

FIGS. 26 and 27—Illustration showing detail of stand-off posts in front unit which help to prevent wicking across the TLC plate.

Figure 28:
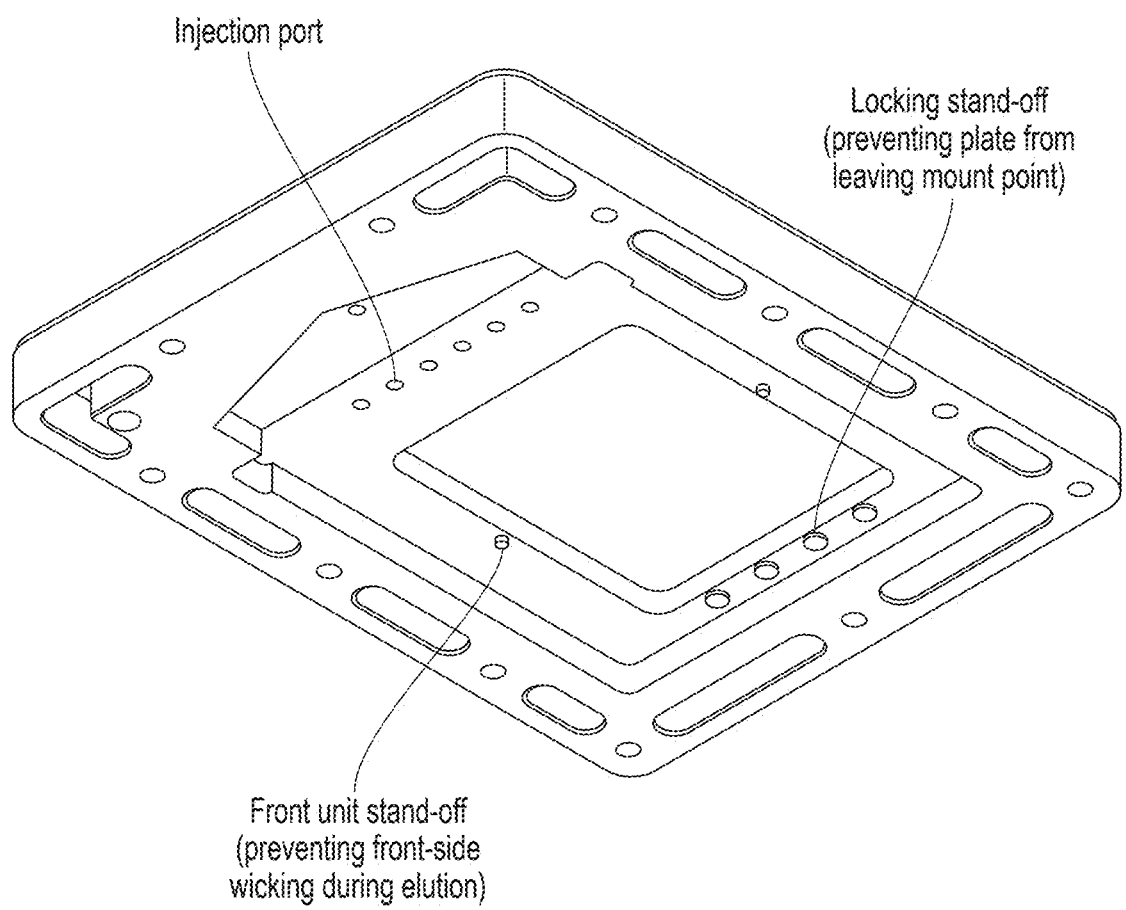

FIG. 28—Illustration showing detail of support posts in rear unit which support the TLC plate, and separation of front and rear of TLC plate to prevent wicking.

Figure 29:
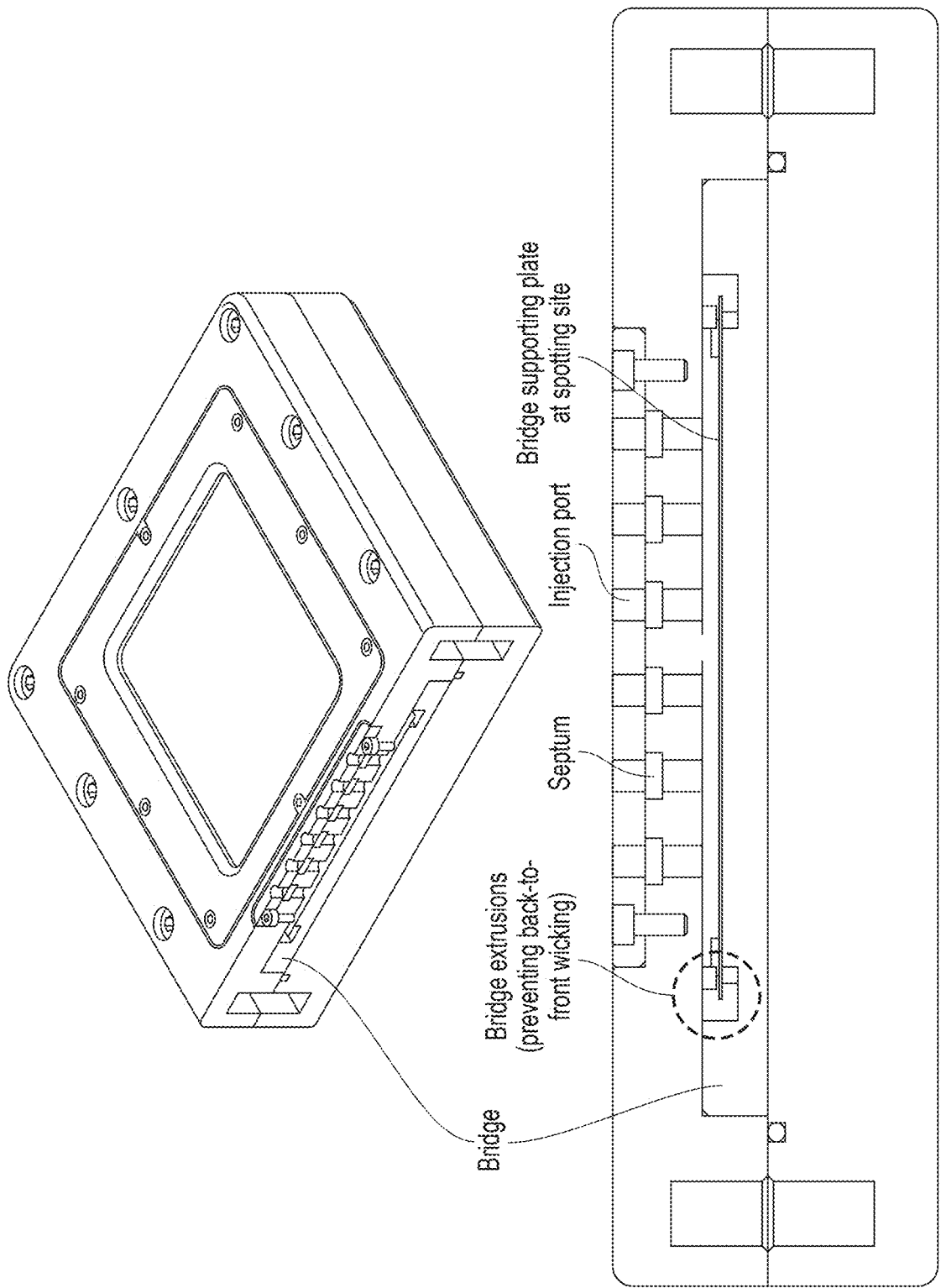

FIG. 29—Illustration showing cross section of the bridge and injection, illustrating how the edge extrusions assist in preventing wicking.

Figure 30:
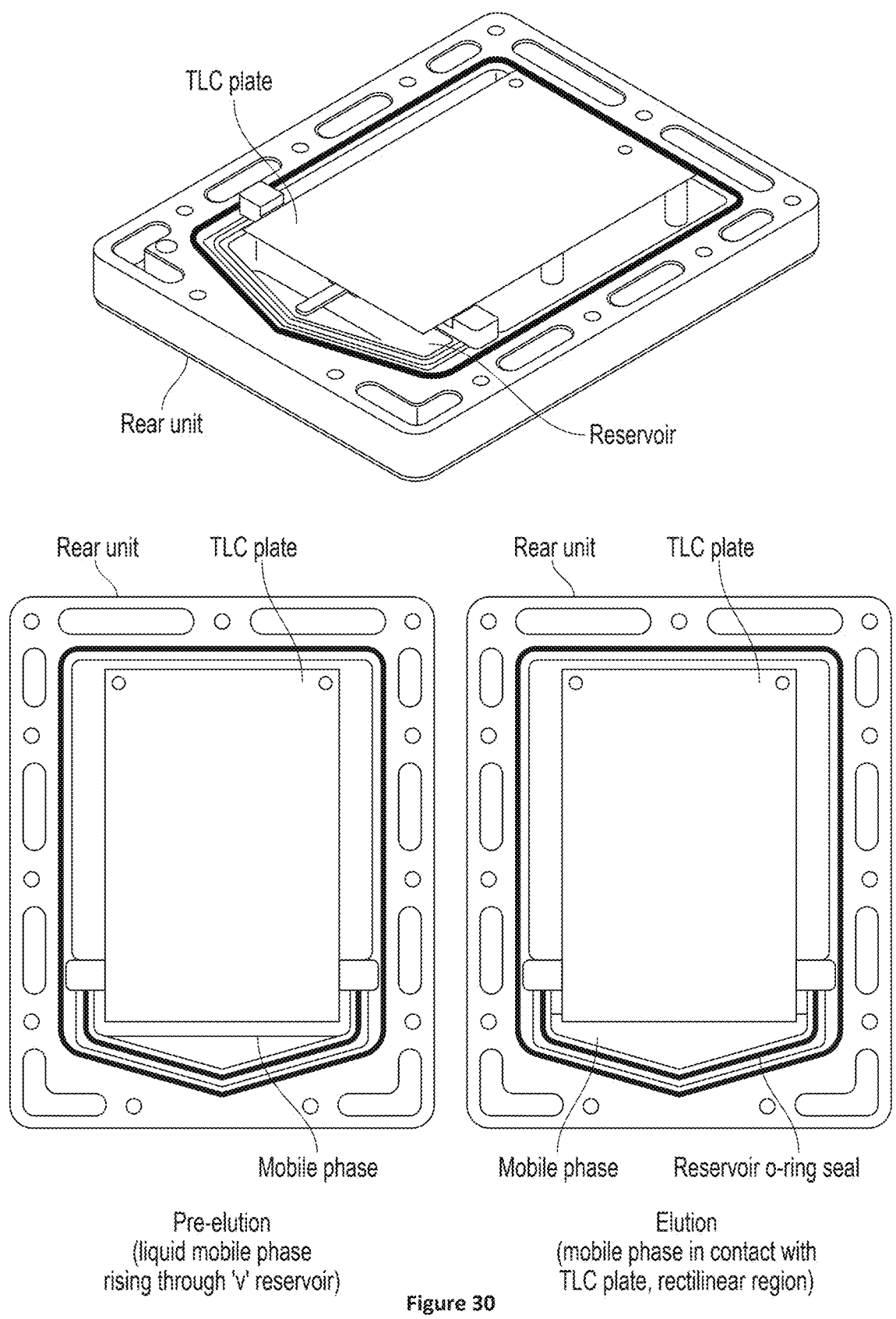

FIG. 30—Illustration showing profile of mobile phase reservoir when vertical: the reservoir follows a tapering 'v' contour below the TLC plate (in both the face and rear units) but enters a rectilinear profile before the lowest point of the TLC plate.

EXAMPLES

Example 1—Materials and Methods

Materials

Doxorubicin hydrochloride, epirubicin hydrochloride, irinotecan, CPT, and acetic acid were all purchased from Sigma Aldrich (Dorset, United Kingdom). Doxorubicinol hydrochloride was purchased from Toronto Research Chemicals (Toronto, Canada). The Analytical Chromatography TLC Silica gel 60 $F_{245}$ used for the DOX experiments and the Analytical Chromatography TLC Silica gel 60 for the irinotecan experiments were both purchased from Merck/Millipore (Hertfordshire, United Kingdom). The methanol and the acetonitrile were purchased from Fisher Scientific (Loughborough, United Kingdom). The chloroform was purchased from VWR (Leicestershire, United Kingdom). Water was purified using the MilliQ filtration system from Merck/Millipore (Hertfordshire, United Kingdom). Healthy plasma samples and the irinotecan clinical patient samples were generously donated from at the Centro di Riferimento Oncologico di Aviano, Italy. The doxorubicin clinical patient samples were generously donated from the Universitat Münster Klinik für Kinder and Jugendmedizin, Germany. Imaging of the TLC plates was performed using a SynGene PXI imaging system (SynGene, Cambridge, United Kingdom). MatLab R2015A was used to write the custom optical quantification program (Mathworks, Cambridge, United Kingdom). The cartridge materials consisted on chemically resistant Teflon plastic and flexible Teflon tape.

Mobile Phase PREPARATION

The mobile phase consisted of chloroform:methanol:aceticacid:water (80:20:14:6) (v:v:v:v)[12, 23]. The mixture was shaken to ensure proper dissolution of any water droplets that formed. If the water would not dissolve giving the solution a cloudy white appearance then the solution was placed in a 37° C. water bath until the solution became clear. The running of the TLC plate was performed at room temperature.

Preparation of Spiked Plasma Samples

A 100 µl sample of plasma from healthy donors was spiked with 10 µl of a prepared solution of EPI, DOX and DOL in methanol in various concentrations. The spiked sample was vortexed at max speed for 10 seconds to ensure proper mixing. The plasma was prepared beforehand using centrifugation to pellet out the red blood cells.

Calibration Curve Samples

A solution of DOX, DOI, and EPI (each at 1 µM) in methanol, was prepared and then diluted samples from this were made at 0.5, 0.1 0.05 µM. These four concentrations were placed onto each TLC plate to prepare the standard curve for that plate.

Spiking Internal Standard into Clinical Samples

A 10 µl sample of 0.5 µM Epirubicin (EPI) in methanol was spiked into 100 µl clinical plasma samples to provide an internal standard. EPI was chosen because it is an isomeric form of DOX [24] that has very similar chemical and fluorescence properties to both DOX and DOL. The difference between the recovered amount of EPI and the known amount of EPI spiked into the plasma sample helped to scale the DOX and DOL concentration values to account for variability in the extraction efficiency as well as effects on overall fluorescence levels that could potentially be influenced by the buffering properties of the plasma.

Drug Extraction from the Plasma with Protein Precipitation

The proteins needed to be precipitated from the plasma solution because they would interfere with the running of the TLC plate due to their hydrophilicity and high concentration. A mixture of acetonitrile:methanol (2:1) (v:v) was prepared[19]. A 100 µl sample of plasma was placed in a 15 ml tube followed by a sample of 250 µl of the above solution. The sample was aspirated 3 times, vortexed at maximum speed for 10 min and finally spun down at 5000 rpm for 5 min. The resulting supernatant containing the extracted drugs was carefully removed leaving the precipitant pellet at the bottom of the tube. This supernatant was then placed in a glass vial for analysis.

TLC Plate Loading and Development

A 10 µl sample of each of the calibration curve solutions was loaded into the first 4 lanes of the TLC plate. A single 10 µl sample of the plasma extract was loaded onto the 1× sample lane. The 3× sample lane had three sequential 10 µl samples of the plasma extract loaded on top of each other allowing the solution to dry between applications. Loading three samples like this increased the signal which was important for low concentration samples. Loading more than 3 spots caused observed distortions to the bands that could cause trouble with quantification.

The TLC plate was allowed to air dry for 5 min while being covered with aluminum foil to prevent photobleaching of the sample.

For the DOX samples the plate was then placed into a beaker containing the mobile phase where the liquid level covered the bottom of the TLC plate with the upper level of the mobile phase below the level of the sample spots on the TLC plate. The container was covered to increase the vapor pressure of the solvent in the container and speed the development of the plate. The plate was then run for 30 min until the advancing phase was just below the top of the plate. This covered a distance of approximately 8.5 cm.

For the irinotecan samples the mobile phase was diluted 50:50 (v:v) with chloroform and then treated the same as for the DOX samples.

Optical Analysis of the TLC Plate

After the plate was developed and before the solvent had a chance to evaporate, the TLC plate was placed into a SynGene PXI Imaging System and the plate was imaged at different exposure times using the blue mLED illumination unit coupled with a UV06 filter. An exposure time of 30 seconds was used to image the DOX plates and 30 seconds was used to image the irinotecan plates.

A custom MatLab program was then used to quantify the fluorescence level of each band in both the calibration curve samples and in the 1× and 3× sample lanes. The intensity values determined for the DOX and DOL bands in the 3× sample lane were compared to the calibration curve generated using the 0.1 and 0.05 µM concentrations of DOX and DOL. These values were then scaled by the difference in the measured and expected results of the EPI internal standard concentration.

Analysis Program

The custom MatLab program analysed each band by first allowing the user to define the boundaries of the lane in which the bands were located. The program then allowed the user to define an upper and a lower bound in which a particular band of interest was located. The program started by analyzing a single line of pixels running the length of the lane and did so sequentially for each line of pixels starting from left to right covering the width of the lane. For each line of intensity data, the MatLab function "msbackadj" was used to flatten the uneven background created by the lighting source. This created a flat background level at zero fluoresce intensity from which the band peaks could be detected along the length of the defined line. The program would then define the physical dimensions of band in the y direction by defining the full-width-half-max of the peak. The area under this defined portion of the curve was calculated using the trapezoidal approximation using the MatLab function "trapz". This process was repeated for the next line of pixels until the entire width of the user defined lane was analysed. The X dimensions of the band were determined by setting a lower threshold limit for peaks to be defined by using a "Min Peak Prominence" of 1500 for DOX and for irinotecan. Lower concentrations of irinotecan required the thresholds be adjusted downward compared to the highest concentrations to make sure they were properly detected. The area under the curve defined by each line of pixels was added together to produce a total intensity for the fluorescence band.

It was important that the program objectively defined the actual boundaries of each band to prevent user error from influencing the obtained intensity values. The user's only influence on the program was to define the rough boundaries of a band in which the program could then search for and define the actual band.

In practice the program was used as follows:

1 The program asks the user how many lanes and how many bands in each lane are to be analysed.

2 The MinPeakProminence then needs to be determined, which defines the prominence of the peak maximum with respect to the noise floor. The default setting is set to 1500 which works well for most application.

3 The program then asks for the divisor value. This is the value that the program uses to divide the peak max value to define the lower limit of the peak. The default is set to 2, so the full width half max of the peak will be analysed.

4 The program will ask the user to select a file of the picture to analyse. The user then draws a rectangle to define the entirety of a single lane as shown in FIG. 13B.

5 The program then compiles a new picture using just the band (FIG. 13C). The user draws a small rectangle to define the upper and lower bounds of the first band. The left and right dimension of the rectangle are not used for the analysis.

6 The program will analyse the band and return the integrated fluorescence intensity. It will also cover in red the region that was analysed (FIG. 13D). This can take up to 20 seconds to complete. 2 parameters can be adjusted in case the identified region does not overlap well with the band of interest. If that red region extends significantly beyond the left and right of the band itself, then the MinPeakProminence value needs to be increased. If the program does not register a band and there is no red region then this value needs to be lowered.

This is repeated for other lanes and bands.

7 Once all the band intensities have been quantified they can be used to determine the concentration of the analyte. The fluorescence intensity versus known concentration of the standard curve samples is plotted and fitted with a linear curve fit. The equation for that line can then be used to calculate the concentration of the unknown sample based on its measured fluorescence intensity. This is done by utilising the fluorescence intensity of the band of interest in the equation for the fluorescence intensity variable and then solving the equation for the concentration variable.

HPLC Quantification of DOX and DOL from the Same Clinical Plasma Samples

Each of the clinical samples analysed using the TLC method described above was also assessed using traditional gold standard HPLC method. A 100 µl sample of patient plasma was spiked with 50 µl of ethanol containing 120 µg/L EPI as the internal standard. Then 100 µl of a solution of phosphate buffer (pH 8.5) and 1000 µl chloroform was added followed by mixing on a rotation shaker for 5 min at max intensity. The solution was then centrifuged for 5 min at 20,800 g. The organic phase was then transferred to a new tube and evaporated with nitrogen at 35° C. The resulting residue was redissolved in $H_2O$/acetonitrile 3:1 (v:v) with 0.1% formic acid for injection into the HPLC.

The HPLC-method used a C18 column with a dual gradient elution. Solution A was 0.1% formic acid in $H_2O$ and solution B was 0.1% formic acid in acetonitrile. The elution protocol started with 75% A and 25% B changing to 70% A and 30% B over 7 minutes. Then the solution changed to 58% A and 42% B over 3 minutes. Detection was fluorescence based using 488 nm excitation and 555 nm emission wavelengths.

HPLC Quantification of Irinotecan from the Same Clinical Plasma Samples

The HPLC protocol used to determine the gold standard values of irinotecan in the clinical patient samples was previously established and is described in Marangon et al.[25].

Clinical Plasma Sample Collection from DOX Patients

The plasma samples used in the study were obtained during a larger clinical study as described by Krischke et al. [26].

Example 2—Results

Separation in Spiked and Clinical Plasma Samples

The mobile phase was successful in being able to separate the EPI, DOX, and DOL from one another using the Silica TLC plate as shown in FIG. 1. The separation between EPI and DOX was sufficient to resolve the two bands from one another for successful quantification.

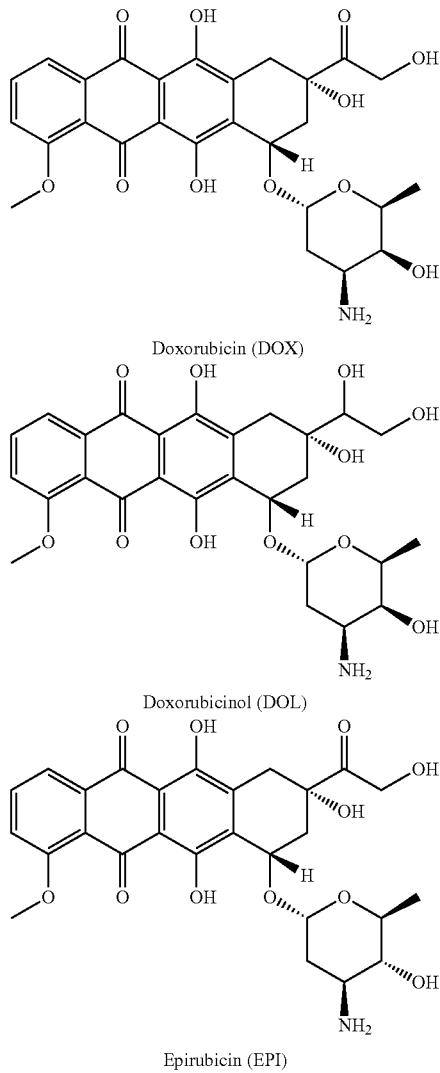

Doxorubicin (DOX)

Doxorubicinol (DOL)

Epirubicin (EPI)

The TLC method was also able to successfully separate the EPI, DOX and DOL from spiked plasma samples as shown in FIG. 2. Hemoglobin present in the plasma sample is also separated into a band below DOL. Hemoglobin has an absorption and emission spectra that is very similar to DOX and DOL which makes its physical separation from the drugs essential to prevent interference.

The process also successfully separated the EPI, DOX, and DOL from clinical plasma samples collected from patients undergoing chemotherapy treatment with DOX as shown in FIG. 3. TLC plates from two different patients is shown. As can be seen there is a large variation in the amount of contaminating plasma residue from patient to patient.

Optical Analysis of TLC Plates

The fluorescence imaging of the TLC plates of DOX and DOl was performed using the SynGene PXI gel reader system. DOX, DOL, and EPI are all naturally fluorescent compounds allowing the fluorescence mode of the PXI system to easily distinguish the drugs from the background. FIG. 4 shows the linearity of the system in quantifying the fluorescence intensity over a range of DOX and DOL concentrations from 0.01 to 10 µM.

A custom MatLab program (described in more detail below) was used to obtain intensity values for the different bands. The results of the quantification and their comparison to the gold standard HPLC values obtained for the same DOX clinical samples is shown in FIG. 5. The samples were run in triplicate and were compared to the concertation obtained using HPLC for the same sample. The error between the HPLC and the TLC derived values is shown in FIG. 5A as the mean with the error bars showing the standard error of the mean. Out of a total of 12 samples studied 10 fit within this ±15% error resulting in an 83% success rate. FIG. 5B shows all the data points individually. Here 28 out of a total of 36 samples fell within the ±15% error resulting in a 78% success rate.

TABLE 1

Summary of the data shown in FIG. 5.

|  | Average | Individual Data Points |
|---|---|---|
| Within Range | 9 | 27 |
| Outside Range | 3 | 9 |
| Total # Points | 12 | 36 |
| Percent within 15% | 0.75 | 0.75 |

Figure 6:
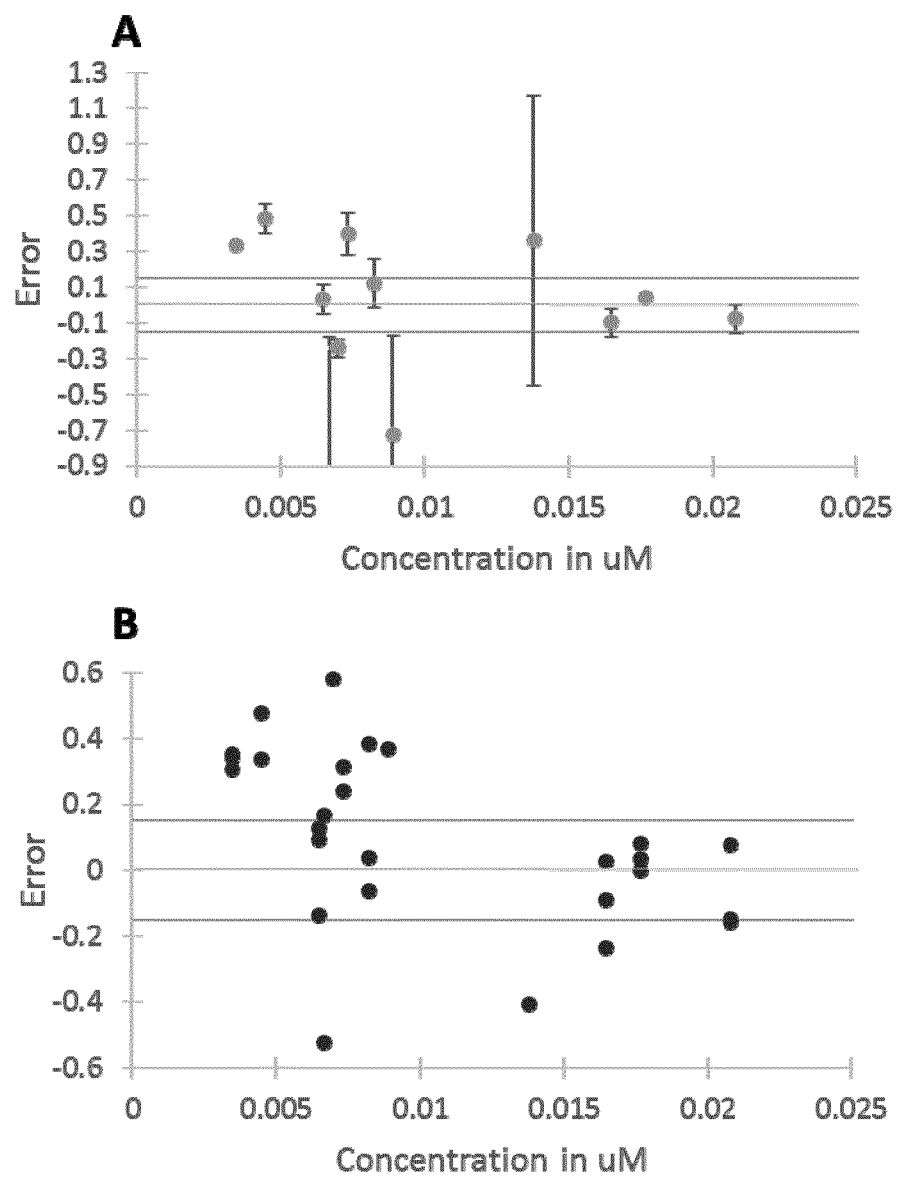

The results for Dol are shown in FIG. 6. In the depicted instance, background fluorescent levels created by light leakage through the optical filter used in the experiment resulted in a lower correlation but nevertheless the experiment confirms the utility of the hermetically sealed cartridge.

TABLE 2

Summary of the data shown in FIG. 6.

|  | Average | Individual Data Points |
|---|---|---|
| Within Range | 5 | 12 |
| Outside Range | 7 | 24 |
| Total # Points | 12 | 36 |
| Percent within 15% | 0.42 | 0.33 |

Figure 7:
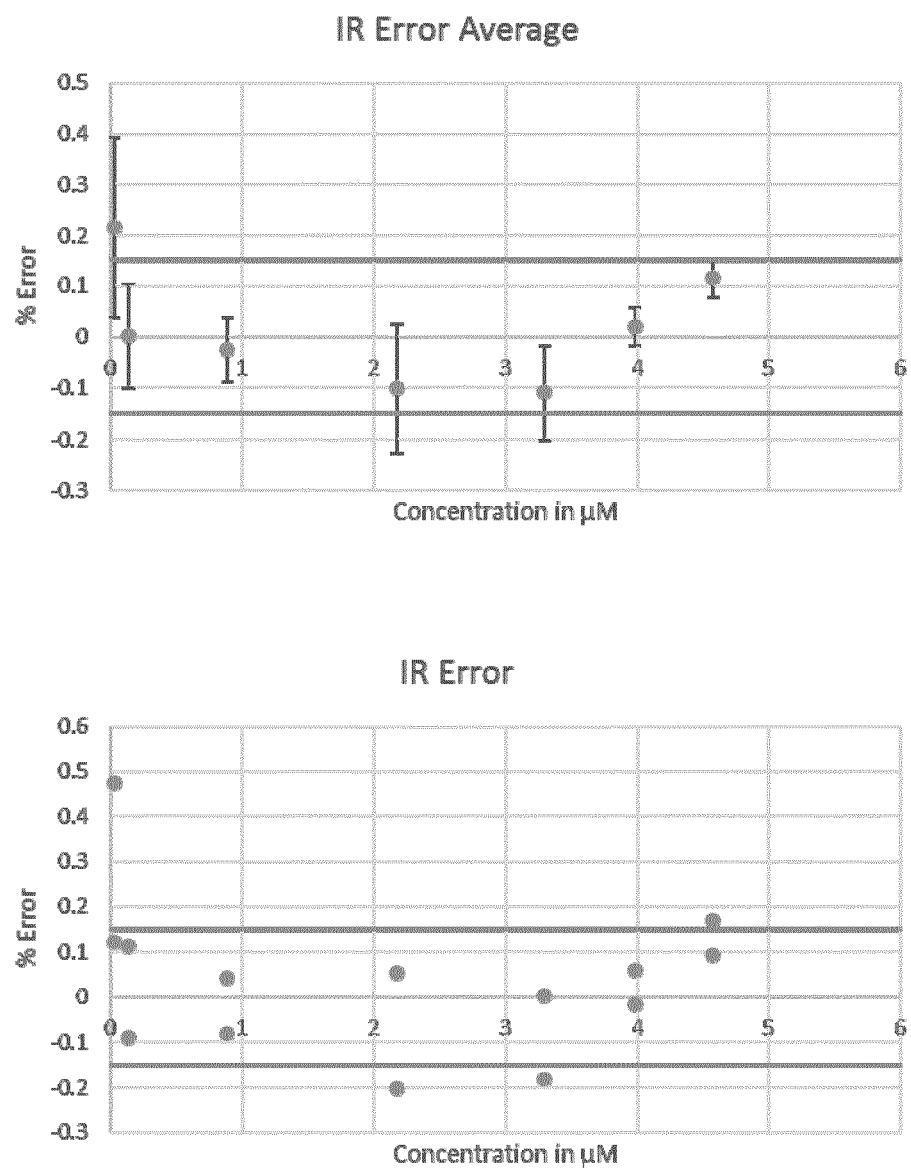

This TLC technical was also applied to a second chemotherapy drug, irinotecan, which is also inherently fluorescent. FIG. 7 shows the agreement between the TLC method and the gold standard HPLC analysis for 7 different clinical patient samples.

TABLE 3

Summary of the data shown in FIG. 7.

|  | Average | Individual Data Points |
|---|---|---|
| Within Range | 6 | 10 |
| Outside Range | 1 | 4 |
| Total # Points | 7 | 14 |
| Percent within 15% | 0.86 | 0.71 |

To better understand the minimum amount of plasma necessary to conduct the protein precipitation and TLC separation a study was conducted where spiked samples of plasma were separated into different volumes followed by the protein precipitation and spotting onto the TLC plate. As shown in FIG. 7 a strong signal can be collected even from a 5 µl sample of plasma. A typical finger stick blood drop is on the order of 50 µL [27, 28] which should produce about 25 µL of plasma [29, 30]. This shows that it is possible to successfully conduct a TLC separation using the plasma volume that could recovered by a finger stick.

Example 3—Self-Contained Cartridge Design

A self-contained cartridge was designed and built to fully contain the TLC plate and the mobile phase to prevent release of fumes or silica dust. The cartridge comprised the following components.

| Component |
|---|
| TLC plate |
| Casing |
| Insulation |
| Breakable glass barrier |
| Chloroform |
| MeOH |
| Acetic acid |

Plastics components are readily prepared by injection molding or 3-D printing, according to methods well known in the art. Plates, glass elements and solutions are available commercially, for example from Sigma Aldrich.

Access to the inside of the hermetically sealed cartridge is achieved by using hypodermic needles to pass through rubber septa placed at different locations in the cartridge as shown in FIGS. 9, 10 and 11. The design incorporates two separate chambers, one for the TLC plate and the second for the mobile phase. These two chambers keep the TLC plate separate from the mobile phase before use during transport and storage. A weak point in the separation between the chambers has been incorporated in the form of a glass coverslip which can be easily broken by inserting a needle through a designated rubber septa.

The use of the TLC cartridge use the following simple protocol:
1. Load the samples onto the TLC plate using a hypodermic needle to penetrate through the rubber septa. This step will be automated in the future.
2. Use the hypodermic needle to break the glass coverslip separating the two chambers 3. Tip up the cartridge to let the mobile phase flow into the TLC chamber and come into contact with the bottom of the TLC plate allowing the plate to develop normally by capillary forces.
4. Tip the cartridge back down to a flat orientation to stop the TLC plate development by allowing the mobile phase to drain back into the second chamber.
5. In this flat orientation the TLC plate can be imaged using a CCD camera system.

The cartridge is designed with readily available solvent resistant materials that allow it to be disposable. This prevents any cross contamination between patient samples and also reduces the maintenance burden for an automated system.

Example 4—Discussion of Examples 1 to 3

TLC has been used for drug quantification for many years [11-14], and the process has been partially automated for high throughput applications [15].

However, prior to the present invention, the TLC process has never been adapted for use in a bedside clinical setting. This is advantageous because many drugs can have significant degradation within 15 min of collection if not immediately spun down to remove red blood cells and cooled on ice [16]. Requiring the sample to be sent to the hospital lab for analysis usually incurs delay which can adversely affect the accuracy of the final blood concentration estimate.

The TLC based separation and quantification method described here has been successful in quantifying actual clinical patient samples with 83% the DOX content and 86% of the irinotecan content falling within 15% of the HPLC derived values. This method meets the FDA recommendations for the accuracy of a bioanalytical method [31]. It also shows that the process can be adapted for use with different drug compounds. The only changes that need to be made to the system to be applied to a different drug is the choice of the proper internal standard (as would be required for HPLC analysis) and the right adjustments to the single mobile phase.

The process described herein may also be used with drugs that are not inherently fluorescent. The use of TLC plates coated with an appropriate inorganic fluorescent compound (such as commercially available F254 plates) allows photon absorption of the drugs to be optically monitored using the same TLC process, except looking for blocked fluorescence from the TLC plate. The analysis of the greyscale image of the TLC plate is then inverted so the bands would show up as varying degrees of grey against a black background to allow the analysis software to quantify the band fluorescence intensity.

The custom written MatLab image analysis and quantification software was successfully applied to both the DOX and the irinotecan samples. The only changes necessary in the program parameters were to adjust the cutoff intensity values used to determine the boundaries of the actual bands because the fluorescence intensity behavior of the two compounds was different.

We also demonstrate that this simple extraction method and single mobile phase development make this TLC based technique applicable for a self-contained cartridge design. The prototype cartridge described in the preferred embodiment shown here consists of different PVC plastic layers that under compression create a sealed cartridge using fluorocarbon rubber seals. It will be appreciated that injection molding techniques could be used to create cartridges that have fewer layers and use less material.

In Summary, the TLC method described here successfully quantified over 80% of both the DOX and irinotecan clinical samples by being within 15% of established HLC values which meets the FDA criteria for accuracy of a bioanalytical method [31].

REFERENCES FOR DESCRIPTION AND EXAMPLES 1-4

1. Wilkinson, G. R., *Drug metabolism and variability among patients in drug response*. New England Journal of Medicine, 2005. 352(21): p. 2211-2221.
2. Klotz, U., *Pharmacokinetics and drug metabolism in the elderly*. Drug metabolism reviews, 2009. 41(2): p. 67-76.
3. Sawyer, M. and M. J. Ratain, *Body surface area as a determinant of pharmacokinetics and drug dosing*. Investigational new drugs, 2001. 19(2): p. 171-177.
4. Gurney, H., *Dose calculation of anticancer drugs: a review of the current practice and introduction of an alternative*. Journal of Clinical Oncology, 1996. 14(9): p. 2590-2611.
5. de Jonge, M. E., et al., *Individualised cancer chemotherapy: strategies and performance of prospective studies on therapeutic drug monitoring with dose adaptation*. Clinical pharmacokinetics, 2005. 44(2): p. 147-173.
6. Galpin, A. J. and W. E. Evans, *Therapeutic drug monitoring in cancer management*. Clinical chemistry, 1993. 39(11): p. 2419-2430.
7. Petros, W. P., et al., *Associations between drug metabolism genotype, chemotherapy pharmacokinetics, and overall survival in patients with breast cancer*. Journal of clinical oncology, 2005. 23(25): p. 6117-6125.
8. Robert, J., et al., *Pharmacokinetics of adriamycin in patients with breast cancer: correlation between pharmacokinetic parameters and clinical short-term response*. European Journal of Cancer and Clinical Oncology, 1982. 18(8): p. 739-745.
9. Touw, D., et al., *Cost-effectiveness of therapeutic drug monitoring: a systematic review*. Therapeutic drug monitoring, 2005. 27(1): p. 10-17.
10. Bardin, C., et al., *Therapeutic drug monitoring in cancer—Are we missing a trick?* European Journal of Cancer, 2014. 50(12): p. 2005-2009.
11. Yesair, D., et al., *Comparative pharmacokinetics of daunomycin and adriamycin in several animal species*. Cancer research, 1972. 32(6): p. 1177-1183.
12. Brenner, D. E., et al., *Improved high-performance liquid chromatography assay of doxorubicins detection of circulating aglycones in human plasma and comparison with thin-layer chromatography*. Cancer chemotherapy and pharmacology, 1985. 14(2): p. 139-145.
13. Chan, K. K. and C. D. Wong, *Quantitative thin-layer chromatography: thin-film fluorescence scanning analysis of adriamycin and metabolites in tissue*. Journal of Chromatography A, 1979. 172(1): p. 343-349.
14. Watson, E. and K. Chan, *Rapid analytic method for adriamycin and metabolites in human plasma by a thin-film fluorescence scanner*. Cancer treatment reports, 1976. 60(11): p. 1611-1618.
15. Fredriksson, S., K. Elwinger, and J. Pickova, *Fatty acid and carotenoid composition of egg yolk as an effect of microalgae addition to feed formula for laying hens*. Food Chemistry, 2006. 99(3): p. 530-537.
16. Kontny, N. E., et al., *Minimization of the preanalytical error in plasma samples for pharmacokinetic analyses*

*and therapeutic drug monitoring-using doxorubicin as an example.* Therapeutic drug monitoring, 2011. 33(6): p. 766-771.
17. Therasse, P., et al., *New guidelines to evaluate the response to treatment in solid tumors.* Journal of the National Cancer Institute, 2000. 92(3): p. 205-216.
18. Lennard, L., *Therapeutic drug monitoring of cytotoxic drugs.* British journal of clinical pharmacology, 2001. 52(S1): p. 75-87.
19. Ibsen, S., et al., *Extraction protocol and mass spectrometry method for quantification of doxorubicin released locally from prodrugs in tumor tissue.* Journal of Mass Spectrometry, 2013. 48(7): p. 768-773.
20. Paci, A., et al., *Review of therapeutic drug monitoring of anticancer drugs part 1—cytotoxics.* European Journal of Cancer, 2014. 50(12): p. 2010-2019.
21. Gurney, H., *How to calculate the dose of chemotherapy.* British journal of cancer, 2002. 86(8): p. 1297-1302.
22. Besse, B., et al., *2nd ESMO Consensus Conference on Lung Cancer: non-small-cell lung cancer first-line/second and further lines of treatment in advanced disease.* Annals of oncology, 2014. 25(8): p. 1475-1484.
23. Licata, S., et al., *Doxorubicin metabolism and toxicity in human myocardium: role of cytoplasmic deglycosidation and carbonyl reduction.* Chemical research in toxicology, 2000. 13(5): p. 414-420.
24. Hortobagyi, G., *Anthracyclines in the treatment of cancer.* Drugs, 1997. 54(4): p. 1-7.
25. Marangon, E., et al., *Development and Validation of a High-Performance Liquid Chromatography—Tandem Mass Spectrometry Method for the Simultaneous Determination of Irinotecan and Its Main Metabolites in Human Plasma and Its Application in a Clinical Pharmacokinetic Study.* PloS one, 2015. 10(2): p. e0118194.
26. Krischke, M., et al., *Pharmacokinetic and pharmacodynamic study of doxorubicin in children with cancer: results of a "European Pediatric Oncology Off-patents Medicines Consortium" trial.* Cancer chemotherapy and pharmacology, 2016. 78(6): p. 1175-1184.
27. McDade, T. W., S. Williams, and J. J. Snodgrass, *What a drop can do: dried blood spots as a minimally invasive method for integrating biomarkers into population-based research.* Demography, 2007. 44(4): p. 899-925.
28. Robison, E. H., et al., *Whole genome transcript profiling from fingerstick blood samples: a comparison and feasibility study.* BMC genomics, 2009. 10(1): p. 617.
29. Haeberle, S., et al., *Centrifugal extraction of plasma from whole blood on a rotating disk.* Lab on a Chip, 2006. 6(6): p. 776-781.
30. Brun, J., et al., *The paradox of hematocrit in exercise physiology: which is the "normal" range from an hemorheologist's viewpoint?* Clinical hemorheology and microcirculation, 2000. 22(4): p. 287-303.
31. Health, U.D.o. and H. Services, *Guidance for industry, bioanalytical method validation.* http://www.fda.gov/cder/guidance/index.htm, 2001.

Example 5—pH-Mediated Molecular Differentiation for Fluorimetric Quantification of Chemotherapeutic Drugs in Human Plasma Irinotecan (7-ethyl-10-[4-(1-piperidino)-1-piperidino] carbonyl-oxycamptothecin, CPT-11) is commonly used as an antitumor drug. The drug is considered a prodrug since it undergoes cleavage of the bispiperidino-side chain by carboxyesterase to form SN-38 (7-ethyl-10-hydroxycamptothecin), an active metabolite that has shown to be up to 1,000 more potent at inhibiting topoisomerase I than the parent Irinotecan.

Some of the main challenges for the simultaneous quantification of Irinotecan and SN-38 reside in the fact that their absorption and fluorescence properties are almost identical under physiological conditions, and the fact that the concentration of SN-38 can be over 30 times lower than that of Irinotecan.

The pH of the media in which molecules are dissolved can play a major role not only in properties such as their solubility, but also in their optical performance.

The premise of the pH-mediated molecular differentiation is illustrated as follows and in FIG. 14A:
Generic Case:

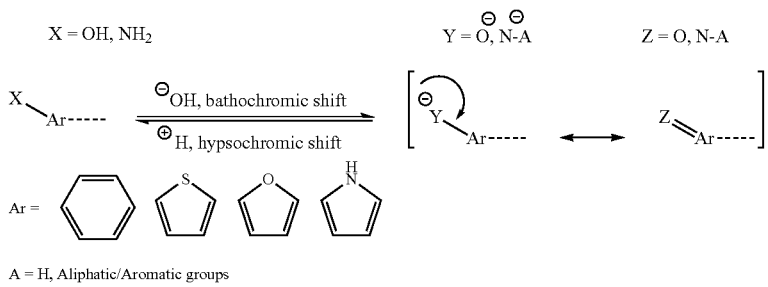

Example

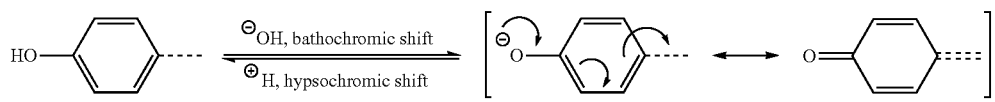

For Irinotecan and SN-38, this was investigated by characterising the absorbance as well as the emission behaviour at excitation wavelengths of 370 nm and 430 nm under acidic (pH=1.4) and basic conditions (pH=12.1). As shown in FIG. 14B, Irinotecan exhibited near identical optical properties for both absorbance and fluorescence under acidic and basic conditions, while SN-38 displayed a pronounced shift for absorbance as well as emission when basifying.

A rationalisation of the molecular structure under acidic and basic conditions is depicted in the following scheme shows the effect of pH in the chemical structure of Irinotecan (top), and SN-38 (bottom):

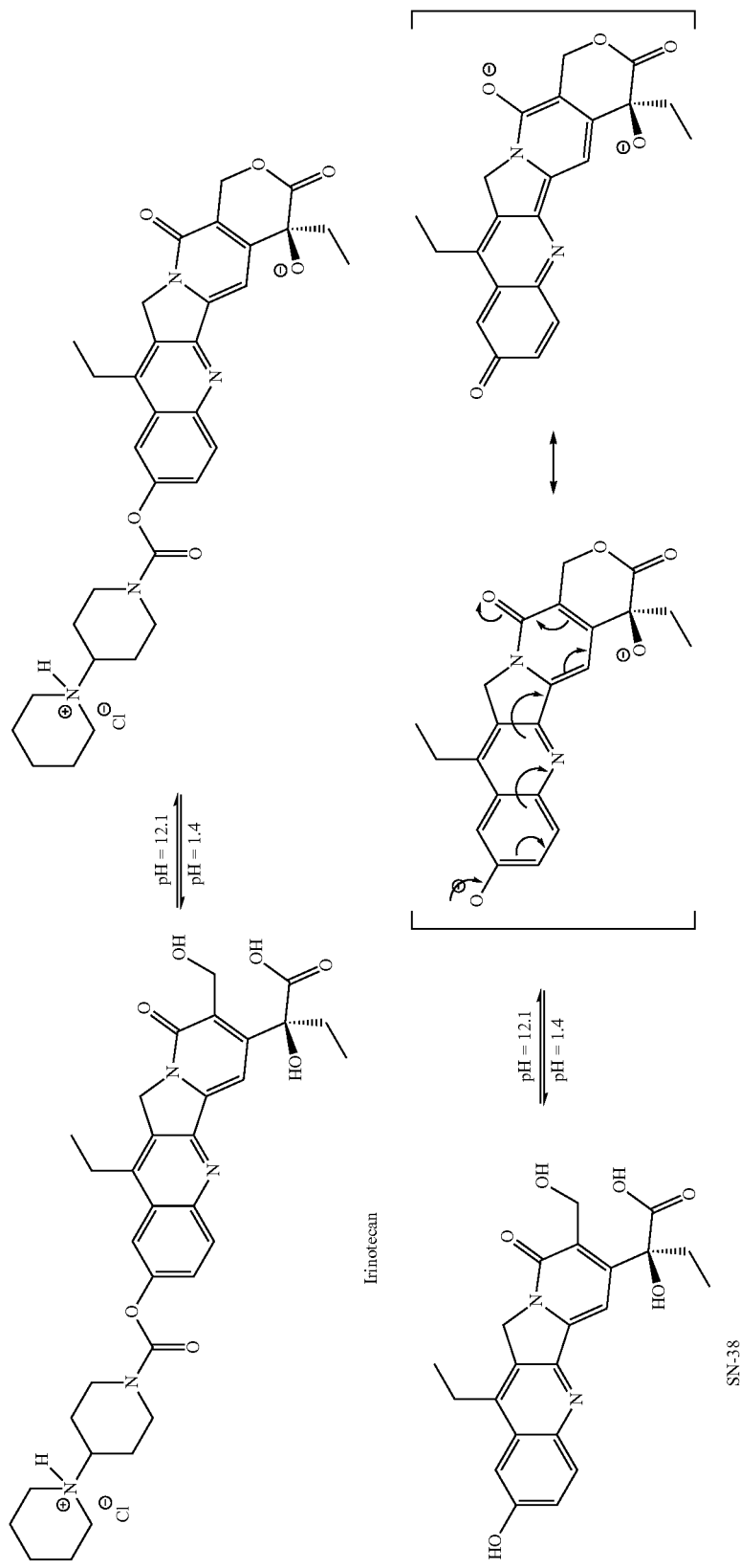

A solid phase extraction protocol was used to assess the effectiveness of a pH-mediated molecular differentiation using real patient sample compositions.

While the fluorescence of Irinotecan was measured in acidic conditions (pH=1.4) using an excitation wavelength of 370 nm, the fluorescence of SN-38 was determined in basic conditions (pH=12.1) with an excitation wavelength of 430 nm. The results are summarised in FIG. 16. In total seven samples were run in triplicate, six spiked and one reference sample. For Irinotecan, 17 out of 18 obtained data points were within 15% error (94%). In the case of SN-38, 16 out of 18 data points were within this tolerance (89%). We note that for samples with concentrations below 100 nM for Irinotecan and 15 nM for SN-38, the measured background signal of the reference sample became significant, resulting in higher errors below this level, which is at the bottom end of the relevant clinical range.

In order to show the applicability of this approach to other commonly used chemotherapeutic drugs with similar molecular structure, we compared the pH-dependent optical properties of SN-38 to Epirubicin and Methotrexate. With the former containing an alcohol and the latter an amine group attached to the aromatic core, a basic pH is likely to cause deprotonation resulting in a change of the optoelectronic properties of the molecules. The absorbance and fluorescence spectra of the three compounds were recorded in acidic (pH=1.4) and basic (pH=12.1) conditions (data not shown). In all cases, a change from acidic to basic conditions resulted in a modification in the optical properties of the drugs, with the absorption spectrum shifting to longer wavelengths, from 30 nm for Methotrexate to almost 85 nm for Epirubicin, which compared to 40 nm for SN-38. The bathochromic shift in the absorbance spectra of the molecules in basic conditions was determined to be 15 nm in the case of Methotrexate and 97 nm for Epirubicin in comparison to 137 nm for SN-38.

In conclusion, we have demonstrated that pH-mediated molecular differentiation can be utilised to quantify the amount of a chemotherapeutic prodrug and its active metabolite spiked in human plasma at clinically relevant concentrations.

Example 6—Utility of Real-Time Point-of-Care (POC) Device of the Invention in Cancer Therapeutic Drug Monitoring C-TDM Global Cancer: Scale of the Problem In 2012, there were 8.2 million deaths worldwide attributable to cancer and 14.1 million new cancer cases. 1.8 million new cases were in North America, 1 million in Europe and 4.1 million in East Asia. Despite accounting for only 20% of the global population, 43% of new cancer cases occur in developed countries. The most common cancers in the developed world are lung, colorectal, prostate and breast with lung cancer claiming the highest fatality rate for both men and women [1].

The World Health Organisation predicts that cancer cases will increase globally by 70% over the next two decades [2] and that the number of deaths will reach 13.1 million [3]. Despite increases in cancer research funding, some cancers have seen little to no progress in the last decade: brain, lung, cancer and oesophageal cancers continue to prove difficult to treat [3].

After the first administration of a chemotherapeutic agent, practitioners typically monitor drug efficacy based on the cancer or tumour's response to the drug. Methods to do this involve feeling external lumps, tumours and nodes to see if the size has decreased, doing the same but with various imaging techniques for internal cancers, blood tests such as ones that measure organ function, and tests for biomarkers that are specific to certain types of cancer. It is typical for these measurements to be taken every two to three cycles of chemotherapy, with each cycle lasting between two to six weeks [25]. This means that many patients will go for months without knowing if they are responding to treatment. There is likely a large demand for methods that will either provide more timely response data or allow drug optimisation sooner in the treatment process.

Precision Medicine and Therapeutic Drug Monitoring

Precision medicine (not limited to cancer) currently has a market size of $43 billion and is expected to grow rapidly to $71 billion by 2021 [9].

One form of precision medicine involves use of therapeutic drug monitoring (TDM). For a select variety of drugs, the serum or blood concentration correlates with efficacy [11]. The need for TDM arises when there is high inter-individual variability in the metabolism, distribution, absorption and excretion of the drug, which is a common feature of chemotherapeutic agents [11]. Plasma drug concentrations typically vary by as much as 14-fold for most chemotherapy drugs and as much as 100-fold for 5-fluorouracil. Despite this, chemotherapy dosage levels are based on estimations of the patients surface area and TDM is not commonplace; it has only seen clinical use in the monitoring of methotrexate and busulfan [11].

For a drug to benefit significantly from TDM, it must have significant variability in inter- or intra-individual pharmacokinetics, a defined relationship between blood concentration and pharmacological efficacy, a narrow therapeutic index and a precise and accurate assay to measure it. The introduction of widespread TDM for chemotherapy has been slowed primarily by the fact that there are no available assays for the drugs. However, there have also been problems in defining the relationship between blood/serum concentrations and efficacy, and the advent of combination therapies has made this even more challenging [11].

Almost all serum/blood drug concentration monitoring is carried out using HPLC or LC-MS. Methotrexate is monitored every 24 h for a period of 3 days and this is typically performed by immunoassay, though chromatography methods do exist. Plasma busulfan concentrations are routinely monitored in high dose, paediatric patients. A calibration curve consisting of seven to twelve distinct time-points is taken at the first administration of the drug with the concentration being determined by chromatography, though new ELISA methods have been developed [11].

Bach et al. [11] highlighted a number of chemotherapy drugs which they think are prospective candidates for TDM: mTOR inhibitors, 5-flourouracil, imatinib, EGF receptor inhibitors, platinum based agents, etopisode, doxorubicin and suramin. The authors highlight that many of these drugs are not subject to TDM due to poor understanding of the relationship between dose and efficacy and that strong evidence and understanding of this relationship is paramount to justify monitoring.

Point of Care Testing Market

Point of care (POC) medicine is a growing field of medical testing devices that can be used be used at, or near, the point of care, i.e. the bedside or GP surgery instead of in a medical laboratory. The benefits of point of care testing are that it brings the test immediately to the patient, meaning that the caregiver receives the results of the test faster, thereby enabling timely diagnosis and more dynamic monitoring and treatment of patients. POC testing is exceptionally important in the field of personalised, targeted medicine as it allows cheap, easy and effective ways to diagnose and monitor patients.

However POC monitoring of cancer treatment has not yet been widely accepted. This is part of a wider trend in TDM POC devices which lag behind other fields in which POC devices have been successfully deployed. Sanavio and Krol [17] suggest a variety of reasons for this in their 2015 review on the matter. One major problem is the lack of evidence to support significantly superior clinical performance, in terms of cost-effectiveness, granted by TDM for most drugs. As healthcare providers are trying to provide services at reduced cost wherever possible, TDM must be supported by strong data that it will significantly improve care to justify the cost (or it must be cheap enough that this justification is unnecessary). Another cited issue is that most drug development pipelines and clinical trials only require dose tolerance and dose response data with pharmacokinetics and pharmacodynamics data being a secondary objective at best. There is therefore often very little pharmacokinetic and pharmacodynamic data on the drug and so rarely any commentary on the efficacy of TDM. Thus when pharmaceutical companies design clinical trials, they do not presently consider TDM as an option, either when choosing which drugs to trial or when designing the format of the trial, meaning that most of the drugs on the market have little need for TDM.

The availability of a new cheaper method of performing TDM as described herein therefore provides an important contribution to the art.

Example 7—Utility of Real-Time POC Medical Device of the Invention in Other Therapeutic Areas As explained above, the present invention opens up new utilities for POC TDM analysis of drugs.

Typical examples of drugs that may typically be monitored are antiepileptics, antiarrhythmics, immunosuppressants, and antibiotics.

Some bronchodilators, psychoactive drugs and chemotherapeutics are also monitored.

Three examples of drug classes in which the invention can show particular utility are: chemotherapeutics, antiarrhythmics and fungicidal agents as all have a large portion of drugs that are recommended for monitoring or already are monitored. Furthermore these drugs have a large portion of natively fluorescent compounds which facilitates detection within the TLC cartridge platform The following table consists of drugs that are fluorescent. The drugs that are not currently monitored were identified from a range of reviews highlighting drugs that should be considered for TDM [19] [20] [21] [22] [23] [24]:

Example 8—Further Cartridge Embodiment

A further embodiment of a cartridge of the present invention is shown in FIGS. 18 to 30.

The first embodiment shown in FIGS. 10 and 11 was based on a planar (16 layer) design formed from acrylic, Viton and PTFE sheeting with an integrated glass liquid-shield that segregated the mobile phase from the TLC plate prior to elution.

The further embodiment shown in FIGS. 18 and 19 has a primarily bipartite design comprising upper (face, or front) and lower (base, or back) body units, with further elements as shown in FIGS. 19 to 29.

In this further embodiment as illustrated, the two body units are aluminium and the window is float glass.

The liquid mobile phase is segregated from the face chamber prior to elution. In this example the segregator foil (15) is aluminium foil.

O-rings (or gaskets) or septa are used to hermetically seal different fluid or vapour holding volumes of the cartridge as shown: specifically the cartridge illustrated includes a body o-ring (16), reservoir o-ring (17), window o-ring (04) and septa for injection of analytes and standards, and releasing the mobile phase (07). In this example these elements are fluoroelastomers (FKM).

This cartridge is designed so that the total mass and centre of mass of the cartridge can be adjusted by modifying the solid fill in the upper and lower units, see FIG. 21. The TLC plate is mounted and secured using the support posts shown in FIG. 25. The dimensions of the TLC plate are shown in FIG. 26.

Additional support along the backside and the incorporation of stand-off posts on the internal side of the face unit prevent both front-side wicking and rear-to-front side wicking of the liquid mobile phase during elution, see FIG. 27. These are also shown in FIG. 28.

A cross section of the bridge and injection ports shows the edge extrusions that prevent wicking, see FIG. 29.

To prepare the cartridge, the elements shown in FIG. 18 were provided.

Tension was applied by body screws (08) between the upper and lower units to form two seals. A unit seal around the outer edge of the cartridge preventing leakage of mobile phase into the working environment i.e. compression of body o-ring (16). In addition, the same tension applied by the body screws simultaneously forms a seal around the liquid mobile phase reservoir in the lower unit through compression of the reservoir o-ring (17). This is achieved through translation of force through the bridge, see FIG. 19.

The cartridge can be charged or is 'recharged' upon removal and replenishment of the TLC plate (10), segregator (15) and liquid mobile phase—see FIG. 20.

In use samples and standards can be loaded via the injection ports shown in FIGS. 17, 18, 22, 26 and 28.

The TLC plate is fully supported under each injection port such that a hypodermic needle entering the device will not deform or damage the plate whilst spotting.

The segregator foil is pierced by inserting a needle through the septum (FIG. 22, 19). The hypodermic needle is captured/engages with a well or pocket in the paddle (20) and follows a curved arc downwards (21).

This motion results in a large aperture being formed in the foil segregator, see FIG. 23. The length/height of this aperture is important as air must be allowed to back-fill the reservoir upon rotation, see FIG. 24.

The mobile phase reservoir follows a tapering 'v' contour below the TLC plate (in both the face and rear compartments) but enters a rectilinear profile before the lowest point of the TLC plate, see FIG. 30. This ensures the mobile phase wicks up the plate evenly.

TABLE D

| Leading candidate drugs for TDM. | | | |
|---|---|---|---|
| Drug Class | Drug | Therapeutic window (µg/mL) | Current TDM method |
| Antiepileptics | Stiripentol | 10-15 | AED monitoring |
| Antiarrhythmics | NAPA | 4-8 | Homogenous enzyme immunoassay |
| | Amiodarone | 0.5-2 | HPLC, LC-MS, ELISA |
| | Flecainide | 0.2-1 | HPLC, Immunoassay |
| | Mexiletine | 0.5-2.5 | HPLC, GC |
| | Quinidine | 2-5 | Homogenous enzyme immunoassay |
| | Procainamide | 4-8 | Homogenous enzyme immunoassay |
| | Propafenone | 0.06-1 | Not currently monitored |
| | Sotalol | 0.5-3 | Not currently monitored |
| | Verapamil | 0.025-0.25 | Not currently monitored |
| Antibiotics | Linezolid | 1.8-7.5 | Not currently monitored |
| | Ciprofloxacin | 0.1-8.3 | Not currently monitored |
| | Fluconazole | 1-5 | Not currently monitored |
| Antifungals | Itraconazole | 0.5-17 | Not currently monitored |
| | Voriconazole | 1-5 | Not currently monitored |
| | Posaconazole | Maintain at 0.7 | Not currently monitored |
| Immunosuppressants | Mycophenolic Acid | 1-4 | Homogenous enzyme immunoassay |
| Dermal medicines | Salicylate | 15-30 | Spectrophotometric |
| Chemotherapeutics | 5-fluoruoracil | 2000-3000 | Not currently monitored |
| | Imatinib | 1-3 | Not currently monitored |
| | Etopisode | 1-10 | Not currently monitored |
| | Doxorubicin | 10-58 | Not currently monitored |
| | Suramin | Maintain at 500 | Not currently monitored |
| | Sunitinib | Not yet determined | Not currently monitored |

| In-depth list of candidate drugs | | | | | |
|---|---|---|---|---|---|
| Class | Drug | Window | Test method | Analyte for existing test | Natively Fluorescent? |
| Antiepileptic | Carbamazepine | 5-10 ug/mL | Homogenous enzyme immunoassay | Serum, plasma | Possibly, might require acid activation |
| | Phenobarbital | 10-35 ug/mL | Homogenous enzyme immunoassay | Serum, plasma | No, requires labelling |
| | Phenytoin | 10-20 ug/mL | Homogenous enzyme immunoassay | Serum, plasma | No, requires analog |
| | Clobazam | Varies, 0.2-5 ug/mL | HPLC | Plasma | No, requires additional processing |
| | Tiagibine | 20-200 ng/mL | HPLC | Serum | Unknown |
| | Ethosuximide | 40-100 ug/mL | Enzyme immunoassay | Serum, plasma | Unknown |
| | Gabapentin | 2-20 ug/mL | Homogenous enzyme immunoassay | Serum, plasma | requires processing |
| | Lacosamide | 5-10 ug/mL | Homogenous enzyme immunoassay | Serum, plasma | Unknown |
| | Oxcarbazepine | 3-35 mg/mL | Homogenous enzyme immunoassay | Serum, Plasma | Unknown |
| | Primidone | 5-12 ug/mL | Fluoroimmunoassay | serum, plasma | No |
| | Vigabratin | 0.8-36 ug/mL | HPLC | Plasma, urine | Requires processing |
| | Zonisamide | 10-40 ug/ml | Homogenous enzyme immunoassay | Serum, plasma | Unknown, |
| | Leveltiracetam | 20-40 ug/mL | Homogenous enzyme immunoassay | Serum, plasma | No, requires derivitsation |
| | Valproic acid | 50-125 ug/mL | Homogenous enzyme immunoassay | Serum, plasma | Probably not, requires a probe |
| | Clonazepam | 20-80 ug/mL | No existing test | N/A | Requires processing |
| | Nitrazepam | 0.03-0.1 ug/mL | No existing test | N/A | Requires additions and processing |
| | Felbamate | 50-110 ug/mL | No existing test | N/A | No required probe |
| | Levetiracetam | 10-40 ug/mL | No existing test | N/A | No, requires derivitisation |
| | Topiramate | 2-10 ug/mL | No existing test | N/A | No, requires labelling |
| | Rufinamide | ~15 ug/mL | No existing test | N/A | Can't find anything |
| | Stiripentol | 10-15 ug/mL | No existing test | N/A | Yes |
| | Lamotrigine | 2.5-15 ug/mL | Homogenous enzyme immunoassay | Serum, plasma | Requires processing |
| Antiarrhythmics | Digoxin | 0.0005-0.002 ug/mL | Homogenous enzyme immunoassay | Serum, plasma | Requires processing |
| | Lidocaine | 1.5-5 ug/ml | Homogenous particle enhanced turbidimetric immunoassay | Serum, plasma | Probably not, requires a probe |
| | NAPA | 4-8 ug/mL | Homogenous enzyme immunoassay | Serum, plasma | Yes |
| | Amiodarone | 0.5-2 ug/mL | HPLC, LC-MS, ELISA | Serum, plasma | Yes |
| | Flecainide | 0.2-1 ug/mL | HPLC, immunoassay | Serum | Yes |
| | Mexiletine | 0.5-2.5 ug/mL | HPLC, GC | Serum, plasma | Yes |

TABLE D-continued

| | | | | | |
|---|---|---|---|---|---|
| | Quinidine | 2-5 ug/mL | Homogenous enzyme immunoassay | Serum, plasma | Yes |
| | Procainamide | 4-8 ug/ml | Homogenous enzyme immunoassay | Serum, plasma | Yes |
| | Disopyramide | 2-4 ug/ml | No existing test | N/A | No requires immunoassay |
| | Propafenone | 0.064-1.044 ug/mL | No existing test | N/A | Yes |
| | Sotalol | 0.5-3 ug/mL | No existing test | N/A | Yes |
| | Verapamil | 0.025-0.25 ug/mL | No existing test | N/A | Yes |
| Antibiotics | Gentamicin | 0.5-2/5-10 ug/mL | Homogenous enzyme immunoassay | Serum, plasma | No, required tagging |
| | Tobramicin | 2-10 ug/mL | Homogenous enzyme immunoassay | Serum, plasma | No, requires tagging |
| | Vancomycin | 10-20 ug/mL | Homogenous enzyme immunoassay | Serum, plasma | No, requires tagging |
| | Amikacin | 5-15 ug/mL | Homogenous particle enhanced turbidimetric immunoassay | Serum, plasma | No, requires tagging |
| | Teicoplanin | 10-60 ug/mL | No existing test | N/A | No, requires immunoassay |
| | Linezolid | 1.75-7.53 ug/ml | No existing test | N/A | Yes |
| | Ciprofloxacin | 0.1-8.3 ug/mL | No existing test | N/A | Yes |
| Antifungals | Fluconazole | 1-5 ug/mL | No existing test | N/A | Yes |
| | Itraconazole | 0.5-17 ug/mL | No existing test | N/A | Yes |
| | Voriconazole | 1-5 ug/mL | No existing test | N/A | Yes |
| | Posaconazole | ~0.7 ug/mL | No existing test | N/A | Yes |
| | Flucytosine | 70-100 ug/mL | No existing test | N/A | No |
| Antimanics | Lithium | 0.6-1.2 mEq/L | Spectrohptoemetrically with enzyme assay system | Serum | No |
| Bronchodilators | Theophylline | 5-15 ug/mL | Homogenous enzyme immunoassay | Serum, plasma | No, requires tagging |
| Immunosupressants | Cyclosporin | 0.1-0.4 ug/mL | Chemiluminescent microparticle immunoassay | Blood | No, requires analog |
| | Mycophenolic Acid | 1-4 ug/mL | Homogenous enzyme immunoassay | Plasma | Yes |
| | Tacrolimus | 5-20 ug/mL | Affinity chrome- mediated immunoassay | Blood | No, requires analog |
| | Sirolimus | 5-10 ng/mL | Chemiluminescent microparticle immunoassay | Blood | Unknown |
| | Azathioprine | can't find | No existing test | N/A | |
| | Steroids | Varies | No existing test | N/A | |
| | anti-lymphocyte globulin | can't find | No existing test | N/A | |
| | OKT3 | can't find | No existing test | N/A | |
| | Daclizumab | can't find | No existing test | N/A | |
| | Basiliximab | can't find | No existing test | N/A | |
| Antianginal | Perhexeline | 0.3-4 ug/mL | HPLC, LC-MS | Plasma | Requires processing |
| Anticonvulsant | Lamotrigine | 2.5-15 ug/mL | Homogenous enzyme immunoassay | Serum, plasma | Requires processing |
| Dermal treatment | Salicylate | 15-30 ug/mL | Spectrophotometric | Urine, serum, plasma | Yes |
| Cancer | Methotrexate | Varies with use | Homogenous enzyme immunoassay | Serum, plasma | No |
| | Busulfan | 0.9-1 ug/ml | HPLC, LC-MS | Serum, plasma | Requires processing |
| | mTOR inhibitors | 0.005-0.015 ug/mL | No existing test | | Unknown |
| | 5-flourouracil | 2000-3000 ug/ml | No existing test | | Yes |
| | imatinib | 1-3 ug/ml | No existing test | | Yes |
| | EGF receptor inhibitors | Various | No existing test | | Unknown |
| | platinum based agents | Various | No existing test | | No requires analog |
| | etopisode | 1-10 ug/mL but highly varied from patient to patient | No existing test | | Yes |
| | doxorubicin | 10.4-57.7 mg/m^2 | No existing test | | Yes |
| | suramin | max 500 ug/ml | No existing test | | Yes |
| | nilotinib | ~0.5 ug/ml | No existing test | | No requires hybridisation |
| | dasatinib | ~0.05 ug/ml | No existing test | | No requires hybridisation |
| | erlotinib | 100-150 mg/day | No existing test | | No - causes quenching of BSA |
| | sunitinib | Still being determined | No existing test | | Yes |
| | sorafenib | 800 mg/day | No existing test | | No - required fluorescent agents |

TABLE D-continued

| | | | | |
|---|---|---|---|---|
| | retuximab | Maintain at 375 mg/m² | No existing test | No-required label |
| | cetuximab | Maintain dose at 250 mg/m^2 | No existing test | No-required label |
| Antibodies for autoimmune diseases | Adalimumab | 3.5-7 ug/mL | No existing test | No - required label |
| | Certolizumab pegol | 3-84 ug/mL | No existing test | No - required label |
| | Infliximab | ~3.8 ug/mL | No existing test | No - required label |

REFERENCES FOR EXAMPLES 6 AND 7

[1] World Health Organisation, Global cancer statistics, 2012, 2015.
[2] Frost and Sullivan, Scientific Research an Advances in Cancer Therapy, 2016. [3] Frost and Sullivan, Technologies for cancer research., 2017.
[4] Allied Market Research, Oncology/cancer drugs market by therapeutic modalities (chemotherapy, targeted therapy, immunotherapy, hormonal), cancer types (blood, breast, gastrointestinal, prostate, skin, respiratory/lung cancer)—Global opportunities analysis and industry forecast, 2015.
[5] Frost and Sullivan, European cancer market, outlook., 2011.
[6] K. Stone, Top 20 Cancer Drugs, Balance. (2017). https://www.thebalance.com/top-cancer-drugs-2663234 (accessed Aug. 18, 2017).
[7] Grand View Research, Doxorubicin market by application (Ovarin, Multiple Myeloma, Kaposi Sarcoma, Leukemia, Bone Sarcoma, Breast, Endometrial, Gastric, Liver, Kidney, Other cancers) and segment forecasts, 2013-2024, 2016.
[8] Frost and Sullivan, Preferences to targeted therapies and patient centric approaches drive transformations in oncology drug delivery market, 2017.
[9] Frost and Sullivan, Technology growth series—precision medicine., 2017.
[10] Frost and Sullivan, Sensors in Medical Diagnostics and Health Monitoring, 2016.
[11] D. Bach, J. Straseski, W. Clarke, Therapeutic drug monitoring in cancer chemotherapy, Bioanalysis. 2 (2010).
[12] Frost and Sullivan, Western European point of care testing market, 2016.
[13] Frost and Sullivan, Growth opportunities in the US point-of-care market., 2016. [14] Frost and Sullivan, Innovations in precision and regenerative medicine., 2016. [15] Frost and Sullivan, Recent advances in cancer therapy., 2017.
[16] Frost and Sullivan, Recent advances in cancer immunotherapy and tumour profiling technologies, 2017.
[17] B. Sanavio, S. Krol, On the slow diffusion of point-of-care systems in therapeutic drug monitoring, Front Bioeng Biotechnol. 3 (2015).
[18] Grand View Research, Therapeutic drug monitoring market worth $3.37 billion by 2024, 2016.
[19] N. Widmer, C. Bardin, E. Chatelut, A. Paci, J. Beijnen, D. Levêque, G. Veal, A. Astier, Review of therapeutic drug monitoring of anticancer drugs part two—Targeted therapies, Eur. J. Cancer. 50 (2014) 2020-2036. doi:http://dx.doi.org/10.1016/j.ejca.2014.04.015.
[20] A. Johnston, D. W. Holt, Therapeutic drug monitoring of immunosuppressant drugs, Br. J. Clin. Pharmacol. 47 (1999) 339-350. doi:10.1046/j.1365-2125.1999.00911.x.
[21] H. R. Ashbee, R. A. Barnes, E. M. Johnson, M. D. Richardson, R. Gorton, W. W. Hope, Therapeuticdrug monitoring (TDM) of antifungal agents: guidelines from the British Society for Medical Mycology, J. Antimicrob. Chemother. 69 (2014) 1162-1176. doi:10.1093/jac/dkt508.
[22] J. A. Roberts, R. Norris, D. L. Paterson, J. H. Martin, Therapeutic drug monitoring of antimicrobials, Br. J. Clin. Pharmacol. 73 (2012) 27-36. doi:10.1111/j.1365-2125.2011.04080.x.
[23] G. Jürgens, N. A. Graudal, J. P. Kampmann, Therapeutic Drug Monitoring of Antiarrhythmic Drugs, Clin. Pharmacokinet. 42 (2003) 647-664. doi:10.2165/00003088-200342070-00004.
[24] D. Berry, Therapeutic Drug Monitoring of Antiepileptic Drugs, in: C. P. Panayiotopoulos (Ed.), Atlas of Epilepsies, Springer London, London, 2010: pp. 1487-1498. doi:10.1007/978-1-84882-128-6_222.
[25] Chemocare, How can we tell if chemotherapy is working, (2017). http://chemocare.com/chemotherapy/what-is-chemotherapy/how-to-tell-if-chemotherapy-is-working.aspx (accessed Aug. 18, 2017).
[26] A. Wadagni, M. Frimpong, D. M. Phanzu, A. Ablordey, E. Kacou, M. Gbedevi, E. Marion, Y. Xing, V. S. Babu, R. O. Phillips, M. Wansbrough-Jones, Y. Kishi, K. Asiedu, Simple, Rapid *Mycobacterium ulcerans* Disease Diagnosis from Clinical Samples by Fluorescence of Mycolactone on Thin Layer Chromatography, PLoS Negl. Trop. Dis. 9 (2015).
[27] Frost and Sullivan, Effective strategies to overcome challenges faced by global generic drug makers., 2013.
[28] Pentech Moulding Co Ltd, Cost of plastic injection moulding UK, (2015). http://pentechmoulding.co.uk/other-services/cost-of-plastic-injection-mouldingplastic-injection-moulding-uk/(accessed Aug. 18, 2017).
[29] National Clinical Guideline Centre, Preoperative tests, 2015.
[30] J. Papu, M. Rust, A. Browne, A Portable Centrifuge for Point-of-Care Measurement of Hematocrit in Low-Resource Settings, J. Near-Patient Test. Technol. (2014) 48-53.
[31] Drucker Diagnostics, QBC Dry Hematology Analyzelysers for Point of Care Testing, (2017). https://drucker-diagnostics.com/point-of-care-hematology-testing/(accessed Aug. 18, 2017).
[32] C. Chin, S. Chin, T. Laksanasopin, S. Sia, Low-Cost Microdevices for Point-of-Care Testing, in: Point Care Diagnostics a Chip, 2013: p. Chapter 1.
[33] R. Narayan, Microfluidic platforms for POC medical diagnostics, in: Med. Biosens. Point Care Appl., 2016: p. Chapter 11.

[34] Espacenet, (2017). https://worldwide.espacenet.com/ (accessed Aug. 18, 2017

The invention claimed is:

1. A method for detecting or quantifying an analyte in a sample, the method comprising the following steps (i) to (vii):
   (i) providing said sample;
   (ii) preparing an analysis sample from said sample;
   (iii) providing a thin layer chromatography (TLC) cartridge sealed by a first seal, comprising a TLC plate and a mobile phase reservoir sealed by a second seal, the mobile phase reservoir containing a TLC mobile phase;
   (iv) loading the analysis sample and one or more reference standards onto the TLC plate of the TLC cartridge, wherein the analysis sample is loaded onto a lane of the TLC plate by penetration through a septum of self-sealing material and/or the one or more reference standards are loaded onto respective lanes of the TLC plate by penetration through a septum of self-sealing material;
   (v) exposing the TLC plate to the TLC mobile phase to perform a TLC process on said analysis sample in the TLC cartridge to produce a chromatogram, wherein the exposing comprises breaking the second seal, while maintaining the first seal;
   (vi) optically analyzing analyte and reference standards bands on the chromatogram, with an imaging device to generate optical signals corresponding to the analyte and reference standards;
   (vii) detecting or quantifying the analyte in the sample according to said optical signals,
      wherein the first seal hermetically seals the TLC mobile phase prior to and during said loading, during said performance of the TLC process, and during said optical analysis.

2. The method as claimed in claim 1 wherein step (v) comprises the following substeps performed in any appropriate order:
   breaking the second seal to allow fluid access between the mobile phase reservoir and the TLC plate;
   orienting the cartridge to a first orientation that permits a base of the TLC plate to be exposed to the TLC mobile phase and start the TLC process; and
   during or after production of the chromatogram, orienting the cartridge to a second orientation that ceases exposure of the base of the TLC plate to the TLC mobile phase, to stop or slow the TLC process.

3. The method as claimed in claim 1, wherein the analyte is quantified in step (vii), and an internal standard is introduced into the analysis sample, whereby a difference between a recovered or quantified amount of the internal standard and a known amount of internal standard is used to normalize the analyte concentration.

4. The method as claimed in claim 3 wherein the internal standard is incorporated into said TLC cartridge in a sealed internal standard reservoir, which is optionally accessed by penetration through a septum of self-sealing material.

5. The method as claimed in claim 1 wherein the sample provided in step (i) is selected from the list consisting of: an environmental sample; a chemical synthesis sample; a body fluid.

6. The method as claimed in claim 5 wherein the analyte is a drug and/or a drug metabolite, and the sample is a body fluid from a subject to whom said drug has been administered.

7. The method as claimed in claim 1 wherein the analyte is a drug and/or a drug metabolite, the sample is a body fluid from a subject to whom said drug has been administered, and the drug and/or drug metabolite is quantified in step (vii) for one or more of the following purposes:
   (a) therapeutic drug monitoring;
   (b) measuring or monitoring the pharmacokinetics or pharmacodynamics of the drug;
   (c) assisting a physician to devise or adjust a dosage regimen of the drug, optionally in conjunction with observational data of side effects or therapeutic benefit of the drug in the subject;
   (d) designing or performing a regulatory trial of said drug.

8. The method as claimed in claim 1 wherein the analyte is either:
   (a) natively fluorescent;
   (b) non-natively fluorescent, but labelled with a fluorescent tag; or
   (c) non-natively fluorescent, which is assessed by absorbance or fluorescence quenching of a fluorescent TLC plate,
   and the fluorescence of the TLC plate is optically analyzed in step (vi).

9. A thin layer chromatography (TLC) cartridge sealed by a first seal, comprising a TLC plate, a septum of self-sealing material for loading an analysis sample onto a lane of the TLC plate and/or a septum of self-sealing material for loading one or more reference standards onto respective lanes of the TLC plate, and a sealed mobile phase reservoir for a TLC mobile phase sealed by a second seal, wherein the first seal is adapted to hermetically seal the TLC mobile phase prior to and during loading, during performance of a TLC process, and during analysis of a resulting TLC chromatogram.

10. The cartridge as claimed in claim 9 wherein the second seal is arranged between the mobile phase reservoir and the TLC plate, such that breakage of the second seal is configured to allow fluid access between the mobile phase reservoir and the TLC plate.

11. The cartridge as claimed in claim 9 wherein the septum of self-sealing material is an elastomeric material.

12. The cartridge as claimed in claim 9 comprising a plurality of septa of self-sealing material for loading a plurality of reference standards onto respective lanes of the TLC plate.

13. The cartridge as claimed in claim 9 wherein a plurality of reference standards are incorporated into said TLC cartridge in sealed reference standard reservoirs, which are optionally accessed by penetration through a septum of self-sealing material.

14. The cartridge as claimed in claim 9, wherein an internal standard is incorporated into said TLC cartridge in a sealed internal standard reservoir, which is optionally accessed by penetration through a septum of self-sealing material.

15. The cartridge as claimed in claim 9 wherein the cartridge comprises a sealed reservoir for a pH modifying agent, whereby in use a barrier between the pH modifying agent reservoir and the TLC plate is broken to allow fluid access between the pH modifying agent reservoir and the TLC plate, such that the pH of the TLC plate is adjusted.

16. The cartridge as claimed in claim 9 comprising:
   (i) a face unit incorporating an aperture to view a TLC plate;
   (ii) a window covering the aperture in the face unit;
   (iii) a rear unit defining a mobile phase reservoir;
   (iv) a TLC plate located between the face unit and the rear unit;

(v) a breakable barrier between the mobile phase reservoir and the TLC plate to allow fluid access between the mobile phase reservoir and the TLC plate;
(vi) a plurality of gaskets for collectively sealing at least (a) the mobile phase reservoir; and (b) a volume defined by the face unit and/or rear unit in which the TLC plate can be exposed to the mobile phase once the mobile phase is released from the mobile phase reservoir, such as to prevent mobile phase entering an external environment;

wherein:
the face unit further incorporates a plurality a septa of self-sealing material for loading reference standards and/or sample onto respective lanes of the TLC plate; and
the face unit further incorporates a septum of self-sealing material for accessing and breaking the barrier to release the mobile phase from the mobile phase reservoir into the volume defined by the face unit and/or rear unit in which the TLC plate can be exposed to the mobile phase.

17. The cartridge as claimed in claim 16 comprising a rotatable paddle for breaking the barrier to release the mobile phase from the mobile phase reservoir into the volume defined by the face unit and/or rear unit in which the TLC plate can be exposed to the mobile phase,
wherein in use the rotatable paddle is actuated by penetrating the septum of self-sealing material which permits access to the barrier with a needle, and rotating the paddle through the barrier.

18. A process for preparing a cartridge as claimed in claim 16, the process comprising:
providing the following items (i) to (ix):
(i) a face unit incorporating an aperture to view a TLC plate;
(ii) a window for covering the aperture in the face unit;
(iii) a rear unit defining a mobile phase reservoir;
(iv) a TLC plate;
(v) a breakable barrier between the mobile phase reservoir and the TLC plate to allow fluid access between the mobile phase reservoir and the TLC plate;
(vi) a plurality of gaskets for collectively sealing at least (a) the mobile phase reservoir; and (b) a volume defined by the face unit and/or rear unit in which the TLC plate can be exposed to the mobile phase once the mobile phase is released from the mobile phase reservoir, such as to prevent mobile phase entering an external environment;
(vii) a plurality of a septa of self-sealing material configured to be incorporated into the face unit for loading reference standards and/or sample onto respective lanes of the TLC plate; and
(viii) a further septum of self-sealing material configured to be incorporated into the face unit for accessing and breaking the barrier to release the mobile phase from the mobile phase reservoir into the volume defined by the face unit and/or rear unit into which the TLC plate can be exposed to the mobile phase;
(ix) a mobile phase; and
assembling items (i) to (viii) into a cartridge that hermetically seals the mobile phase during loading, performance of the TLC process, and analysis of the resulting TLC chromatogram.

19. A method of using a cartridge as claimed in claim 9, the method comprising:
(i) loading an analysis sample and reference standards onto the TLC plate;
(ii) allowing fluid access between the mobile phase reservoir and the TLC plate;
(iii) orienting the cartridge into a vertical orientation to let the mobile phase flow into contact with the base of the TLC plate allowing the TLC plate to develop normally by capillary forces;
(iv) orienting the cartridge back down to a horizontal orientation to stop development of the TLC plate.

* * * * *